(12) United States Patent
Jones et al.

(10) Patent No.: US 8,685,036 B2
(45) Date of Patent: Apr. 1, 2014

(54) ASSEMBLY TOOL FOR MODULAR IMPLANTS AND ASSOCIATED METHOD

(76) Inventors: Michael C. Jones, North Webster, IN (US); David W. Daniels, Winona Lake, IN (US)

( * ) Notice: Subject to any disclaimer, the term of this patent is extended or adjusted under 35 U.S.C. 154(b) by 327 days.

(21) Appl. No.: 12/548,037

(22) Filed: Aug. 26, 2009

(65) Prior Publication Data

US 2009/0307887 A1 Dec. 17, 2009

Related U.S. Application Data

(60) Division of application No. 10/878,292, filed on Jun. 28, 2004, now Pat. No. 7,582,092, which is a continuation-in-part of application No. 10/606,401, filed on Jun. 25, 2003, now Pat. No. 7,297,166.

(51) Int. Cl.
*A61B 17/58* (2006.01)
(52) U.S. Cl.
USPC ............................................. 606/102; 606/99
(58) Field of Classification Search
USPC .......... 606/99, 102, 104, 86, 86 R; 623/22.12
See application file for complete search history.

(56) References Cited

U.S. PATENT DOCUMENTS

| | | | |
|---|---|---|---|
| 650,795 A | 5/1900 | Maxwell et al. | |
| 1,029,402 A | 6/1912 | Ritter | |
| 1,383,304 A | 7/1921 | Hughes et al. | |
| 1,423,649 A | 7/1922 | Daniel | |
| 1,534,692 A | 4/1925 | Davis | |
| 2,631,584 A | 3/1953 | Purificato | |
| 2,661,033 A | 12/1953 | Daniel | |
| 2,711,196 A | 6/1955 | Daniel | |
| 2,834,382 A | 5/1958 | Daniel | |
| 2,856,637 A | 10/1958 | Daniel | |
| 2,864,282 A | 12/1958 | Daniel | |
| 2,877,936 A | 3/1959 | Michel | |
| 2,895,154 A | 7/1959 | Belcher | |
| 2,902,596 A | 9/1959 | Rockwell et al. | |

(Continued)

FOREIGN PATENT DOCUMENTS

| | | |
|---|---|---|
| DE | 3023942 A1 | 1/1982 |
| DE | 3538654 A1 | 4/1987 |

(Continued)

OTHER PUBLICATIONS

Gray, "Clinically-Oriented Geometry of the Femur," Thesis, Aug. 1995, Queen's University, Ontario, Canada (73 pages).

(Continued)

*Primary Examiner* — Nicholas Woodall
(74) *Attorney, Agent, or Firm* — Maginot, Moore & Beck, LLC

(57) ABSTRACT

An assembly tool for assembly of a first component of a prosthesis to a second component of the prosthesis for use in joint arthroplasty is provided. The tool includes a first member operably associated with the first component and a second member. The second member is operably associated with the second component. At least one of the first member and the second member are adapted to provide for the assembly of the first component of the prosthesis to the second component of the prosthesis. The second member is operably associated with the first member for relative motion between the first member and the second member for assembly of the first component of the prosthesis to the second component.

17 Claims, 75 Drawing Sheets

(56) References Cited

U.S. PATENT DOCUMENTS

| | | |
|---|---|---|
| 2,914,224 A | 11/1959 | Michel |
| 2,944,373 A | 7/1960 | Mentley et al. |
| 2,955,905 A | 10/1960 | Davies et al. |
| 2,957,610 A | 10/1960 | Michel |
| 2,974,699 A | 3/1961 | Boles et al. |
| 2,975,944 A | 3/1961 | Michel |
| 2,977,726 A | 4/1961 | Daniel |
| 2,981,035 A | 4/1961 | Mentley et al. |
| 2,994,461 A | 8/1961 | Michel |
| 2,994,988 A | 8/1961 | Mentley et al. |
| 3,048,307 A | 8/1962 | Michel |
| 3,059,278 A | 10/1962 | Daniel |
| 3,071,862 A | 1/1963 | Daniel et al. |
| 3,077,877 A | 2/1963 | Daniel et al. |
| 3,092,934 A | 6/1963 | Daniel |
| 3,092,935 A | 6/1963 | Daniel |
| 3,101,875 A | 8/1963 | Michel |
| 3,135,136 A | 6/1964 | Mentley et al. |
| 3,177,507 A | 4/1965 | Becker et al. |
| 3,180,532 A | 4/1965 | Michel |
| 3,220,311 A | 11/1965 | Anthony et al. |
| 3,250,745 A | 5/1966 | Davis et al. |
| 3,293,987 A | 12/1966 | Daniel |
| 3,295,987 A | 1/1967 | Hoshino et al. |
| 3,300,833 A | 1/1967 | Daniel |
| 3,301,134 A | 1/1967 | Daniel |
| 3,319,526 A | 5/1967 | Daniel et al. |
| 3,331,115 A | 7/1967 | Daniel |
| 3,335,639 A | 8/1967 | Daniel |
| 3,424,783 A | 1/1969 | Harper et al. |
| 3,443,478 A | 5/1969 | Daniel |
| 3,451,111 A | 6/1969 | Daniel |
| 3,479,387 A | 11/1969 | Daniels et al. |
| 3,479,388 A | 11/1969 | Daniels |
| 3,483,175 A | 12/1969 | Harper et al. |
| 3,494,752 A | 2/1970 | Daniel |
| 3,499,920 A | 3/1970 | Daniels |
| 3,541,868 A | 11/1970 | Hall |
| 3,580,027 A | 5/1971 | Daniel et al. |
| 3,580,029 A | 5/1971 | Daniel et al. |
| 3,604,235 A | 9/1971 | Motz et al. |
| 3,629,981 A | 12/1971 | McCaffery |
| 3,631,703 A | 1/1972 | Bregi et al. |
| 3,633,583 A | 1/1972 | Fishbein |
| 3,668,139 A | 6/1972 | Daniels et al. |
| 3,673,887 A | 7/1972 | Daniel et al. |
| 3,679,728 A | 7/1972 | Morgan et al. |
| 3,679,729 A | 7/1972 | Daniels |
| 3,691,718 A | 9/1972 | Woodruff et al. |
| 3,700,957 A | 10/1972 | Daniels |
| 3,705,513 A | 12/1972 | Daniel |
| 3,749,365 A | 7/1973 | Van Gompel |
| 3,754,586 A | 8/1973 | Daniels |
| 3,810,312 A | 5/1974 | Carson |
| 3,849,322 A | 11/1974 | Wendler et al. |
| 3,869,394 A | 3/1975 | Daniels et al. |
| 3,889,558 A | 6/1975 | Duncan |
| 3,912,727 A | 10/1975 | Daniels |
| 4,004,581 A | 1/1977 | Heimke et al. |
| 4,009,712 A | 3/1977 | Burstein et al. |
| 4,035,988 A | 7/1977 | Daniels |
| 4,051,559 A | 10/1977 | Pifferi |
| D246,507 S | 11/1977 | Danielson |
| 4,115,875 A | 9/1978 | Rambert et al. |
| 4,116,200 A | 9/1978 | Braun et al. |
| 4,150,909 A | 4/1979 | Hibarger et al. |
| D257,533 S | 11/1980 | Bevilacqua et al. |
| D258,957 S | 4/1981 | Bevilacqua et al. |
| 4,305,394 A * | 12/1981 | Bertuch, Jr. ................ 606/91 |
| D266,768 S | 11/1982 | Bevilacqua et al. |
| D267,151 S | 12/1982 | Bruce et al. |
| 4,398,074 A | 8/1983 | Danielson et al. |
| 4,457,306 A | 7/1984 | Borzone |
| D275,006 S | 8/1984 | Danielson et al. |
| 4,473,070 A | 9/1984 | Matthews et al. |
| D282,246 S | 1/1986 | Thomas et al. |
| D282,350 S | 1/1986 | Thomas et al. |
| 4,601,289 A * | 7/1986 | Chiarizzio et al. ................ 606/85 |
| D285,073 S | 8/1986 | Danielson et al. |
| D285,198 S | 8/1986 | Danielson et al. |
| 4,608,055 A | 8/1986 | Morrey et al. |
| D286,198 S | 10/1986 | Bancroft |
| D286,285 S | 10/1986 | Danielson et al. |
| D287,494 S | 12/1986 | Danielson et al. |
| D289,155 S | 4/1987 | Brooks et al. |
| 4,658,808 A | 4/1987 | Link |
| D290,399 S | 6/1987 | Kitchens |
| 4,670,015 A | 6/1987 | Freeman |
| 4,686,971 A | 8/1987 | Harris et al. |
| 4,710,946 A | 12/1987 | Hinch et al. |
| 4,716,894 A | 1/1988 | Lazzeri et al. |
| 4,738,256 A | 4/1988 | Freeman et al. |
| 4,777,942 A | 10/1988 | Frey et al. |
| 4,830,147 A | 5/1989 | Kawada |
| D303,114 S | 8/1989 | Danielson et al. |
| D304,587 S | 11/1989 | Danielson et al. |
| 4,891,545 A | 1/1990 | Capek et al. |
| 4,917,530 A | 4/1990 | Engelhardt et al. |
| 4,923,422 A | 5/1990 | Capek et al. |
| 4,938,773 A | 7/1990 | Strand |
| 4,959,066 A * | 9/1990 | Dunn et al. ................ 606/89 |
| 4,969,911 A | 11/1990 | Greene |
| D313,233 S | 12/1990 | Andrews, Sr. et al. |
| D315,343 S | 3/1991 | Andrews et al. |
| 4,997,621 A | 3/1991 | Johansson et al. |
| 5,002,578 A | 3/1991 | Luman |
| 5,002,581 A | 3/1991 | Paxson et al. |
| 5,015,255 A | 5/1991 | Kuslich |
| 5,016,858 A | 5/1991 | Mitchell |
| 5,020,519 A | 6/1991 | Hayes et al. |
| D318,051 S | 7/1991 | Danielson et al. |
| D319,439 S | 8/1991 | Danielson et al. |
| 5,047,033 A | 9/1991 | Fallin |
| 5,049,150 A | 9/1991 | Cozad |
| D320,985 S | 10/1991 | Danielson et al. |
| 5,053,037 A | 10/1991 | Lackey |
| 5,057,112 A | 10/1991 | Sherman et al. |
| 5,060,505 A | 10/1991 | Tury et al. |
| 5,061,271 A | 10/1991 | Van Zile |
| 5,080,685 A | 1/1992 | Bolesky et al. |
| D323,657 S | 2/1992 | Danielson et al. |
| 5,099,714 A | 3/1992 | Hutchison et al. |
| 5,100,407 A | 3/1992 | Conrad et al. |
| 5,108,452 A | 4/1992 | Fallin |
| 5,133,588 A | 7/1992 | Hutchinson et al. |
| 5,135,529 A | 8/1992 | Paxson et al. |
| 5,162,626 A | 11/1992 | Hutchison et al. |
| 5,171,055 A | 12/1992 | Hutchison et al. |
| 5,171,244 A | 12/1992 | Caspari et al. |
| 5,181,928 A | 1/1993 | Bolesky et al. |
| 5,184,017 A | 2/1993 | Tury et al. |
| 5,190,550 A | 3/1993 | Miller et al. |
| 5,192,283 A | 3/1993 | Ling et al. |
| 5,197,989 A | 3/1993 | Hinckfuss et al. |
| 5,201,882 A | 4/1993 | Paxson |
| 5,207,680 A | 5/1993 | Dietz et al. |
| 5,218,814 A | 6/1993 | Teal et al. |
| D337,639 S | 7/1993 | Beckman |
| 5,228,459 A | 7/1993 | Caspari et al. |
| D338,473 S | 8/1993 | Patterson et al. |
| 5,238,267 A | 8/1993 | Hutchison et al. |
| 5,247,171 A | 9/1993 | Wlodarczyk et al. |
| D340,461 S | 10/1993 | Patterson et al. |
| 5,263,498 A | 11/1993 | Caspari et al. |
| 5,290,313 A | 3/1994 | Heldreth |
| 5,304,181 A | 4/1994 | Caspari et al. |
| 5,346,979 A | 5/1994 | Stalcup et al. |
| 5,331,124 A | 7/1994 | Danielson |
| 5,336,226 A | 8/1994 | McDaniel et al. |
| 5,342,363 A * | 8/1994 | Richelsoph ................ 606/79 |
| 5,344,423 A | 9/1994 | Dietz et al. |
| 5,345,483 A | 9/1994 | Johansson et al. |
| 5,352,231 A | 10/1994 | Brumfield et al. |
| D352,521 S | 11/1994 | Sculler et al. |

(56) References Cited

U.S. PATENT DOCUMENTS

| | | | |
|---|---|---|---|
| D353,394 S | 12/1994 | Stefanski et al. | |
| 5,370,706 A | 12/1994 | Bolesky et al. | |
| 5,372,209 A | 12/1994 | Raihert et al. | |
| D355,186 S | 2/1995 | Danielson et al. | |
| D355,187 S | 2/1995 | Danielson et al. | |
| 5,387,218 A | 2/1995 | Meswania | |
| 5,395,376 A | 3/1995 | Caspari et al. | |
| D357,315 S | 4/1995 | Dietz | |
| 5,403,320 A | 4/1995 | Luman et al. | |
| 5,405,404 A | 4/1995 | Gardner et al. | |
| 5,409,492 A * | 4/1995 | Jones et al. | 606/86 R |
| 5,415,659 A | 5/1995 | Lee et al. | |
| 5,420,910 A | 5/1995 | Rudokas et al. | |
| D359,064 S | 6/1995 | Sculler et al. | |
| 5,422,478 A | 6/1995 | Wlodarczyk et al. | |
| 5,457,100 A | 10/1995 | Daniel | |
| 5,459,294 A | 10/1995 | Danielson | |
| D364,621 S | 11/1995 | Clarke et al. | |
| 5,468,243 A | 11/1995 | Halpern | |
| 5,470,336 A | 11/1995 | Ling et al. | |
| 5,474,559 A | 12/1995 | Bertin et al. | |
| 5,476,466 A | 12/1995 | Barrette et al. | |
| D365,824 S | 1/1996 | Danielson et al. | |
| 5,486,180 A | 1/1996 | Dietz et al. | |
| 5,496,324 A | 3/1996 | Barnes | |
| 5,507,815 A | 4/1996 | Wagner et al. | |
| 5,507,824 A | 4/1996 | Lennox | |
| 5,507,830 A | 4/1996 | DeMane et al. | |
| 5,507,833 A | 4/1996 | Bohn | |
| 5,527,316 A | 6/1996 | Stone et al. | |
| 5,528,640 A | 6/1996 | Johansson et al. | |
| 5,534,005 A | 7/1996 | Tokish, Jr. et al. | |
| 5,540,687 A | 7/1996 | Fairley et al. | |
| 5,540,694 A | 7/1996 | DeCarlo, Jr. et al. | |
| 5,555,551 A | 9/1996 | Rudokas et al. | |
| 5,569,255 A | 10/1996 | Burke | |
| D376,527 S | 12/1996 | Apolinski et al. | |
| 5,591,233 A | 1/1997 | Kelman et al. | |
| 5,593,411 A | 1/1997 | Stalcup et al. | |
| 5,600,892 A | 2/1997 | Peugh et al. | |
| 5,601,563 A | 2/1997 | Burke et al. | |
| 5,601,567 A | 2/1997 | Swajger et al. | |
| 5,607,269 A | 3/1997 | Dowd et al. | |
| 5,607,431 A | 3/1997 | Dudasik et al. | |
| D379,578 S | 6/1997 | Daniels | |
| 5,643,271 A | 7/1997 | Sederholm et al. | |
| 5,645,607 A | 7/1997 | Hickey | |
| 5,653,714 A | 8/1997 | Dietz et al. | |
| 5,653,764 A | 8/1997 | Murphy | |
| 5,653,765 A | 8/1997 | McTighe et al. | |
| 5,658,349 A | 8/1997 | Brooks et al. | |
| 5,663,993 A | 9/1997 | Danielson et al. | |
| 5,669,812 A | 9/1997 | Schockemoehl et al. | |
| 5,683,395 A | 11/1997 | Mikhail | |
| D387,962 S | 12/1997 | Apolinski et al. | |
| D387,963 S | 12/1997 | Clark | |
| 5,697,932 A | 12/1997 | Smith et al. | |
| 5,702,480 A | 12/1997 | Kropf et al. | |
| 5,702,487 A | 12/1997 | Averill et al. | |
| 5,715,672 A | 2/1998 | Schockemoehl et al. | |
| D392,534 S | 3/1998 | Degen et al. | |
| D392,866 S | 3/1998 | Degen et al. | |
| 5,725,592 A | 3/1998 | White et al. | |
| 5,728,128 A | 3/1998 | Crickenberger et al. | |
| 5,735,857 A | 4/1998 | Lane | |
| 5,743,915 A | 4/1998 | Bertin et al. | |
| 5,752,972 A | 5/1998 | Hoogeboom | |
| 5,755,803 A | 5/1998 | Haines et al. | |
| 5,766,261 A | 6/1998 | Neal et al. | |
| 5,769,855 A | 6/1998 | Bertin et al. | |
| 5,776,200 A | 7/1998 | Johnson et al. | |
| 5,782,921 A | 7/1998 | Colleran et al. | |
| 5,792,143 A | 8/1998 | Samuelson et al. | |
| 5,804,886 A | 9/1998 | Danielson et al. | |
| 5,810,827 A | 9/1998 | Haines et al. | |
| 5,810,829 A | 9/1998 | Elliott et al. | |
| 5,810,830 A | 9/1998 | Noble et al. | |
| 5,824,097 A | 10/1998 | Gabriel | |
| 5,849,015 A | 12/1998 | Haywood et al. | |
| 5,850,162 A | 12/1998 | Danielsons | |
| 5,853,415 A | 12/1998 | Bertin et al. | |
| 5,858,020 A | 1/1999 | Johnson et al. | |
| 5,858,828 A | 1/1999 | Seliskar et al. | |
| 5,860,969 A | 1/1999 | White et al. | |
| 5,860,981 A | 1/1999 | Bertin et al. | |
| 5,876,459 A | 3/1999 | Powell | |
| 5,879,354 A | 3/1999 | Haines et al. | |
| 5,879,391 A | 3/1999 | Slamin | |
| 5,902,340 A | 5/1999 | White et al. | |
| 5,906,644 A | 5/1999 | Powell | |
| 5,908,423 A | 6/1999 | Kashuba et al. | |
| 5,919,195 A | 7/1999 | Wilson et al. | |
| 5,923,422 A | 7/1999 | Keens et al. | |
| 5,935,172 A | 8/1999 | Ochoa et al. | |
| 5,938,701 A | 8/1999 | Hiernard et al. | |
| 5,950,121 A | 9/1999 | Kaminsky et al. | |
| 5,951,606 A | 9/1999 | Burke | |
| 5,954,460 A | 9/1999 | Degen et al. | |
| 5,957,768 A | 9/1999 | Schockemoehl et al. | |
| 5,957,925 A | 9/1999 | Cook et al. | |
| 5,966,599 A | 10/1999 | Walker et al. | |
| 5,968,049 A | 10/1999 | Da Rold | |
| 5,973,064 A | 10/1999 | Zhao et al. | |
| 5,976,145 A | 11/1999 | Kennefick, III | |
| 5,976,147 A | 11/1999 | LaSalle et al. | |
| 5,976,188 A | 11/1999 | Dextradeur et al. | |
| 5,993,455 A | 11/1999 | Noble | |
| 5,996,812 A | 12/1999 | Sokol, Jr. | |
| 5,997,419 A | 12/1999 | Daniels et al. | |
| 6,013,082 A | 1/2000 | Hiernard et al. | |
| 6,045,556 A | 4/2000 | Cohen | |
| 6,048,365 A | 4/2000 | Burrows et al. | |
| 6,054,895 A | 4/2000 | Danielsons et al. | |
| 6,056,084 A | 5/2000 | Schockemoehl et al. | |
| 6,056,754 A | 5/2000 | Haines et al. | |
| 6,058,301 A | 5/2000 | Daniels | |
| 6,059,528 A | 5/2000 | Danielson et al. | |
| 6,063,123 A | 5/2000 | Burrows et al. | |
| 6,069,048 A | 5/2000 | Daniel | |
| 6,071,311 A | 6/2000 | O'Neill et al. | |
| 6,077,783 A | 6/2000 | Allman et al. | |
| 6,080,162 A | 6/2000 | Dye et al. | |
| 6,090,146 A | 7/2000 | Rozow, III et al. | |
| 6,096,625 A | 8/2000 | Daniel et al. | |
| 6,110,179 A | 8/2000 | Flivik et al. | |
| 6,117,138 A | 9/2000 | Burrows et al. | |
| 6,120,507 A | 9/2000 | Allard et al. | |
| 6,121,147 A | 9/2000 | Daniel et al. | |
| 6,126,694 A | 10/2000 | Gray, Jr. | |
| 6,139,581 A | 10/2000 | Engh et al. | |
| 6,159,214 A | 12/2000 | Michelson | |
| 6,162,226 A | 12/2000 | DeCarlo, Jr. et al. | |
| 6,165,177 A * | 12/2000 | Wilson et al. | 606/100 |
| 6,179,116 B1 | 1/2001 | Noniewicz et al. | |
| 6,179,877 B1 | 1/2001 | Burke | |
| 6,181,925 B1 | 1/2001 | Kaminsky et al. | |
| 6,185,416 B1 | 2/2001 | Rudokas et al. | |
| 6,187,012 B1 | 2/2001 | Masini | |
| 6,193,759 B1 | 2/2001 | Ro et al. | |
| 6,197,064 B1 | 3/2001 | Haines et al. | |
| 6,197,065 B1 | 3/2001 | Martin et al. | |
| 6,201,253 B1 | 3/2001 | Allman et al. | |
| 6,206,884 B1 | 3/2001 | Masini | |
| 6,219,538 B1 | 4/2001 | Kaminsky et al. | |
| 6,224,605 B1 | 5/2001 | Anderson et al. | |
| 6,232,721 B1 | 5/2001 | Danielsons | |
| 6,235,590 B1 | 5/2001 | Daniel et al. | |
| 6,238,435 B1 | 5/2001 | Meulink et al. | |
| D443,882 S | 6/2001 | Daniels et al. | |
| 6,241,847 B1 | 6/2001 | Allman et al. | |
| 6,242,978 B1 | 6/2001 | Danielsons | |
| 6,258,093 B1 | 7/2001 | Edwards et al. | |
| 6,258,095 B1 | 7/2001 | Lombardo et al. | |
| 6,258,097 B1 | 7/2001 | Cook et al. | |

(56) References Cited

U.S. PATENT DOCUMENTS

| | | |
|---|---|---|
| 6,260,279 B1 | 7/2001 | Apolinski et al. |
| 6,263,998 B1 | 7/2001 | Schockemoehl et al. |
| 6,264,699 B1 | 7/2001 | Noiles et al. |
| 6,270,502 B1 | 8/2001 | Stulberg |
| 6,281,935 B1 | 8/2001 | Twitchell et al. |
| 6,285,871 B1 | 9/2001 | Daniels |
| 6,287,342 B1 | 9/2001 | Copf et al. |
| 6,310,410 B1 | 10/2001 | Lin et al. |
| D450,304 S | 11/2001 | Daniels et al. |
| 6,316,817 B1 | 11/2001 | Seliskar et al. |
| 6,318,651 B1 | 11/2001 | Spiering |
| 6,319,286 B1 | 11/2001 | Fernandez et al. |
| 6,330,845 B1 * | 12/2001 | Meulink ............ 81/462 |
| 6,332,886 B1 | 12/2001 | Green et al. |
| 6,335,766 B1 | 1/2002 | Twitchell et al. |
| 6,354,908 B2 | 3/2002 | Allman et al. |
| 6,355,068 B1 | 3/2002 | Doubler et al. |
| 6,355,532 B1 | 3/2002 | Seliskar et al. |
| 6,361,563 B2 | 3/2002 | Terrill-Grisoni et al. |
| 6,366,422 B1 | 4/2002 | Daniel et al. |
| 6,372,520 B1 | 4/2002 | Hsia et al. |
| D457,176 S | 5/2002 | Daniels et al. |
| 6,382,276 B1 | 5/2002 | Daniels et al. |
| D458,947 S | 6/2002 | Svetlik et al. |
| 6,400,415 B1 | 6/2002 | Danielsons |
| 6,406,217 B1 | 6/2002 | Daniel et al. |
| 6,419,147 B1 | 7/2002 | Daniel |
| 6,422,562 B1 | 7/2002 | Daniel |
| 6,422,816 B1 | 7/2002 | Danielson |
| 6,428,578 B2 | 8/2002 | White |
| 6,432,110 B1 | 8/2002 | Richelsoph |
| 6,432,141 B1 | 8/2002 | Stocks et al. |
| 6,440,139 B2 | 8/2002 | Michelson |
| D467,485 S | 12/2002 | Daniels et al. |
| 6,488,713 B1 | 12/2002 | Hershberger |
| 6,491,696 B1 | 12/2002 | Kunkel |
| D468,180 S | 1/2003 | Bruno et al. |
| 6,506,684 B1 | 1/2003 | Daniel et al. |
| 6,508,841 B2 | 1/2003 | Martin et al. |
| D469,671 S | 2/2003 | Prell et al. |
| 6,517,581 B2 | 2/2003 | Blamey |
| RE38,058 E | 4/2003 | Fallin |
| 6,565,029 B2 | 5/2003 | Zweighaft et al. |
| 6,568,618 B1 | 5/2003 | Vanderheyden et al. |
| 6,589,284 B1 | 7/2003 | Silberer |
| 6,589,285 B2 | 7/2003 | Penenberg |
| 6,600,516 B1 | 7/2003 | Danielsons et al. |
| 6,609,900 B2 | 8/2003 | Lucke et al. |
| 6,613,091 B1 | 9/2003 | Zdeblick et al. |
| 6,663,616 B1 | 12/2003 | Roth et al. |
| 6,676,706 B1 | 1/2004 | Mears et al. |
| 6,682,568 B2 | 1/2004 | Despres, III et al. |
| 6,692,530 B2 | 2/2004 | Doubler et al. |
| 6,700,359 B2 | 3/2004 | Daniels et al. |
| 6,702,854 B1 | 3/2004 | Cheal et al. |
| 6,706,072 B2 | 3/2004 | Dwyer et al. |
| 6,706,621 B2 | 3/2004 | Cox et al. |
| 6,712,825 B2 | 3/2004 | Aebi et al. |
| 6,723,129 B2 | 4/2004 | Dwyer et al. |
| 6,740,090 B1 | 5/2004 | Cragg et al. |
| 6,743,235 B2 | 6/2004 | Subba Rao |
| 6,744,243 B2 | 6/2004 | Daniels et al. |
| 6,751,266 B1 | 6/2004 | Danielsons |
| 6,755,841 B2 | 6/2004 | Fraser et al. |
| 6,770,100 B2 | 8/2004 | Draenert |
| 6,793,208 B1 | 9/2004 | Riddle, Jr. et al. |
| D497,499 S | 10/2004 | Daniel et al. |
| 6,811,376 B2 | 11/2004 | Arel et al. |
| 6,812,792 B2 | 11/2004 | Mattsson et al. |
| 6,824,552 B2 | 11/2004 | Robison et al. |
| 6,840,944 B2 | 1/2005 | Suddaby |
| 6,846,314 B2 | 1/2005 | Shapira |
| 6,856,029 B1 | 2/2005 | Daniel et al. |
| 6,870,160 B1 | 3/2005 | Daniel |
| 6,875,218 B2 | 4/2005 | Dye et al. |
| 6,883,217 B2 * | 4/2005 | Barrette et al. ............ 29/256 |
| D505,611 S | 5/2005 | Daniel et al. |
| 6,905,515 B1 | 6/2005 | Gilbertson |
| 6,911,048 B2 | 6/2005 | Fernandez et al. |
| 6,949,101 B2 | 9/2005 | McCleary et al. |
| 6,990,691 B2 | 1/2006 | Klotz et al. |
| 7,001,392 B2 | 2/2006 | McGovern |
| 7,008,420 B2 | 3/2006 | Okada |
| 7,022,141 B2 | 4/2006 | Dwyer et al. |
| 7,066,042 B2 | 6/2006 | Andrews et al. |
| 7,074,224 B2 | 7/2006 | Daniels et al. |
| 7,188,556 B1 | 3/2007 | Rinner |
| 7,189,242 B2 | 3/2007 | Boyd et al. |
| 7,204,851 B2 | 4/2007 | Trieu et al. |
| 7,297,166 B2 | 11/2007 | Dwyer et al. |
| 7,363,838 B2 | 4/2008 | Abdelgany |
| 7,387,635 B2 | 6/2008 | Keller |
| 7,431,723 B2 | 10/2008 | Hazelbrouck |
| 7,582,092 B2 * | 9/2009 | Jones et al. ............ 606/102 |
| 7,585,329 B2 | 9/2009 | McCleary et al. |
| 7,641,658 B2 | 1/2010 | Shaolian et al. |
| 2001/0001121 A1 | 5/2001 | Lombardo et al. |
| 2001/0007957 A1 | 7/2001 | Martin et al. |
| 2001/0016779 A1 | 8/2001 | Lubinus |
| 2001/0021622 A1 | 9/2001 | Allman et al. |
| 2001/0034526 A1 | 10/2001 | Kuslich et al. |
| 2002/0004684 A1 | 1/2002 | Thomas et al. |
| 2002/0043296 A1 | 4/2002 | Daniels et al. |
| 2002/0058999 A1 | 5/2002 | Dwyer et al. |
| 2002/0059000 A1 | 5/2002 | Dwyer et al. |
| 2002/0127115 A1 | 9/2002 | Lucke et al. |
| 2002/0183758 A1 | 12/2002 | Middleton et al. |
| 2002/0195512 A1 | 12/2002 | Zweighft et al. |
| 2003/0001551 A1 | 1/2003 | Daniels et al. |
| 2003/0048003 A1 | 3/2003 | Daniels et al. |
| 2003/0050645 A1 | 3/2003 | Parker et al. |
| 2003/0071329 A1 | 4/2003 | Cox et al. |
| 2003/0093080 A1 | 5/2003 | Brown et al. |
| 2003/0095368 A1 | 5/2003 | Daniels et al. |
| 2003/0109882 A1 | 6/2003 | Shirado et al. |
| 2003/0114933 A1 | 6/2003 | Bouttens et al. |
| 2003/0130740 A1 | 7/2003 | Stocks et al. |
| 2003/0149487 A1 | 8/2003 | Doubler et al. |
| 2003/0171756 A1 | 9/2003 | Fallin et al. |
| 2003/0171816 A1 | 9/2003 | Scifert et al. |
| 2003/0180146 A1 | 9/2003 | Arel et al. |
| 2003/0187449 A1 | 10/2003 | McCleary et al. |
| 2003/0204269 A1 | 10/2003 | Gerbec et al. |
| 2003/0220698 A1 | 11/2003 | Mears et al. |
| 2003/0225417 A1 | 12/2003 | Fischell et al. |
| 2003/0228033 A1 | 12/2003 | Daniel et al. |
| 2004/0010262 A1 | 1/2004 | Parkinson et al. |
| 2004/0015239 A1 | 1/2004 | Beguec |
| 2004/0017085 A1 | 1/2004 | Daniels |
| 2004/0054373 A1 | 3/2004 | Serra et al. |
| 2004/0054419 A1 | 3/2004 | Serra et al. |
| 2004/0058997 A1 | 3/2004 | Daniel |
| 2004/0064186 A1 | 4/2004 | McCleary et al. |
| 2004/0066217 A1 | 4/2004 | Daniels et al. |
| 2004/0073315 A1 | 4/2004 | Justin et al. |
| 2004/0092951 A1 | 5/2004 | Serra et al. |
| 2004/0111861 A1 | 6/2004 | Barrette et al. |
| 2004/0122437 A1 * | 6/2004 | Dwyer et al. ............ 606/87 |
| 2004/0122439 A1 | 6/2004 | Dwyer et al. |
| 2004/0122440 A1 | 6/2004 | Daniels et al. |
| 2004/0122525 A1 | 6/2004 | Daniels et al. |
| 2004/0130394 A1 | 7/2004 | Mattson et al. |
| 2004/0135233 A1 | 7/2004 | Cox et al. |
| 2004/0147933 A1 | 7/2004 | McGovern |
| 2004/0172138 A1 | 9/2004 | May et al. |
| 2004/0172139 A1 | 9/2004 | Dwyer et al. |
| 2004/0210471 A1 | 10/2004 | Luby et al. |
| 2004/0236342 A1 | 11/2004 | Ferree et al. |
| 2004/0260297 A1 | 12/2004 | Padget et al. |
| 2004/0267266 A1 | 12/2004 | Daniels et al. |
| 2004/0267267 A1 | 12/2004 | Daniels et al. |
| 2004/0267372 A1 | 12/2004 | Vanasse et al. |
| 2004/0267373 A1 | 12/2004 | Dwyer et al. |
| 2005/0004679 A1 | 1/2005 | Sederholm et al. |

(56) References Cited

U.S. PATENT DOCUMENTS

| | | |
|---|---|---|
| 2005/0010992 A1 | 1/2005 | Klotz et al. |
| 2005/0015049 A1 | 1/2005 | Rioux et al. |
| 2005/0033444 A1 | 2/2005 | Jones et al. |
| 2005/0047239 A1 | 3/2005 | Takahashi et al. |
| 2005/0057239 A1 | 3/2005 | Fowler et al. |
| 2005/0078289 A1 | 4/2005 | Daniel et al. |
| 2005/0081910 A1 | 4/2005 | Danielson et al. |
| 2005/0085820 A1 | 4/2005 | Collins et al. |
| 2005/0115391 A1 | 6/2005 | Baker et al. |
| 2005/0154331 A1 | 7/2005 | Christie et al. |
| 2005/0188878 A1 | 9/2005 | Baker et al. |
| 2005/0209597 A1 | 9/2005 | Long et al. |
| 2005/0222572 A1 | 10/2005 | Chana |
| 2005/0234461 A1 | 10/2005 | Burdulis et al. |
| 2005/0234559 A1 | 10/2005 | Fernandez et al. |
| 2005/0261702 A1 | 11/2005 | Oribe et al. |
| 2005/0267937 A1 | 12/2005 | Daniels et al. |
| 2005/0288676 A1 | 12/2005 | Schnieders et al. |
| 2006/0015110 A1 | 1/2006 | Pepper |
| 2006/0027027 A1 | 2/2006 | Serra et al. |
| 2006/0058810 A1 | 3/2006 | Wozencroft et al. |
| 2006/0217737 A1 | 9/2006 | Iversen |
| 2006/0260440 A1 | 11/2006 | Abdelgany |
| 2007/0005144 A1 | 1/2007 | Leisinger et al. |
| 2007/0123908 A1 | 5/2007 | Jones et al. |
| 2007/0260315 A1 | 11/2007 | Foley et al. |
| 2008/0077156 A1 | 3/2008 | Emstad |
| 2008/0091212 A1 | 4/2008 | Dwyer et al. |
| 2008/0114367 A1 | 5/2008 | Meyer |
| 2008/0275457 A1 | 11/2008 | Meek et al. |
| 2009/0112216 A1 | 4/2009 | Leisinger |
| 2009/0112218 A1 | 4/2009 | McCleary et al. |
| 2009/0187251 A1 | 7/2009 | Justin et al. |
| 2009/0307887 A1 | 12/2009 | Jones et al. |

FOREIGN PATENT DOCUMENTS

| | | | |
|---|---|---|---|
| DE | 10014401 A1 | 6/2001 | |
| DE | 20114835 U1 | 1/2002 | |
| DE | 202006000845 U1 | 5/2006 | |
| EP | 0206777 A2 | 12/1986 | |
| EP | 333990 A2 | 9/1989 | |
| EP | 0726063 A1 | 8/1996 | |
| EP | 0842639 A2 | 5/1998 | |
| EP | 0595956 B1 | 9/1998 | |
| EP | 0511244 B1 | 10/1998 | |
| EP | 1000595 A1 | 5/2000 | |
| EP | 1084680 A2 | 3/2001 | |
| EP | 1080701 | 7/2001 | |
| EP | 1080701 A3 | 7/2001 | |
| EP | 0661023 B1 | 8/2001 | |
| EP | 1201191 A1 | 5/2002 | |
| EP | 0728449 B1 | 7/2002 | |
| EP | 0861635 B1 | 7/2002 | |
| EP | 1323395 A2 | 7/2003 | |
| EP | 1348384 A2 | 10/2003 | |
| EP | 1369089 A2 | 12/2003 | |
| EP | 1435223 A1 | 7/2004 | |
| EP | 1493407 A2 | 1/2005 | |
| EP | 1522284 A2 | 4/2005 | |
| EP | 1263334 B1 | 10/2005 | |
| EP | 1591084 A1 | 11/2005 | |
| EP | 1191906 B1 | 6/2006 | |
| EP | 1080701 B1 | 8/2006 | |
| EP | 1738723 A1 | 1/2007 | |
| EP | 1905396 A1 | 4/2008 | |
| EP | 2055273 A1 | 5/2009 | |
| EP | 2057969 A2 | 5/2009 | |
| FR | 2606628 A1 | 5/1988 | |
| FR | 2699400 A1 | 6/1994 | |
| FR | 2737107 A1 | 1/1997 | |
| FR | 2828397 A1 | 2/2003 | |
| FR | 2926212 A1 | 7/2009 | |
| GB | 2250441 A | 6/1992 | |
| JP | 5212069 A | 8/1993 | |
| JP | 10-80095 A | 3/1998 | |
| JP | 2000210314 A | 8/2000 | |
| JP | 2002-153479 A | 5/2002 | |
| JP | 2003339724 A | 12/2003 | |
| JP | 2004-251450 A | 9/2004 | |
| JP | 2006501917 A | 1/2006 | |
| WO | 9110408 A1 | 7/1991 | |
| WO | 9210138 A1 | 6/1992 | |
| WO | 9301769 A1 | 2/1993 | |
| WO | 9412123 A1 | 6/1994 | |
| WO | 9427507 A1 | 12/1994 | |
| WO | 9615738 A1 | 5/1996 | |
| WO | 9615739 | 5/1996 | |
| WO | 9815739 A1 | 4/1998 | |
| WO | 01/67997 A1 | 9/2001 | |
| WO | 02102254 A2 | 12/2002 | |
| WO | 03015642 A1 | 2/2003 | |
| WO | 03065906 A2 | 8/2003 | |
| WO | 03082159 A1 | 10/2003 | |
| WO | 03092513 A1 | 11/2003 | |
| WO | 03094698 A2 | 11/2003 | |
| WO | 03094803 A1 | 11/2003 | |
| WO | 2004089224 A2 | 10/2004 | |
| WO | 2007098549 A1 | 9/2007 | |

OTHER PUBLICATIONS

Zimmer, "Metasul LDH Large Diameter Head," Surgical Technique, available at least as early as Sep. 28, 2006, (19 pages).

European Search Report corresponding to European patent application EP 08 16 7776, dated Feb. 11, 2010, 5 pages.

Chinese Office Action corresponding to Chinese patent application 200710185735.6, dated Feb. 11, 2011, 13 pages.

European Search Report corresponding to European patent application EP 11 15 1451, dated Feb. 16, 2011, 5 pages.

European Search Report corresponding to European Application No. 08167776.7, dated Feb. 22, 2010 (5 pages).

European Search Report corresponding to European Application No. 09168260.9, dated Jan. 13, 2010 (3 pages).

Paul, Howard A., et al, "Development of a Surgical Robot for Cementless Total Hip Arthroplasty," Clinical Orthopaedics and Related Research, No. 285, Dec. 1992, pp. 57-66 (10 pages).

Depuy Orthopaedics, Inc., "S-ROM Modular Hip System, Minimally Invasive Calcar Miller Surgical Technique," 0612-04-503, 2004 (12 pages).

European Search Report corresponding to Application No. EP 11169798.3-2310, dated Aug. 10, 2011 (6 pages).

European Search Report corresponding to Application No. EP 11175823.1-2310, dated Nov. 25, 2011 (6 pages).

Zimmer, Fracture Equipment and Orthopedic Appliances, p. 51, published at least as early as Sep. 29, 2005 (1 page).

DePuy, S-ROM Modular Hip System, retrieved from Johnson & Johnson Gateway website on Sep. 26, 2005 (1 page).

English translation of Japanese Notification of Reasons for Refusal in corresponding Japanese patent application (i.e., JP 2007-254241), mailed Jun. 19, 2012 (2 pages).

\* cited by examiner

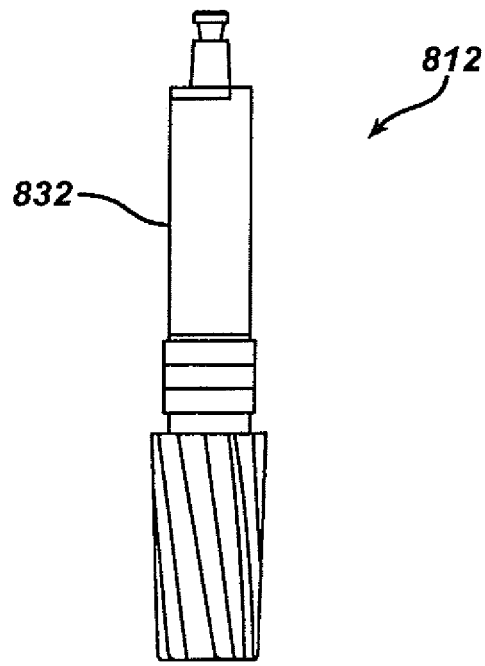
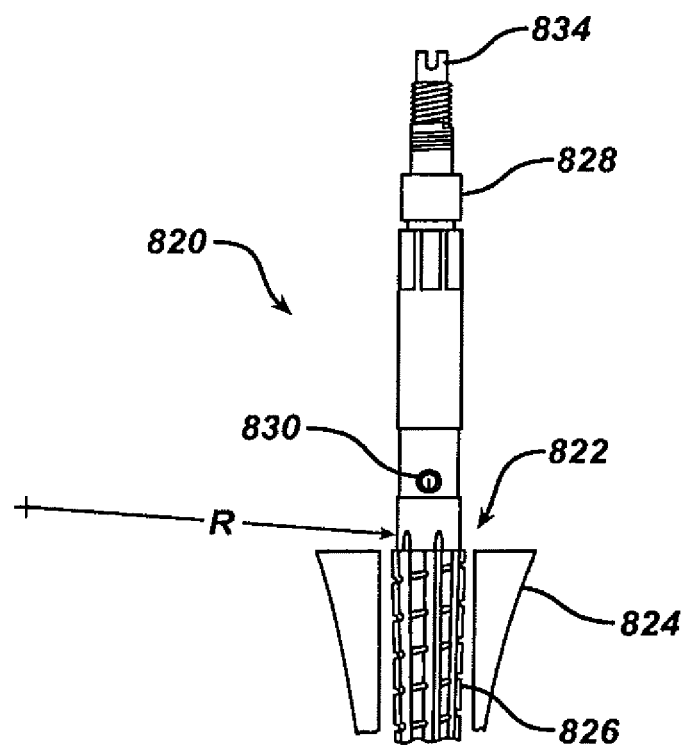
FIG. 32

1310 — Providing a prosthesis including a first component and a second component removably attachable to the first component 1312 — Providing a instrument having a first member operably associated with the first component, the first member including a first member relative motion feature and a body defining a generally cylindrical longitudinal opening therin, a second member operably associated with a second component, the second member operably associated with the first member for relative motion therebetween for assembly of the first component of the prosthesis to the second component, and an angular orientation feature cooperating with at least one of the first member and the second member for at least one of replicating and measuring the relative angular orientation of the first component with respect to the second component 1314 — Assembling the first component to the second component 1316 — Connecting the first member of the tool to the first component 1318 — Connecting the second member of the tool to the second component 1320 — Rotating the first member of the tool with respect to the second member of the tool to secure the first component to the second component

- 1410: Providing a trial prosthesis including a stem trial portion for implantation at least partially into the femoral canal of a femur and a neck trial portion extending from the stem portion
- 1412: Positioning the stem trial portion in the femoral canal
- 1414: Positioning the neck trial portion relative to the stem trial portion
- 1416: Securing the neck trial portion to the stem trial portion
- 1418: Trialing the trial prosthesis
- 1420: Attaching an insrument to the stem trial portion and the neck trial portion
- 1422: Measuring the relative position of the stem trial portion to the neck trial portion
- 1424: Providing a implant prosthesis including a stem implant portion for implantation at least partially into the femoral canal of a femur and a neck implant portion extending from the stem portion
- 1426: Providing an instrument to secure the stem implant portion to the neck implant portion while angularly orienting the stem implant portion to the neck implant portion

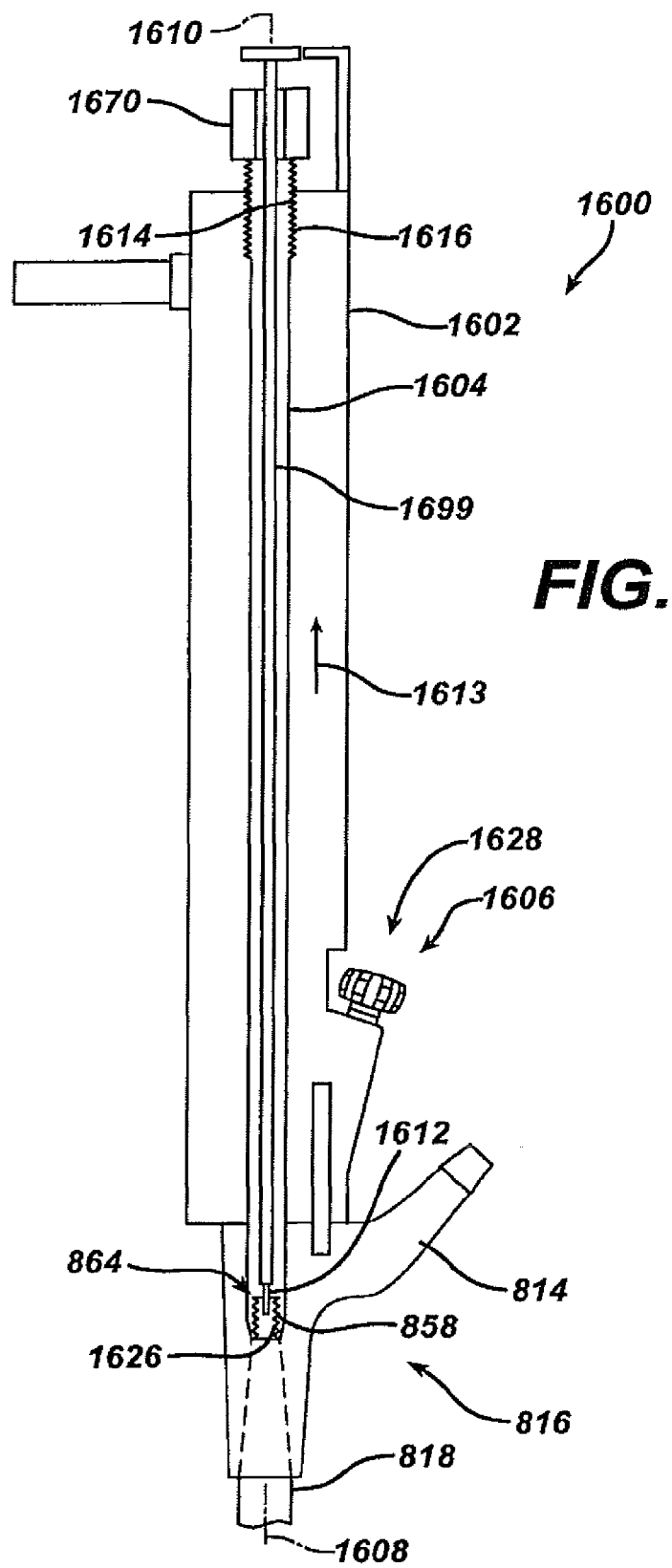
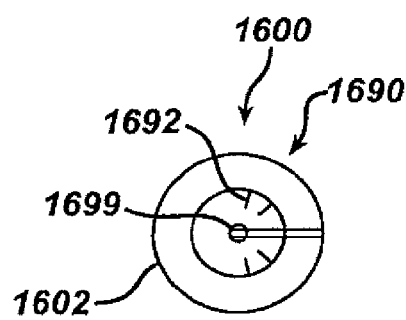
FIG. 74
FIG. 74B

ASSEMBLY TOOL FOR MODULAR IMPLANTS AND ASSOCIATED METHOD

CROSS REFERENCE TO RELATED APPLICATIONS

This application is a Divisional of U.S. application Ser. No. 10/878,292, filed Jun. 28, 2004, entitled ASSEMBLY TOOL FOR MODULAR IMPLANTS AND ASSOCIATED METHOD, (now U.S. Pat. No. 7,582,092 issued Sep. 1, 2009), which is a Continuation-in-Part of U.S. application Ser. No. 10/606,401 filed Jun. 25, 2003, entitled ASSEMBLY TOOL FOR MODULAR IMPLANTS AND ASSOCIATED METHOD (now U.S. Pat. No. 7,297,166 issued Nov. 20, 2007), the disclosures of each of the above-identified patents are hereby totally incorporated by reference in their entirety.

TECHNICAL FIELD

The present invention relates generally to the field of orthopaedics, and more particularly, to an implant for use in arthroplasty.

BACKGROUND

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

During performance of a joint replacement procedure, it is generally necessary to provide the surgeon with a certain degree of flexibility in the selection of a prosthesis. In particular, the anatomy of the bone into which the prosthesis is to be implanted may vary somewhat from patient to patient. Such variations may be due to, for example, the patient's age, size and gender. For example, in the case of a femoral prosthesis, the patient's femur may be relatively long or relatively short thereby requiring use of a femoral prosthesis, which includes a stem that is relatively long or short, respectively. Moreover, in certain cases, such as when use of a relatively long stem length is required, the stem must also be bowed in order to conform to the anatomy of the patient's femoral canal.

Such a need for prostheses of varying shapes and sizes thus creates a number of problems in regard to the use of a one-piece prosthesis. For example, a hospital or surgery center must maintain a relatively large inventory of prostheses in order to have the requisite mix of prostheses needed for certain situations, such as trauma situations and revision surgery. Moreover, since the bow of the stem must conform to the bow of the intramedullary canal of the patient's femur, rotational positioning of the upper portion of the prosthesis is limited thereby rendering precise location of the upper portion and hence the head of the prosthesis very difficult.

In addition, since corresponding bones of the left and right side of a patient's anatomy (e.g. left and right femur) may bow in opposite directions, it is necessary to provide (left) and (right) variations of the prosthesis in order to provide anteversion of the bone stem, thereby further increasing the inventory of prostheses which must be maintained.

As a result of these and other drawbacks, a number of modular prostheses have been designed. As its name implies, a modular prosthesis is constructed in modular form so that the individual elements or figures of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position which conforms to the patient's anatomy while also allowing for a limited degree of independent positioning of the proximal neck component relative to the patient's pelvis.

One issue that arises as a result of the use of a modular prosthesis is the locking of the components relative to one another. In particular, firm reproducible locking of the proximal neck component to the distal stem component is critical to prevent separation of the two components subsequent to implantation thereof into the patient. The need for the firm locking is particularly necessary if the design does not provide for positive locking with weight bearing. As such, a number of locking mechanisms have heretofore been designed to lock the components of a modular prosthesis to one another. For example, a number of modular prostheses have heretofore been designed to include a distal stem component, which has an upwardly extending post, which is received into a bore defined distal neck component. A relatively long fastener such as a screw or bolt is utilized to secure the post with the bore. Other methods of securing modular components include the impacting of one component onto the other. This method has highly variable results Current designs of modular stems include designs in which the modular connection utilizes a tapered fit between the two components. For example, the proximal body may include an internal taper, which mates with an external taper on the distal stem. Such a taper connection may be used in conjunction with additional securing means, for example, a threaded connection or may be used alone. It is important that the tapered connection be secure. For example, the proper amount of force must be applied to the tapered connection to properly secure the tapered connection so that the connection can withstand the forces associated with the operation of the stem.

Current attempts to provide a device to adjoin components of a modular joint prosthesis are fraught with several problems. For example, the device may not provide sufficient mechanical advantage to securely lock the components. Further, the ergonomics available to lock the components may not be optimal. Further, a device relying solely on the displacement for a taper connection may not provide sufficient force as there may not be an accurate correspondence of displacement to the clamping force. Further, utilizing a displacement method may make it possible to overtighten and damage the components. Further, prior art solutions may be difficult to manufacture or expensive to make. Further prior art devices may be unsuitable for disconnecting the components.

Once a modular prosthesis, for example, a modular hip stem prosthesis, has its relative components positioned properly, the components must be firmly secured to each other. It is possible when the components are secured together that relative motion between the components may occur causing their relative position in particular their angular orientation to be disturbed. In other words, when the first and second components of the modular hip stem are drawn together, one component may rotate about the other one causing their version or orientation to be compromised. Further, whatever device that is used to angularly position the components of the modular prosthesis into the proper orientation may need to be removed and an assembly device positioned on the prosthesis to secure the components to each other. Such removal of the alignment device and installation of the assembly device adds cost and complexity to the procedure, as well as, increasing the operating room time.

There is thus a need to provide for an assembly and disassembly tool capable of alleviating at least some of the aforementioned problems.

U.S. patent application Ser. No. 10/327,187 entitled "ADJUSTABLE BIOMECHANICAL TEMPLATING & RESECTION INSTRUMENT AND ASSOCIATED METHOD", U.S. patent application Ser. No. 10/327,196 entitled "ALIGNMENT DEVICE FOR MODULAR IMPLANTS AND METHOD", U.S. patent application Ser. No. 10/327,527 entitled "INSTRUMENT AND ASSOCIATED METHOD OF TRIALING FOR MODULAR HIP STEMS", U.S. patent application Ser. No. 10/606,303 filed Jun. 25, 2003 entitled "MODULAR TAPERED REAMER FOR BONE PREPARATION AND ASSOCIATED METHOD", and U.S. patent application Ser. No. 10/606,304 filed Jun. 25, 2003 entitled "NON-LINEAR REAMER FOR BONE PREPARATION AND ASSOCIATED METHOD" are hereby incorporated in their entireties by reference.

SUMMARY

According to the present invention, a device is provided for two components of a modular joint prosthesis. The device is particularly well-suited for assembling the proximal stem component to the distal stem component of a modular prosthetic joint stem, such as one for a hip prosthesis. The instrument has a portion that engages, for example, the proximal component and another component that engages the distal component. The instrument applies force on the proximal component and an opposing force on the distal component. For example, the instrument may threadably engage the proximal aspect of the distal stem and apply an opposing force on the proximal shoulder of the proximal body.

The first component of the instrument is caused to rotate with respect to the second component of the instrument. A handle is rotated about the central axis that conveys rotary motion into axial displacement. The axial displacement serves to thereby lock and unlock the taper joining the distal component to the proximal component. The instrument may be designed to yield a specific axial displacement, which is previously determined based upon the specific taper geometry of the implant.

In an embodiment of the present invention, a coupling device threadably engages with the proximal aspect of the distal stem. A counterface contacts the proximal aspect or shoulder of the proximal body in order to provide opposing forces, which axially displace the two components relative to each other, thus locking and unlocking the tapered connection. The instrument may be actuated by rotating one handle with respect to the body or another handle. The handle may, for example, travel in a slot, angled relative to the axis of the cylinder, thereby providing axial motion. In other embodiments of the present invention, a standard thread and bolt connection between the first component and the second component provide for the axial motion.

According to the present invention, an instrument is provided that engages and disengages in components of prosthesis by applying opposing forces while offering rotational control to the components. The instrument and associated method can be used for assembly, disassembling, and controlling the version of a modular joint replacement.

The instrument may, for example, threadably engage the proximal aspect of the distal stem and apply an opposing force on the proximal shoulder of the proximal body to assemble or disassemble the components. The instruments may also lock onto the proximal component to control version of the components during assembly.

The instrument may threadably engage the proximal aspect of the distal stem. A counterface, for example, may contact the proximal aspect of the shoulder and an orientation device in the form of a crab claw type of clamp may be used to orient the proximal portion of the body. The instruments provides opposing forces, which axially displaces the two components relative to each other thus locking and unlocking the tapered connection of the modular joint.

The orientation device and the instruments may be used to provide a method to control the rotation and or the position of the proximal body with respect to the distal stem during assembly. The instrument may be actuated by a rotating handle. The handle may for example, travel in a slot angled relative to the axis of the body of the instrument. The instrument may include indicia or marks that can assist in the proper angular orientation of the modular components. External data for example, CT data can be used to reproduce a predetermined angle selected by the surgeon for the prosthesis.

According to one embodiment of the present invention, there is provided an assembly tool for assembly of a first component of a prosthesis to a second component of the prosthesis for use in joint arthroplasty. The tool includes a first member operably associated with the first component and a second member. The second member is operably associated with the second component. At least one of the first member and the second member are adapted to provide for the assembly of the first component of the prosthesis to the second component of the prosthesis. The second member is operably associated with the first member for relative motion between the first member and the second member for assembly of the first component of the prosthesis to the second component. The tool also includes an angular orientation feature cooperating with at least one of the first member and the second member for at least one of replicating and measuring the relative angular orientation of the first component with respect to the second component.

According to another embodiment of the present invention there is provided a kit for use in joint arthroplasty. The kit includes an implant for implantation at least partially in the medullary canal of a long bone. The implant includes a first component and a second component removably attachable to the first component and an assembly tool. The assembly tool has a first member operably associated with the first component. The first member includes a first member relative motion feature and a body defining a generally cylindrical longitudinal opening therein. A second member is operably associated with the second component. The second member is operably associated with the first member for relative motion between the first member and the second member for assembly of the first component of the prosthesis to the second component. The assembly tool also includes an angular orientation feature cooperating with at least one of the first member and the second member for at least one of replicating and measuring the relative angular orientation of the first component with respect to the second component.

According to a further embodiment of the present invention, there is provided a method for providing joint arthroplasty. The method includes the step of providing a prosthesis including a first component and a second component removably attachable to the first component. The method also includes the step of providing an instrument having a first member operably associated with the first component. The first member includes a first member relative motion feature and a body defining a generally cylindrical longitudinal opening therein. A second member is operably associated with the second component. The second member is operably associated with the first member for relative motion between the first member and the second member for assembly of the first component of the prosthesis to the second component. The instrument also includes an angular orientation feature cooperating with at least one of the first member and the second member for at least one of replicating and measuring the relative angular orientation of the first component with respect to the second component. The method also includes the step of assembling the first component to the second component. The method also includes the step of connecting the first member of the tool to the first component. The method also includes the step of connecting the second member of the tool to the second component. The method also includes the step of rotating the first member of the tool with respect to the second member of the tool to secure the first component to the second component.

According to a yet another embodiment of the present invention, there is provided a method for providing joint arthroplasty. The method includes the step of providing a trial prosthesis including a stem trial portion for implantation at least partially into the femoral canal of a femur and a neck trial portion extending from the stem portion. The method includes the steps of positioning the stem trial portion in the femoral canal and positioning the neck trial portion relative to the stem trial portion. The method includes the steps of securing the neck trial portion to the stem trial portion and trialing the trial prosthesis. The method includes the steps of attaching an instrument to the stem trial portion and the neck trial portion and measuring the relative position of the stem trial portion to the neck trial portion. The method includes the steps of providing a implant prosthesis including a stem implant portion for implantation at least partially into the femoral canal of a femur and a neck implant portion extending from the stem portion and of providing an instrument to secure the stem implant portion to the neck implant portion while angularly orienting the stem implant portion to the neck implant portion.

The technical advantages of the present invention include the ability of the device to provide sufficient mechanical advantage to properly secure the components to form a secured joint. For example, according to one aspect of the present invention, the first component is joined to the second component by a threaded connection. By changing the pitch of the threadable connection, the mechanical advantage can be increased to provide for a sufficient mechanical advantage.

For example, according to yet another aspect of the present invention, the first component and the second component have outwardly extending handles. The handles may have any suitable length and may be made longer to provide for additional mechanical advantage. Thus the present invention provides for sufficient mechanical advantage to properly secure the prosthesis.

Another technical advantage of the present invention is the ability of the device to provide for optimum ergonomics. For example, according to one aspect of the present invention, the device is held and actuated by opposed extending handles, which may be easily gripped by the surgeon and rotated relative to each other to secure the joint. Thus, the present invention provides for simple optimum ergonomics.

Yet another technical advantage of the present invention includes the ability of the device to provide for a measurement of forces in addition to the measurement of displacement. Due to frictional forces and additional complications, displacements of the device do not always directly linearly correspond to the forces that may be applied by the device. Therefore, there is an advantage to be able to measure the force applied by the device in addition to the displacement of the device. For example, according to another aspect of the present invention, a handle of the device may include a torque measuring feature, which may be used to measure the torque applied to the device. Alternatively or in addition thereto, the device may include a force washer or other force transducers along the axial body of the instrument in order that the forces applied may be directly measured.

Another technical advantage of the present invention includes the ability of the device to limit the displacement of the instrument and therefore to limit the force applied to the prosthesis. If excessive force is applied to the prosthesis it is possible to overtighten and damage the component. For example, according to one aspect of the present invention, the displacement is physically limited by a helical opening of limited length or by a limited amount of threaded engagement between the two components. It is also possible to provide for a device with a break-away torque limiter that limits the amount of torque that the device may apply. Thus, the present invention provides for an ability to avoid overtightening of the prosthesis components.

Another technical advantage of the present invention is its simple and inexpensive design. For example, according to one aspect of the present invention, the device includes a cylindrical tube and a rod, which slidably fits within the cylindrical tube. The tube and rod are threadably connected so that when one component is rotated with respect to the other one, the one component moves axially relative to the other one, providing for a simple, inexpensive way of utilizing a device to disassemble or assemble a component.

An additional advantage of the present invention includes the ability of the device to be utilized simply and easily to disconnect as well as to connect the components of a modular prosthesis. For example, according to one aspect of the present invention, a component may be placed onto the assembly device to provide for connecting features to disassemble the device. Thus, the present invention provides for a simple and quick way of being utilized to disassemble as well as to assemble a prosthesis.

Another technical advantage of the present invention, includes the ability of the device to control the orientation of the components while they are being connected. The device serves to maintain the orientation during connection. For example, according to one aspect of the present invention, a first member is provided for operable association with the proximal body and a second member is operably associated with the distal stem. Further an angular orientation feature cooperates with the first member and the second member for containing the angular orientation of the first component with respect to the second component. The present invention provides for an ability to control the orientation of the component while they are being secured to each other.

Another technical advantage of the present invention, is that angular orientation of the components of a modular prosthesis can be aligned angularly and secured to each other with a common device. For example, according to the present invention, an assembly tool is provided including a first member associated with the proximal body and the second member associated with a distal stem. An angular orientation feature is provided which cooperates with the first member and the second member to orient the first component with respect to the second component. Thus the present invention provides for the ability to set the angular orientation and secure the components of the modular prosthesis with a common device.

Yet another technical advantage of the present invention is that it can be used to measure the angular orientation of the distal stem with respect to the proximal body. For example, according to one aspect of the present invention the tool of the present invention includes an angular orientation feature, which cooperates with the first member and the second member to measure the relative angular orientation of the first component with respect to the second component. Thus the present invention provides for the ability to measure the angular orientation of the distal stem with respect to the proximal body.

Yet another technical advantage of the present invention includes the ability of the device to limit the force on the joint connection during assembly. For example, according to one aspect of the present invention the first member or the second member of the assembly tool is adapted to provide for limited predetermined amount of relative motion of the first member with respect to the second member along the second member longitudinal axis. Thus the present invention provides for the ability to avoid over-tightening of the prosthesis components.

Yet another technical advantage of the present invention, includes the ability of the device to monitor force or displacement at the connecting joint of the modular prosthesis. For example, according to one aspect of the present invention the assembly tool of the present invention further includes a displacement measuring device or a force measuring device for measuring the displacement or force related to the relative motion of the second member with respect to the first member of the assembly tool. The displacement measuring device and the force measuring device may be utilized to limit the displacement of the force or by preventing the over-tightening of the prosthesis components. The displacement measuring device may be in the form of marks or indicia at the force measuring device may be in the form of a torque wrench.

Yet another technical advantage of the present invention includes the ability of the device to permit the engagement of the distal stem to the proximal body while the proximal body is contacted to the assembly tool. For example, according to one aspect of the present invention the assembly tool further includes a fourth member which is cooperable with the third member. The fourth member translates along the longitudinal axis while the third member translates along the longitudinal axis. The fourth member may be manually rotated about the fourth member longitudinal axis. Thus the fourth member serves to permit manual rotation of the second member to engage the second member to the distal stem to the proximal body manually. Thus the present invention provides for the ability to assemble the tool to the distal stem while the proximal body is connected to the assembly tool.

Yet another technical advantage of the present invention includes the ability of the device to accommodate a plurality of proximal bodies and distal stem lengths. For example, according to one aspect of the present invention, a first member is axially adjustable along the first member axis to accommodate a different length of the first member and the second member. This variation in length between the first member and the second member provides for a fit to a plurality of proximal bodies and distal stems. Thus, the present invention provides for the ability to accommodate a plurality of proximal bodies and distal stems.

Yet another technical advantage of the present invention includes the ability of the device to fit a plurality of proximal bodies and distal stem shape. For example, according to one aspect of the present invention the orientor which orients the first member is slideably connected to the first member. Thus the present invention provides for an ability for the proximal body to move axially with respect of the distal stem providing for a fit of a plurality of different shape proximal bodies and distal stems with a common assembly tool.

Yet another technical advantage of the present invention includes the ability of the device to set the proximal body and distal stem orientation to a desired setting. For example, according to one aspect of the present invention, the assembly tool includes a first orientor that is connected to the first component and a second orientor that cooperates with the second component as well as a first timing feature that cooperates with the first member and a second timing feature that cooperates with the second member. The timing features and orientors can be utilized to pre-set the proximal body and distal stem to a desired setting.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 32 is an exploded plan view of an articulating reamer and a counterbored reamer for use to prepare a cavity in a long bone for the insertion of an implant that may be assembled with the assembly tool of the present invention;

FIG. 71 is a flow chart of a method of using the assembly tool of the present invention according to yet another embodiment of the present invention;

FIG. 72 is a flow chart of another method of using the assembly tool of the present invention according to yet another embodiment of the present invention;

FIG. 74 is a plan view of a proximal body implant/arcuate distal stem implant assembly in cooperation with an assembly tool according to yet another embodiment of the present invention showing an assembly tool internally and externally threaded components;

FIG. 74B is a top view of FIG. 74 showing an alignment feature in greater detail;

DETAILED DESCRIPTION

Embodiments of the present invention and the advantages thereof are best understood by referring to the following descriptions and drawings, wherein like numerals are used for like and corresponding parts of the drawings.

Figure 1:
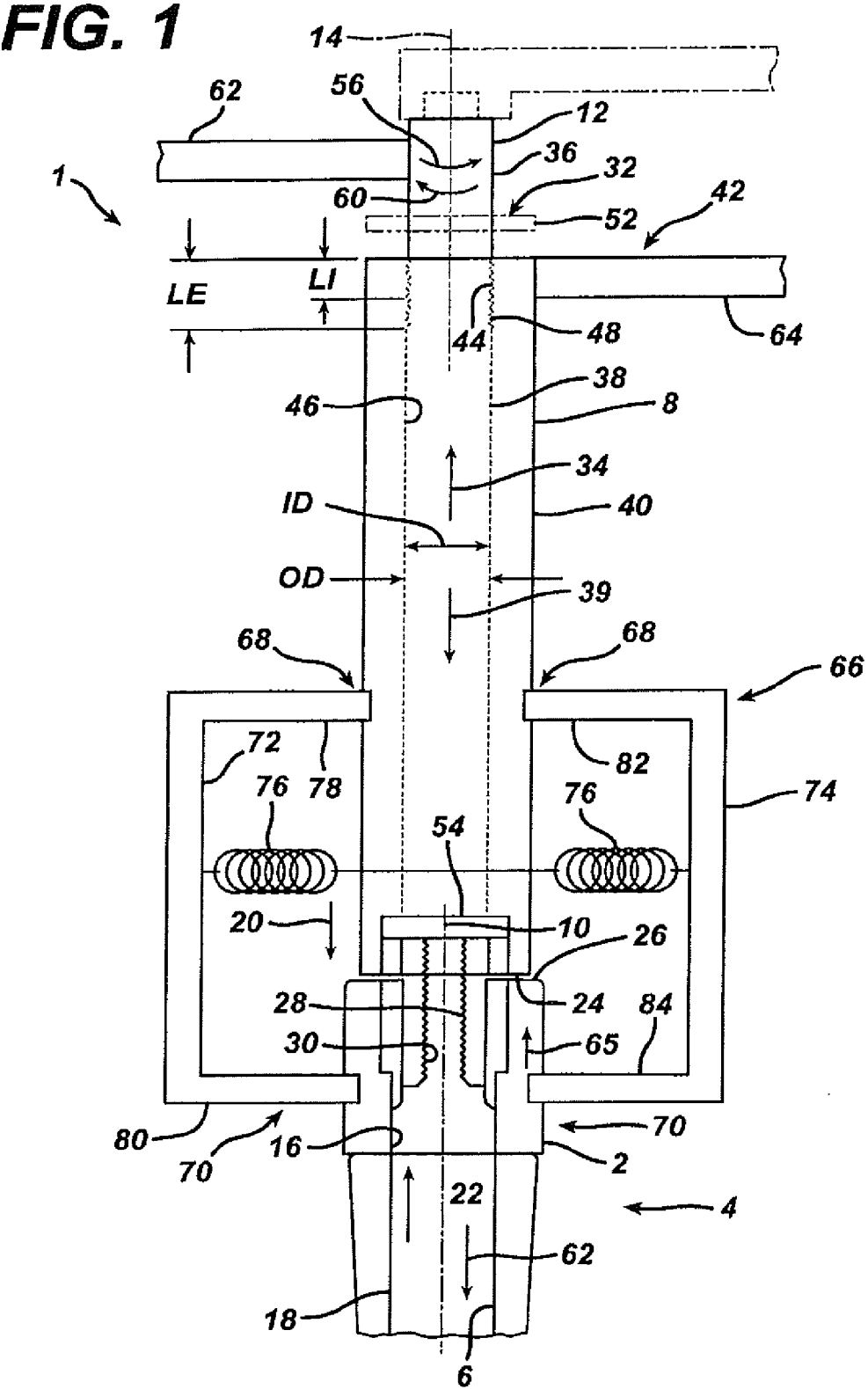
FIG. 1 is a plan view partially in cross-section of an embodiment of the present invention in the form of an assembly tool including a threaded connection in operation with a prosthesis.

According to the present invention and referring now to FIG. 1, assembly tool 1 according to the present invention is shown. The assembly tool 1 is used for assembly of a first component 2 of a prosthesis 4 to a second component 6 of the prosthesis 4 for use in joint arthroplasty. The tool 1 includes a first member 8 operably associated with the second component 6. The first member 8 defines a first member longitudinal axis 10 of the first member 8. The tool 1 also includes a second member 12 operably associated with the second component 6. The second member 12 defines a second member longitudinal axis 14 of the second member 12. The second member 12 is adapted to provide relative motion of the second member 12 with respect to the first member 8 when the second member 12 is rotated relative to the first member 8 about the second member longitudinal axis 14.

The assembly tool 1 is suited for use with the prosthesis 4 when, for example, the prosthesis 4 includes the first component 2 and the second component 6 which are engaged and disengaged by relative motions along an axis. For example, the assembly tool 1 is suitable when the prosthesis 4 includes components, which are connected by a tapered connection.

For example, as shown in FIG. 1, the first component 2 includes an internal taper 16 that mates with an external taper 18 located on the second component 6.

As shown in FIG. 1, the first component 2 is engaged with the second component 6 when the first component 2 moves in the direction of arrow 20 and/or when the second component 6 moves in the direction of arrow 22. As shown in FIG. 1, the first member 8 is operably associated with the first component 2 while the second member 12 is operably associated with the second component 6. To provide for the operable association of the components, it should be appreciated that the first member 8 includes a first member operating feature 24 which is operably associated with a first component operating feature 26 of the first component 2. Similarly, the second member includes a second member operating feature 28 which cooperates with a second component operating feature 30 of the second component 6.

For simplicity, since the first member 8 and the first component 2 are merely required to prevent motion of the two components toward each other, the first member 8 and the first component 2 may be designed such that the first member operating feature 24 may be in the form of a bottom and/or surface. Similarly, the first component operating feature 26 may be in the form of a top surface of the first component 2.

The second member operating feature 28 and the second component operating feature 30 may be any features capable of urging the second component 6 upwardly in the direction of arrow 22. For example, for simplicity, the second member operating feature 28 may be in the form of internal threads formed on the second component operating feature 26, which may mate with external threads 30 formed on the second component 6.

The first member 8 and the second member 12 may have any shape or configuration capable of providing relative motion along first member longitudinal axis 10 and second member longitudinal axis 14. For example, and as shown in FIG. 1, the first member 8 may be in the form of a hollow component or tube. Similarly, the second member 12 may be in the form of a rod or cylinder, which may slidably fit within the first member 8. As shown in FIG. 1, the first member 8 may include a longitudinal opening 32.

In order to move the second component 6 into engagement with the first component 2, it should be appreciated that the second member 12 must move in the direction of arrow 34 with respect to the first member 8. In order to provide relative motion between the second member 12 and the first member 8, as shown in FIG. 1, the second member 12 may include a rod portion 36 having a cylindrical periphery 38 thereof. The first member 8 may, as shown in FIG. 1, include a cylindrical tubular portion 40 that defines the opening 32 therein. The rod periphery 38 of the second member 12 defines an outside diameter OD which is matingly fitted with dimension ID of the opening 32 of the tubular portion 40.

As shown in FIG. 1, the relative motion of the first member 8 with respect to the second member 12 may be controlled by, for example, a relative motion feature 42. As shown in FIG. 1, the relative motion feature 42 may be in the form of a threaded connection. The threaded connection 42 may, for example, as shown in FIG. 1, include a first member relative motion feature 44 in the form, of for, example internal threads. The internal threads 44 are formed on internal periphery 46 of the tubular portion 40 of the first member 8.

The relative motion feature 42 may also include a second member relative motion feature 48. Second member relative motion feature 48 may be in the form of, for example, external threads formed on rod portion 36 of the second member 12. The threads 44 and 48 cooperate to provide the relative motion of the second member 12 in the direction of arrow 34 with respect to the first member 8. The threads 44 and 48 are matingly engaged and have a pitch selected to provide for the desired mechanical advantage.

Preferably and as shown in FIG. 1, the amount of relative motion of the first member 8 with respect to the second member 12 is limited. Such a limited relative motion of the first member 8 with respect to the second member 12 correspondingly limits the motion of the first component with respect to the second component 6 thus preventing over-tightening of the prosthesis 4. The motion of the first member 8 with respect to the second member 12 may be accomplished in any suitable fashion. For example, the external threads 48 may have a thread length LE which is slightly greater than the thread length LI of the internal threads 44 of the first member 8. Thus, the motion in the direction of arrows 34 and 38 of the component 12 with respect to component 8 is limited by the difference of the thread lengths LE and LI. It should be appreciated that the threads 44 and 46 may only limit the motion of the members 8 and 12 if the major diameters of the threads 44 and 48 provide interference with the first member 8 or the second member 12. It should be appreciated that stops (not shown) may be utilized to limit the relative motion of the first member 8 with respect to the second member 12. A cap 52 and a collar 54, both secured to first meter 8 and both shown in phantom, may be utilized to limit the relative motion of the first member 8 with respect to the second member 12.

It should be appreciated that in order to move the second member 12 in the direction of arrow 34 with respect to the first member 8, the second member 12 must be rotated in the direction of arrow 56 with respect to first member 8. This motion assembles the components 2 and 6. Similarly, it should be appreciated that in order for the second member 12 to move in the direction of arrow 39 with respect to the first member 8, the second member 12 must be rotated in the direction of arrow 60 with respect to the first member 8. This motion disassembles the components 2 and 6.

To provide the sufficient torque or mechanical advantage for rotating the second member 12 in the direction of arrow 56 and 60, it should be appreciated that the second member 12 may include a second member handle 62 extending outwardly from the rod portion 36 of the second member 12. Similarly, it should be appreciated that to resist the force applied by the second member handle 62, the first member 8 may similarly include a first member handle 64 extending outwardly from the tubular portion 40 of the first member 8. The handles 62 and 64 may have any suitable size and shape capable of receiving for example the hands of the surgeon or operator of the assembly tool 1.

It should be appreciated that the assembly tool 1 may likewise be utilized to disassemble the first component 2 from the second component 6. It should be appreciated that the assembly tool 1 may be adapted for use for the disassembly of the first component 2 from the second component 6. It should be appreciated that one of the first member 8 and the second member 12 may be associated with one of the first component 2 and the second component 6 such that as the first member 8 is moved relative to the second member 12, the first component 2 may be disassembled from the second component 6. To accomplish this, one of the first member 8 and the second member 12 is operably associated with the first component 2 while the other of the first member 8 and the second member 12 is operably associated with the second component 6.

For example, and as shown in FIG. 1, the second member 12 may be operably associated with the second component 6 by, for example, utilizing the second member cooperating feature 28 in the form of internal threads to cooperate with the second component operating feature 30 in the form of external threads. The first member 8 is similarly operably associated with the first component 2.

In order that the second component 6 may be forced to move in the direction of arrow 63 while the first component 2 is required to move in the direction of arrow 65, the first component 2 must be restrained by the first member 8. The first component 2 is held against the first member 8 by, for example, a third member 66.

The third member 66 cooperates with the first member 8 and the first component 2 to hold the two components against each other. The third member 66 may cooperate with the first member 8 and the first component 2 in any suitable fashion. For example, the first member 8 may include a first member disassembly operating feature 68 which cooperates with the third member 66. Similarly, the first component 2 may include a first component disassembly operating feature 70 which cooperates with the third member 66.

The third member 66 may have any suitable design or shape and may, for example, be in the form of first fork 72 and second fork 74. The forks 72 and 74 may be urged together by, for example, springs 76. The first fork 72 may include a first tine 78 which engages with the first member disassembly operating feature 68 in the form of, for example, a first member groove. Similarly, the first fork 72 may include a second tine 80 for cooperation with the first component operating disassembly feature 70 in the form of, for example, a second component groove. The second fork 74 may include a first tine 82 for cooperation with the first member groove 68 as well as a second tine 84 for engagement with the second groove 70.

When utilizing the assembly tool 1 to assemble the first component 2 to the second component 6 the third member 66 is not used. The assembly tool 1 is positioned with respect to the prosthesis 4 such that the internal threads 28 of the second member 12 engage the external threads 30 of the second component 6. The internal threads 28 and the external threads 30 are threaded into engagement with each other and the second member 12 is rotated with respect to the second component 6 until the bottom end surface 24 of the first member 8 is in contact with the top surface 26 of the first component 2. At this point, the second member handle 62 is rotated in the direction of arrow 56 until the second member handle has come to the stop created by the relative motion feature 42.

When utilizing the assembly tool 1 to disassemble the first component 2 from the second component 6 the third member 66 is utilized and placed in position on the assembly tool 1. The forks 72 and 74 of the third member 66 are placed in position in the first member grooves 68 and the first component grooves 70. The top surface 26 of the first component 2 is thus in contact with the bottom end surface 24 of the first member 8. The second component 6 is then threadably engaged into the second member 12. The second member handle 62 is then rotated in the direction of arrow 60 until the relative motion feature 42 ends the movement of the second member handle 62 thereby disassembling the first component 2 from the second component 6.

Figure 2:
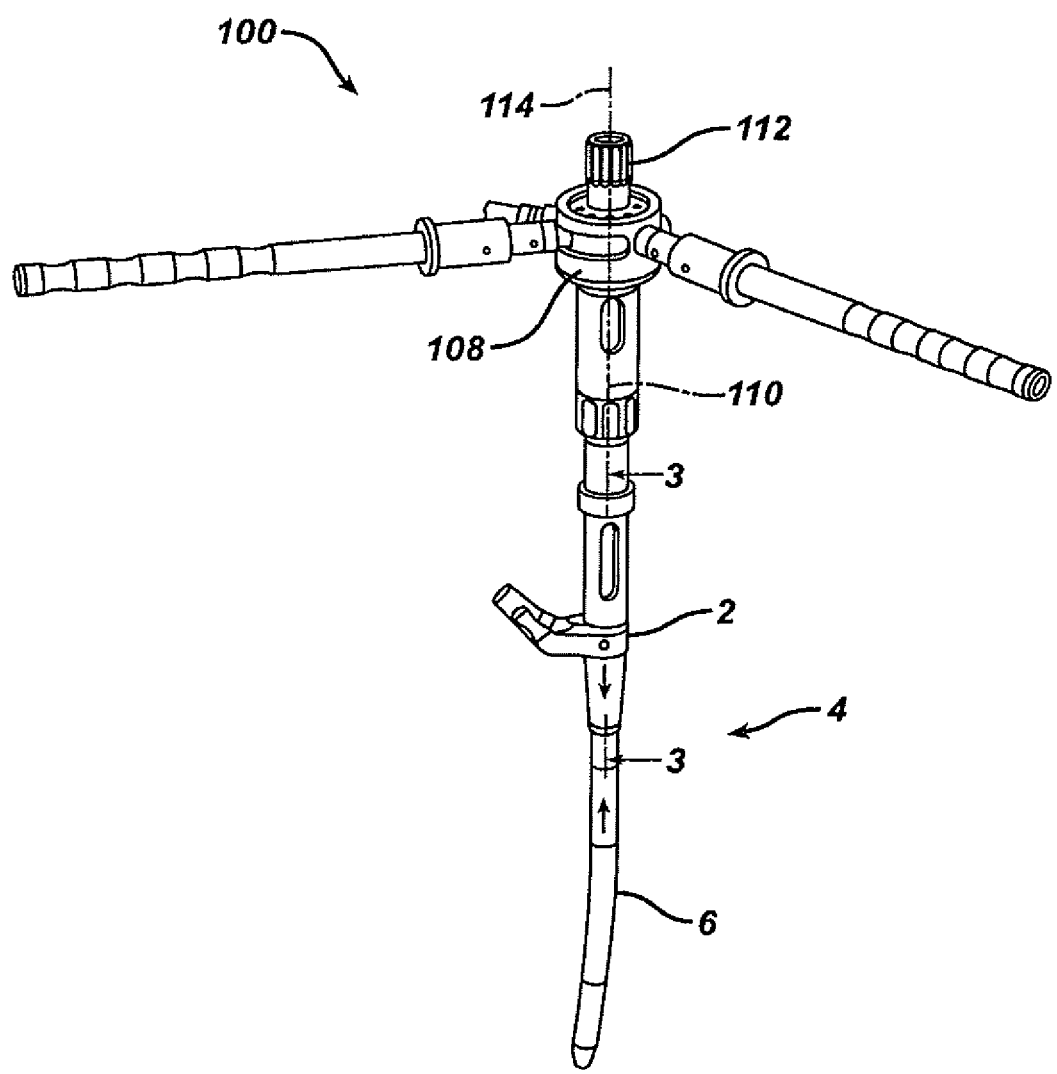
FIG. 2 is a perspective view of another embodiment of the present invention in the form of an assembly tool with a spiral cam and follower mechanism shown in engagement with a prosthesis.

Referring now to FIG. 2, another embodiment of the present invention is shown as assembly tool 100. The assembly tool 100 is utilized for assembling the first component 2 of the prosthesis 4 to the second component 6 of the prosthesis 4. The prosthesis 4 may be used, for example, in joint arthroplasty. The tool 100 is similar to the tool 1 of FIG. 1 and includes a first member 108 operably associated with the first component 2. The first member 108 defines a first member longitudinal axis 110 thereof. The assembly tool 100 further includes a second member 112 which is operably associated with the second component 6. The second member 112 defines a second member longitudinal axis 114 thereof. The second member 112 is similar to second member 2 of the assembly tool 1 of FIG. 1. The second member 112 is adapted to provide relative motion of the second member 112 with respect to the first member 108 when the second member 112 is rotated relative to the first member 108 about the second member longitudinal axis 114.

The assembly tool 100 may be configured such that the relative motion of the second member 112 with respect to the first member 108 corresponds to the relative motion of the first component 2 with respect to the second component 6 to urge the second component 6 into engagement with the first component 2.

Figure 3:
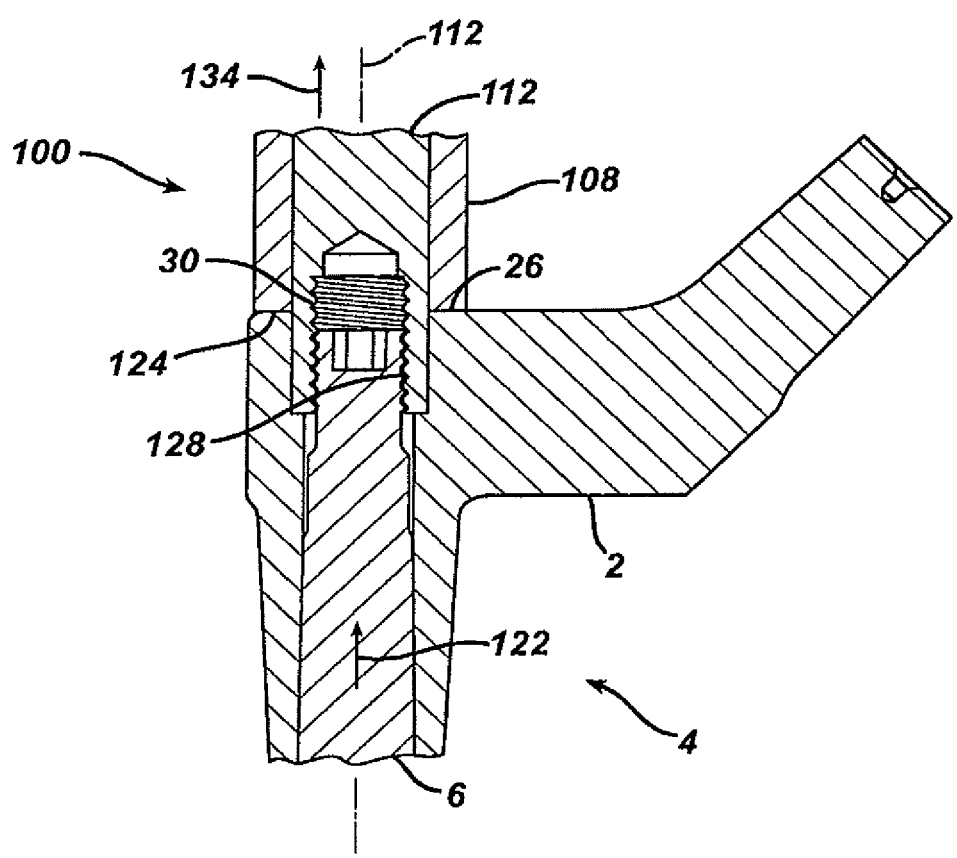
FIG. 3 is a cross section view of FIG. 2 along the line 3-3 in the direction of the arrows.

Referring now to FIG. 3, the engagement of the assembly tool 100 with the prosthesis 4 is shown in greater detail. As shown in FIG. 3, the second component 6 includes a second component operating feature in the form of external threads 30. The external threads 30 are matingly fitted to, for example, internal threads 128 formed on second member 112. The first component 2 includes an operating feature in the form of, for example, a top surface 26 which mates with bottom surface 124 of the first member 108 of the tool 100.

Since the first member 108 is in contact with the first component 2 as the first component moves in the direction of arrow 122 relative to the first component 2, the second member 112, which threadably secured to the second component 6 moves in the direction of arrow 134 relative to the first member 108. Thus, the relative motion of the second member 112 with respect to the first member 108 in the direction of arrow 134 corresponds to the relative motion of the second component 6 with respect to the first component 2 in the direction of arrow 122.

Figure 4:
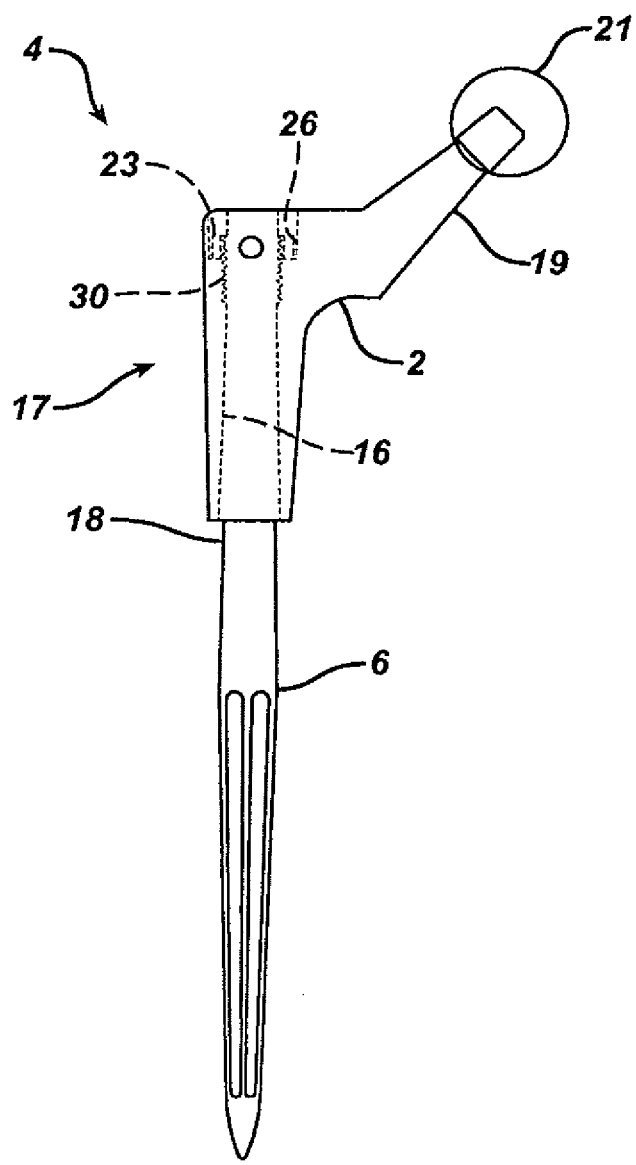
FIG. 4 is a plan view of a two pieced modular hip stem than may be assembled with the assembly tool of FIG. 2.

Referring now to FIG. 4, the prosthesis 4 is shown in greater detail. The prosthesis 4 as shown in FIG. 4 includes a taper connection 17. As shown in FIG. 4, the taper connection consists of the external taper 18 formed on the distal stem 6 that engages with internal taper 16 formed on the first component in the form of the proximal body 2.

It should be appreciated that the prosthesis for use with the assembly tool 1 or 100 of FIGS. 1 and 2, respectively, may include a proximal body 2 and a distal stem 6 which have an interference connection that is, for example, a interference connection of a cylindrical bore to a cylindrical stem, as well as, a splined non-uniform cross-section stem to a splined or non-uniform cross-section opening. It should further be appreciated that proximal body and distal stem of the prosthesis 4 for use with the assembly tool of the present invention may include a taper connection in which the distal stem has an internal taper and the proximal body has an external taper.

Again referring to FIG. 4, the prosthesis 4 as shown may include external threads 30 formed on the distal stem 6. The proximal body 2 may include a neck 19 to which a head 21 may matingly be fitted. As an additional precaution in assuring that the proximal body 2 remains secured to the distal stem 6, the prosthesis 4 may further include a nut 23 which threadably engages the external threads 30 of the distal stem 6.

Figure 5:
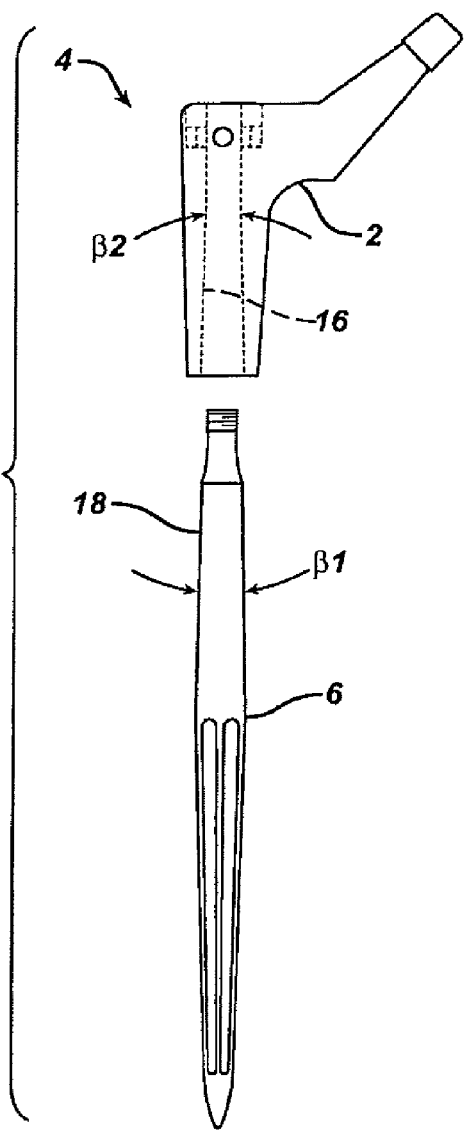
FIG. 5 is an exploded plan view of the modular hip stem of FIG. 4.

Referring now to FIG. 5, the prosthesis 4 is shown with the proximal body 2 disassembled from the distal stem 6. The external taper 18 of the distal stem 6 is defined by an included angle β1. In order that the proximal body 2 fits securely to the distal stem 6, the proximal body 2 includes the internal taper 16 defined by included angle β2. The angles β1 and β2 may be generally the same. Alternatively the taper angle may be divergent. The angles β1 and β2 should be chosen, such that the fit of the proximal body 2 to the distal stem 6 is secure.

Figure 6:
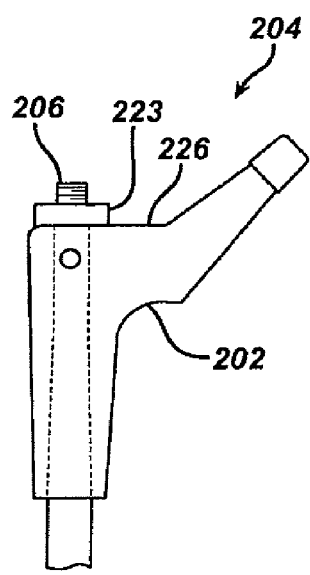
FIG. 6 is a partial plan view of a proximal body of another embodiment of a two pieced modular hip stem than may be assembled with the assembly tool of FIG. 2 without the counter bore for the assembly nut as in the hip stem of FIG. 5.

Referring now to FIG. 6, an alternate prosthesis for use with the assembly device of the present invention is shown as prosthesis 204. Prosthesis 204 includes a proximal body 202 which does not include a counterbore. Prosthesis 204 may include a nut 223 which mates with outer face 226 that is not recessed. The nut 223 threadably engages distal stem 206.

Figure 7:
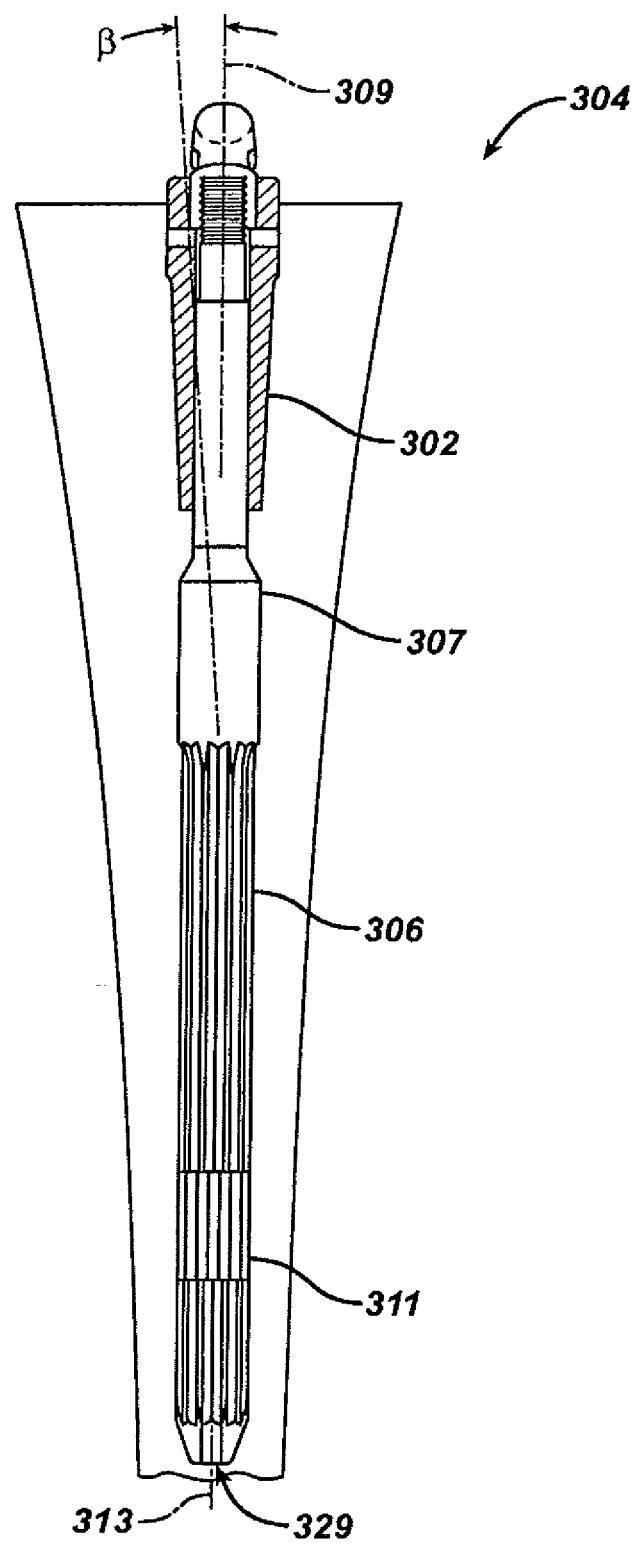
FIG. 7 is a lateral view partially in cross section of the modular hip stem of FIG. 4.

Referring now to FIG. 7, an alternate embodiment of a prosthesis that may be utilized with the assembly tool 1 and 100 of FIGS. 1 and 2, respectively, is shown as prosthesis 304. The prosthesis 304 includes a proximal body 302 similar to the proximal body 2 of the prosthesis 4 of FIG. 4. The prosthesis 304 also includes a distal stem 306 that is different than the distal stem 6 of the prosthesis 4 of FIG. 4. The distal stem 306 is bent and has a proximal portion 307 having a longitudinal centerline 309 and a distal portion having a longitudinal centerline 313. The centerlines 309 and 313 form angle β therebetween. The distal stem 306 may further include an elongated slot 329 extending axially from the end of the stem 306.

Figure 8:
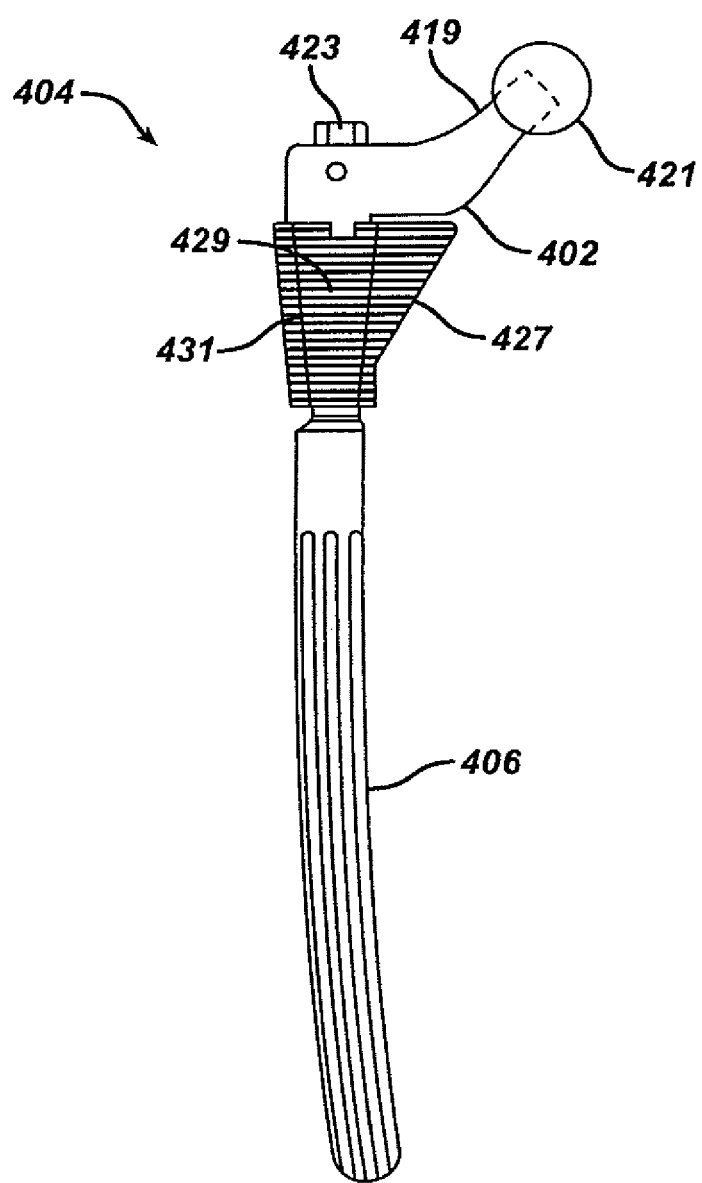
FIG. 8 is a plan view of a three piece modular hip stem with a nut that may be assembled with the assembly tool of FIG. 2.
Figure 9:
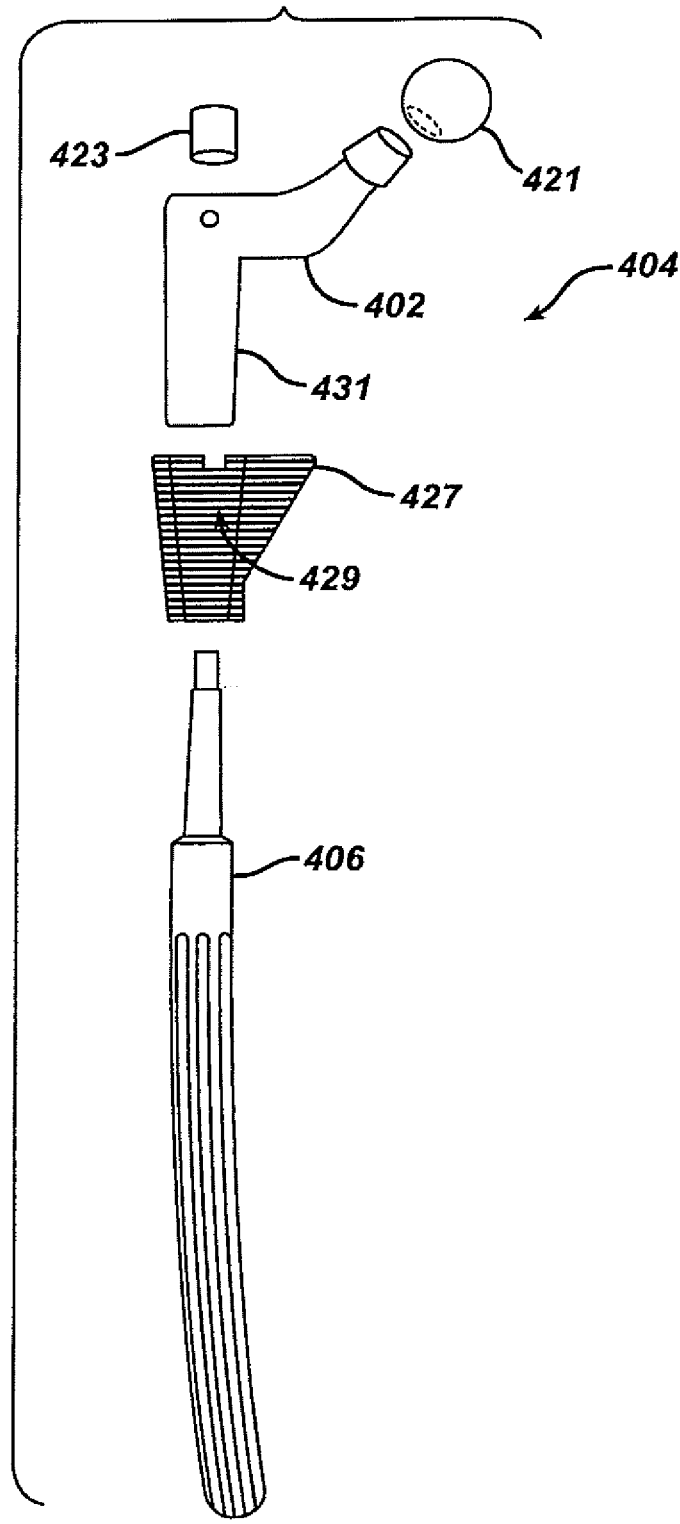
FIG. 9 is an exploded plan view of three piece modular hip stem of FIG. 8.

Referring now to FIGS. 8 and 9, another embodiment of a prosthesis for use with the assembly tool of the present invention is shown as prosthesis 404. Prosthesis 404 is similar to the prosthesis 304 of FIG. 7. Prosthesis 404 includes a proximal body 402 which is connected to a distal stem 406. The proximal body 402 includes a neck 419 to which a head 421 may be positioned. The prosthesis 404 may further include a nut 423 to assist in connecting the proximal body 402 to the distal stem 406. The prosthesis 404 may further include an external sleeve 427 which is fitted to the proximal body 402 by means of an internal taper 429 which mates with an external taper 431 on the proximal body 402. The stem 406 may be bent in a continuous arc.

Figure 10:
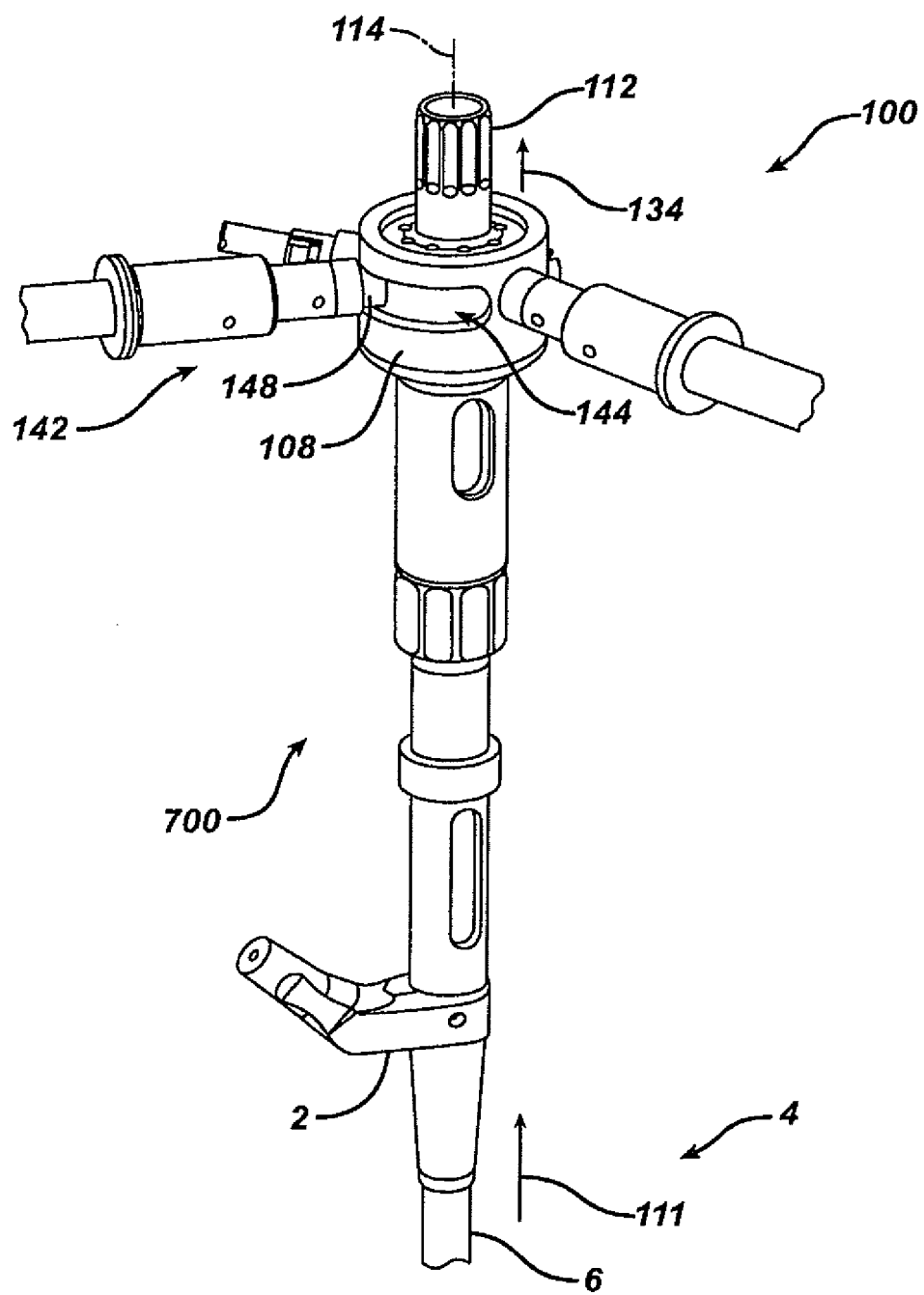
FIG. 10 is a perspective view of the assembly tool of FIG. 2 installed onto the two-piece modular stem of FIG. 4.
Figure 11:
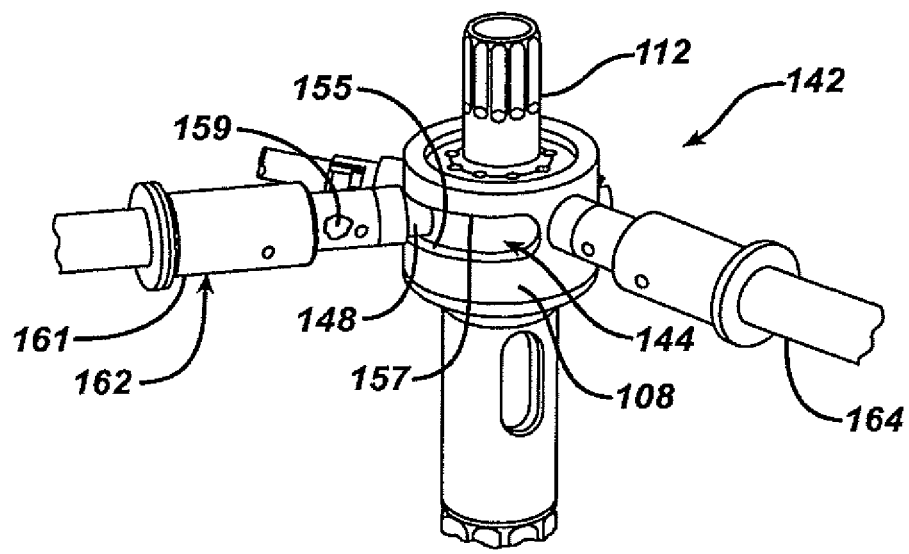
FIG. 11 is a partial perspective view of the assembly tool of FIG. 2 showing the inclined actuating area in greater detail.

Referring now to FIG. 10, the assembly tool 100 is shown in position on the prosthesis 4. The first member 108 is in contact with the first component 2 and the second member 112 is threadably engaged to the second component 6. The assembly tool 100 is utilized to move the second component 6 in the direction of arrow 111 with respect to the first component 2. This relative motion is accomplished by moving the second member 112 in the direction of arrow 134 in relation to the first member 108.

The relative motion of the first member 108 with respect to the second member 112 may be accomplished by, for example, a relative motion feature 142. The relative motion feature 142 may include a first member relative location feature 144 in the form of slot 144 within which a second member relative motion feature 148 in the form of, for example, a pin is rollably restrained with the slot 144. The relative motion feature 142 is utilized to move the second member 112 about the second member longitudinal axis 114 with respect to the first member 108.

Referring now to FIGS. 11, 12, 13, 14 and 15, the relative motion feature 142 is shown in greater detail.

Figure 16:
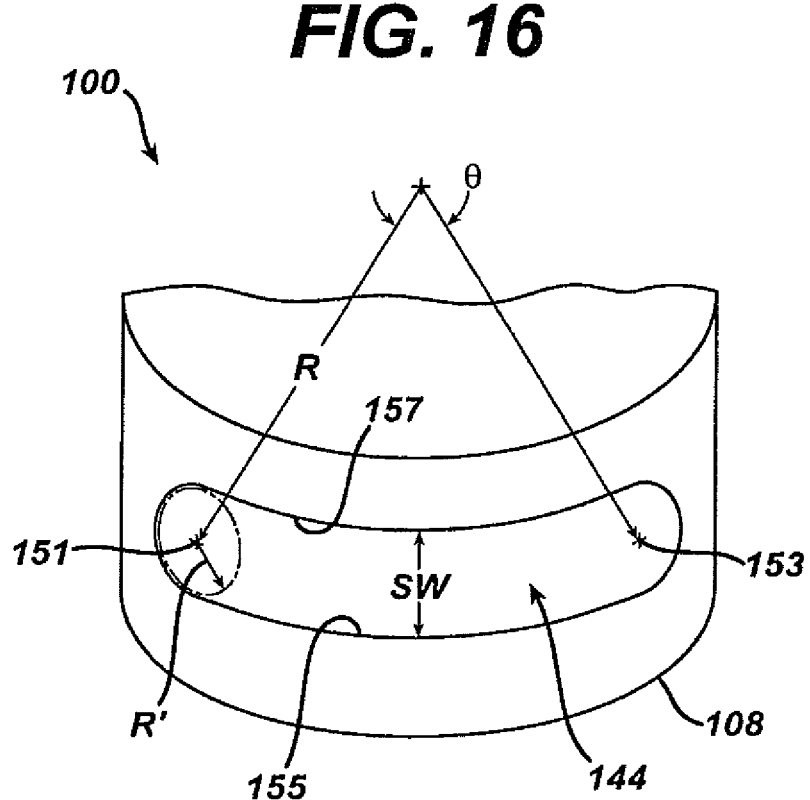
FIG. 16 is a partial perspective view of the assembly tool of FIG. 2 showing spiral cam portion of the ramp actuation mechanism in greater detail.

As shown in FIG. 16, the slot 144 extends from first centerline 151 to second centerline 153. The centerlines 151 and 153 represent the arcuate end portions of the slot 144 defined with a radius R' equal to the slot width SW divided by two. The slot 144 is defined by a first assembly load surface 155 and an opposed second disassembly load surface 157. The load surfaces 155 and 157 are parallel to each other and spaced apart a distance equal to SW or the slot width SW.

A slot length angle θ defines the arcuate difference from first member centerline 110 along slot radius R of the first member 108 between the first centerline 151 and the second centerline 153. The angle θ preferably selected to provide for the proper displacement of the assembly tool 100. The proper displacement of the assembly tool 100 may be predetermined by calculating the desired locking force on the joint of the prosthesis 2.

Figure 12:
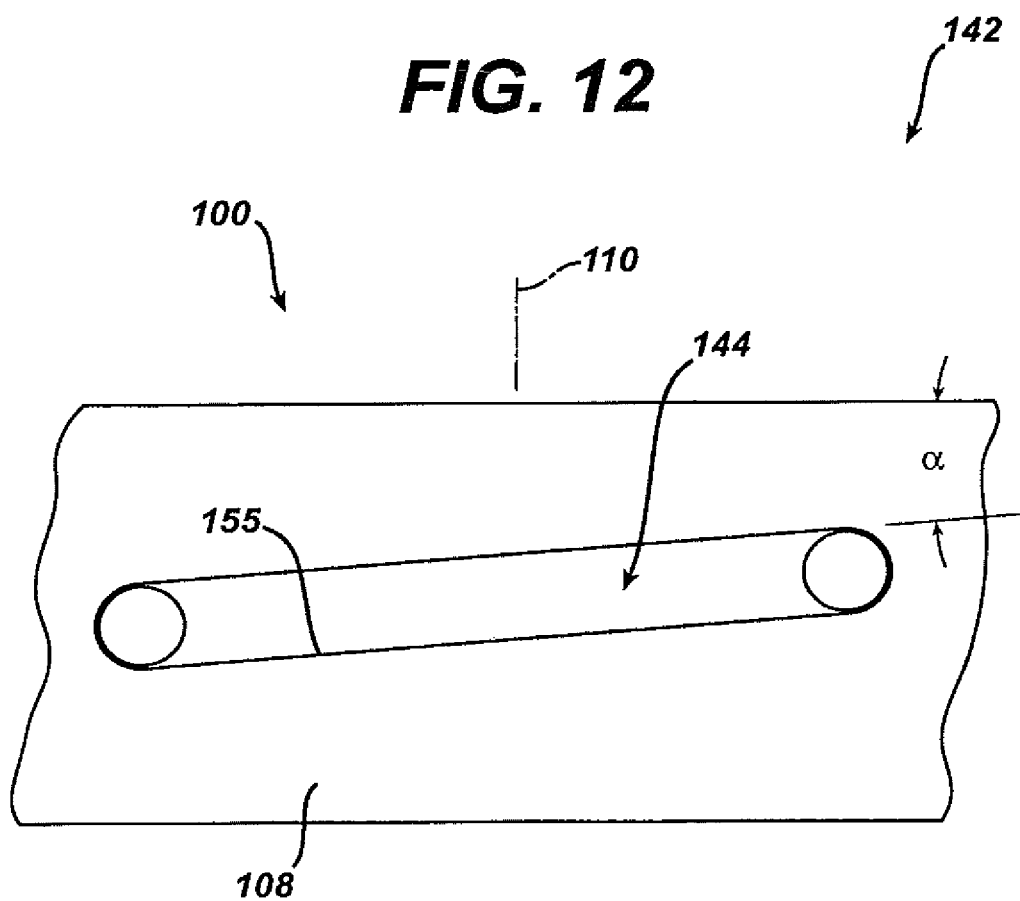
FIG. 12 is a partial unwound view of the inclined actuating area of the assembly tool of FIG. 2 showing the inclined actuating area in greater detail.

Referring to FIG. 12, the assembly load surface 155 is inclined relative to a surface perpendicular to the longitudinal axis 110 of the first member 108 at a ramp angle of α. The angle α, as well as, the radius R (see FIG. 16) affect the displacement of the assembly tool 100.

The dimensions of the relative motion feature 142 may be properly selected by using the formula below:

$$DI = (\theta/360) \times n \times 2R \times \tan \alpha$$

Where:
θ = the angular arm displacement in radians
R = the slot 144 radius from centerline 110 in inches
DI = the displacement in inches.
α = the ramp angle in degrees.

Figure 17:
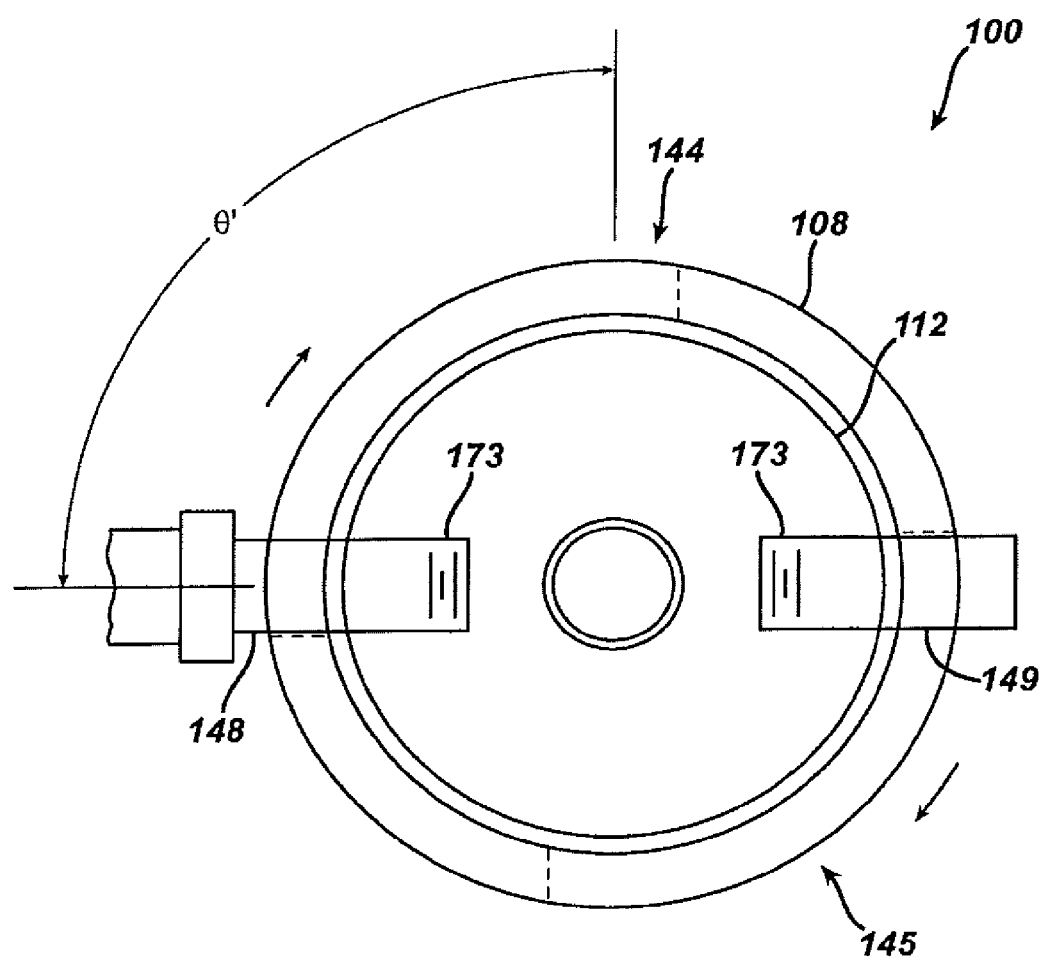
FIG. 17 is a partial top view of the assembly tool of FIG. 2 partially disassembled, showing the spool of the ramp actuation mechanism in greater detail.

Referring now to FIG. 17, the assembly tool 100 may include a second pin 149 opposed to the first pin 148 which matingly fits within a second slot 145 opposed to the first slot 144. First and second pins 148 and 149 are preferably diametrically opposed and the first slot 144 and the second slot 145 are likewise preferably diametrically opposed. The second pin 149 and the second slot 145 serve to balance the forces and loads upon the assembly tool 100.

Referring again to FIG. 11, the assembly tool 100 may include an actuating arm 162 similar to arm 62 of tool 1 of FIG. 1 and a restraining arm 164 similar to arm 64 of tool 1 of FIG. 1. The actuating arm 162 and the restraining arm 164 may be, for example, modular. The arm 162, for example, may include an arm connecting base 159 and an arm extension 161 removably connectable to the arm connecting base 159.

Figure 18:
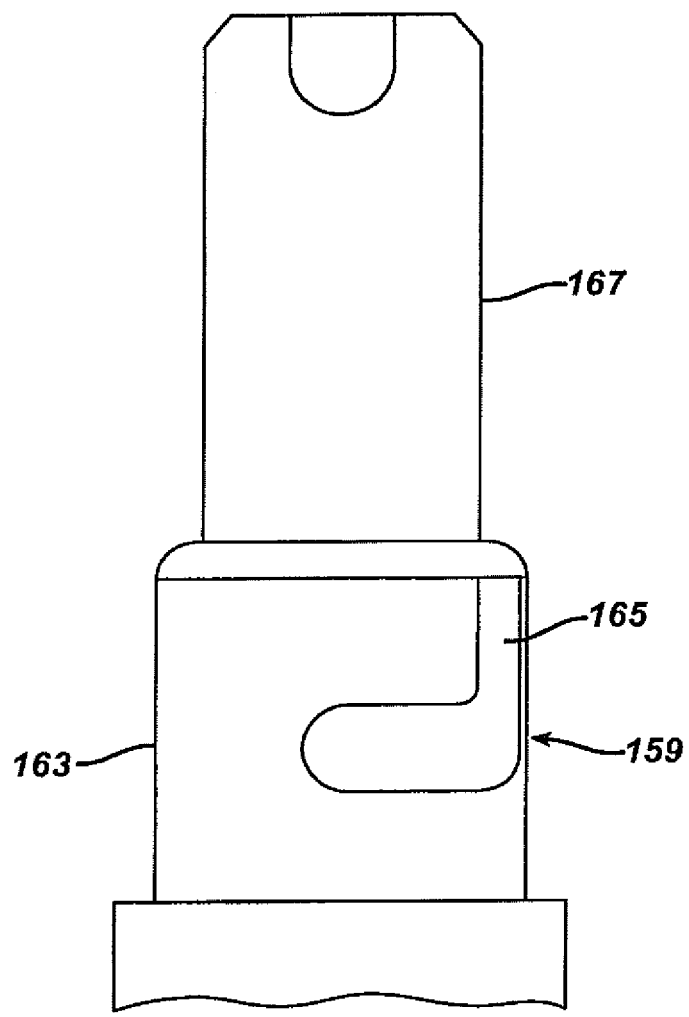
FIG. 18 is a partial enlarged plan view of the assembly tool of FIG. 2 showing the connector for cooperation with the actuation arm in greater detail.

Referring now to FIG. 18, the arm connecting base 159 is shown in greater detail. The arm connecting base 159 includes a base 163 including a bayonet-type groove 165. A stem 167 may extend from the base 163.

Figure 19:
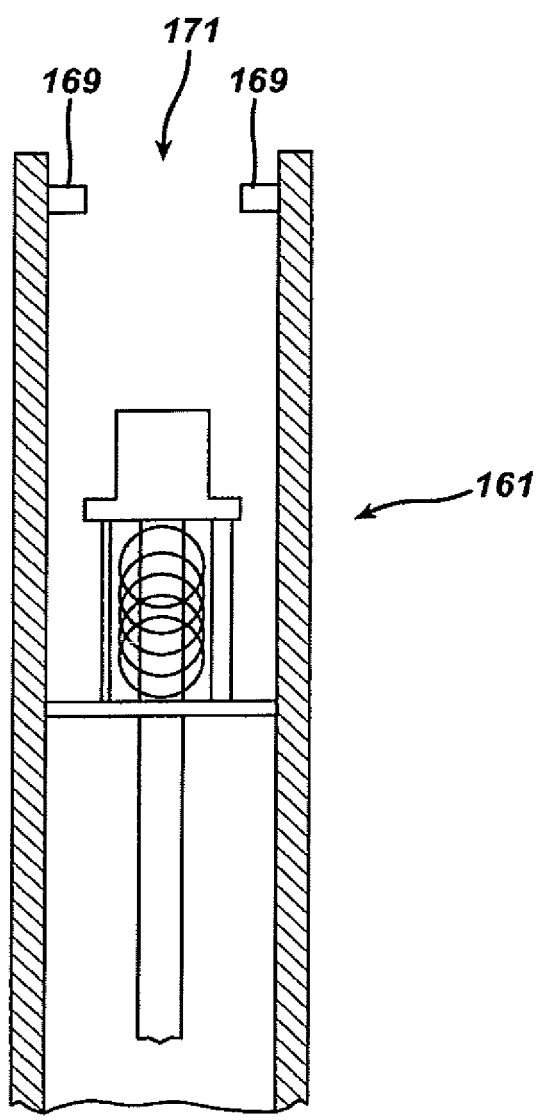
FIG. 19 is a partial enlarged plan view partially in cross section of the assembly tool of FIG. 2 showing the connector of the actuation arm in greater detail.

Referring now to FIG. 19, the arm extension 161 is shown in greater detail. The arm extension 161 may include a pair of pins 169 extending toward the opening 171 in the arm extension 161. The opening 171 receives the base 163 and the stem 167 of the arm connecting base 159 (see FIG. 18).

Referring again to FIG. 17, the construction of the pins 148 and 149 are shown in greater detail. To provide for rolling contact of the pins 148 and 149 against the slots 144 and 145, respectively, the pins 148 and 149 are preferably rotatably mounted on pin stems 173. The pin stems 173 may be threadably connected to the second member 112. It should be appreciated that the pins 148 and 149 may be mounted to the pin stems 173 by means of needle bearings (not shown).

Figure 20:
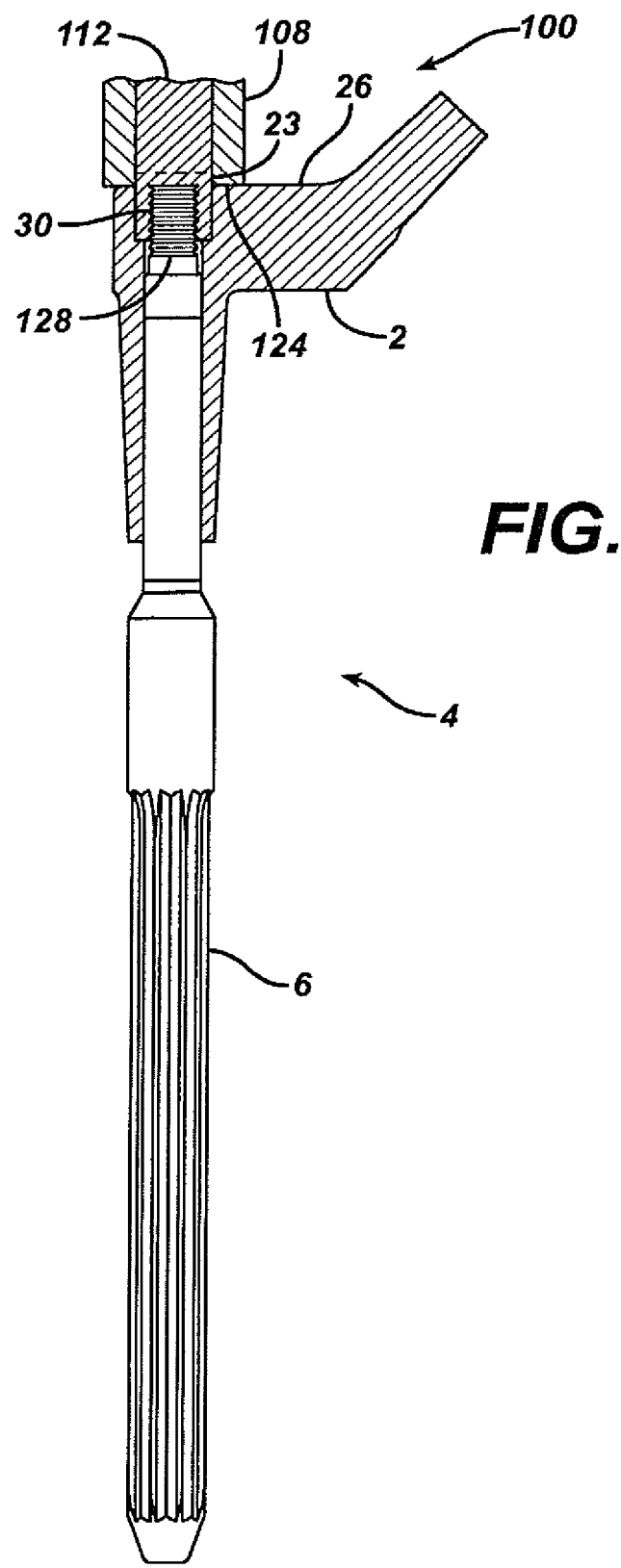
FIG. 20 is a plan view partially in cross section of the implant of FIG. 4 showing the implant in engagement with the assembly tool of FIG. 2.

Referring now to FIG. 20, the prosthesis 4 is shown in engagement with the assembly tool 100. Surface 124 of the first member 108 of the assembly tool 100 is placed against top face 26 of the proximal body 2 of the prosthesis 4. The internal threads 128 of the second member 112 of the assembly tool 100 is threadably engaged with external threads 30 of the stem 6 of the prosthesis 4. After the prosthesis 4 has been assembled utilizing the assembly tool 100, nut 23 shown in phantom is secured to the external threads of the stem 6.

Figure 21:
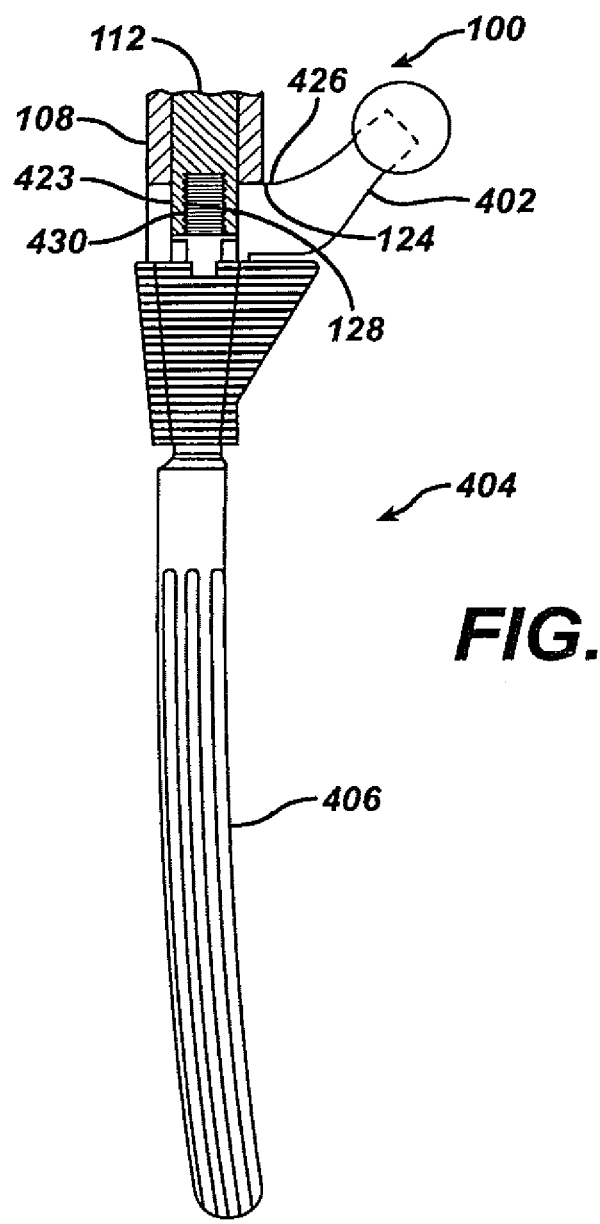
FIG. 21 is a plan view partially in cross section of the implant of FIG. 8 showing the implant in engagement with the assembly tool of FIG. 2.
Figure 22:
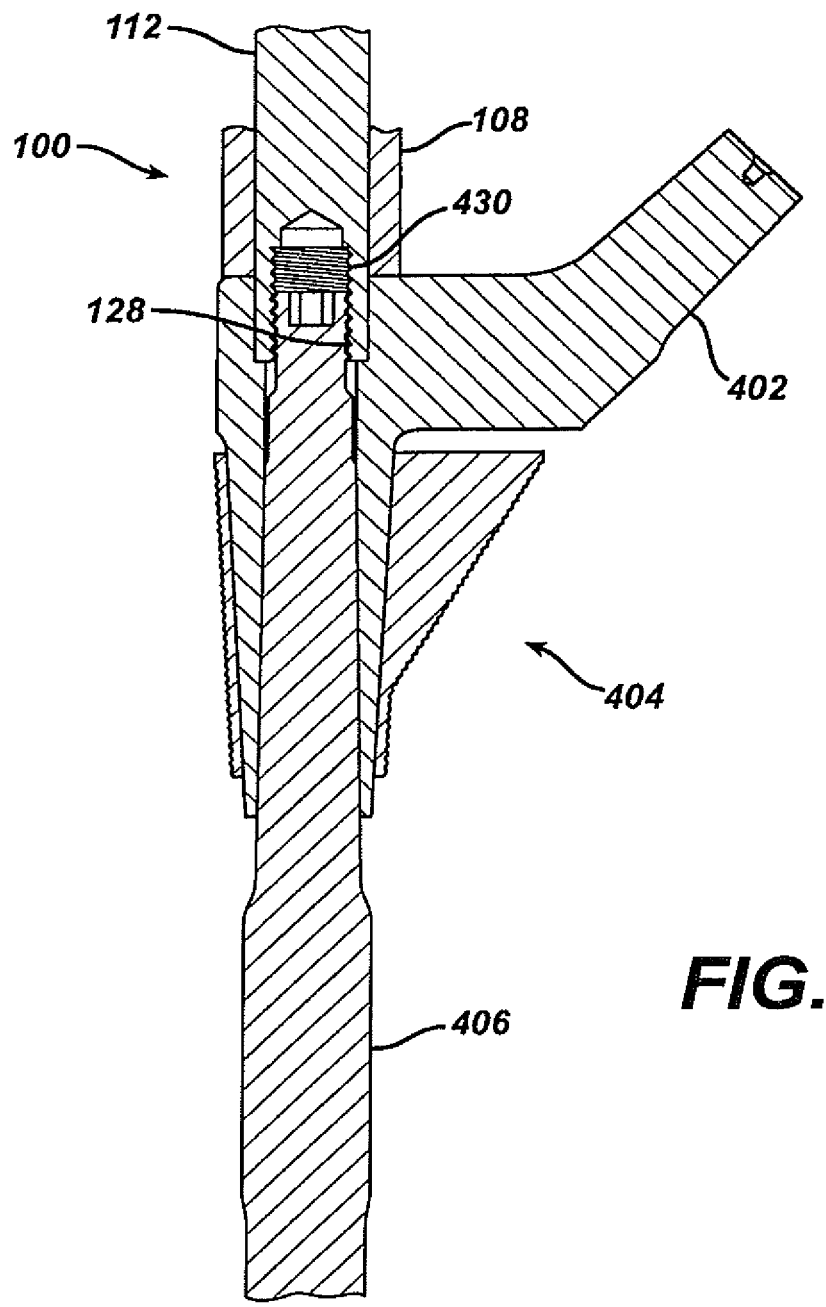
FIG. 22 is a partial enlarged view of the implant of FIG. 8 being assembled with the assembly tool of FIG. 2.

Referring now to FIGS. 21 and 22, the prosthesis 404 is shown in connection with the assembly tool 100. Outer surface 124 of the first member 108 of the assembly tool 100 is placed against top surface 426 of the proximal body 402 of the prosthesis 404. The internal threads 128 of the second member 108 of the assembly tool 100 is threadably engaged with external threads 430 of the distal stem 406. After the prosthesis 404 has been assembled with the assembly tool 100, nut 423 shown in phantom is positioned on the external threads 430 of the distal stem 406.

Referring again to FIG. 13, the assembly tool 100 is shown in greater detail. While the first member 108 and the second member 112 may be made of a one-piece or unitary construction, it should be appreciated that the first member 108 and the second member 112 may be made of multiple components or may be modular. For example, and referring to FIG. 13, the first member 108 may include a sleeve portion 140, having a lower sleeve 186 as well as an upper sleeve 188.

Figure 13:
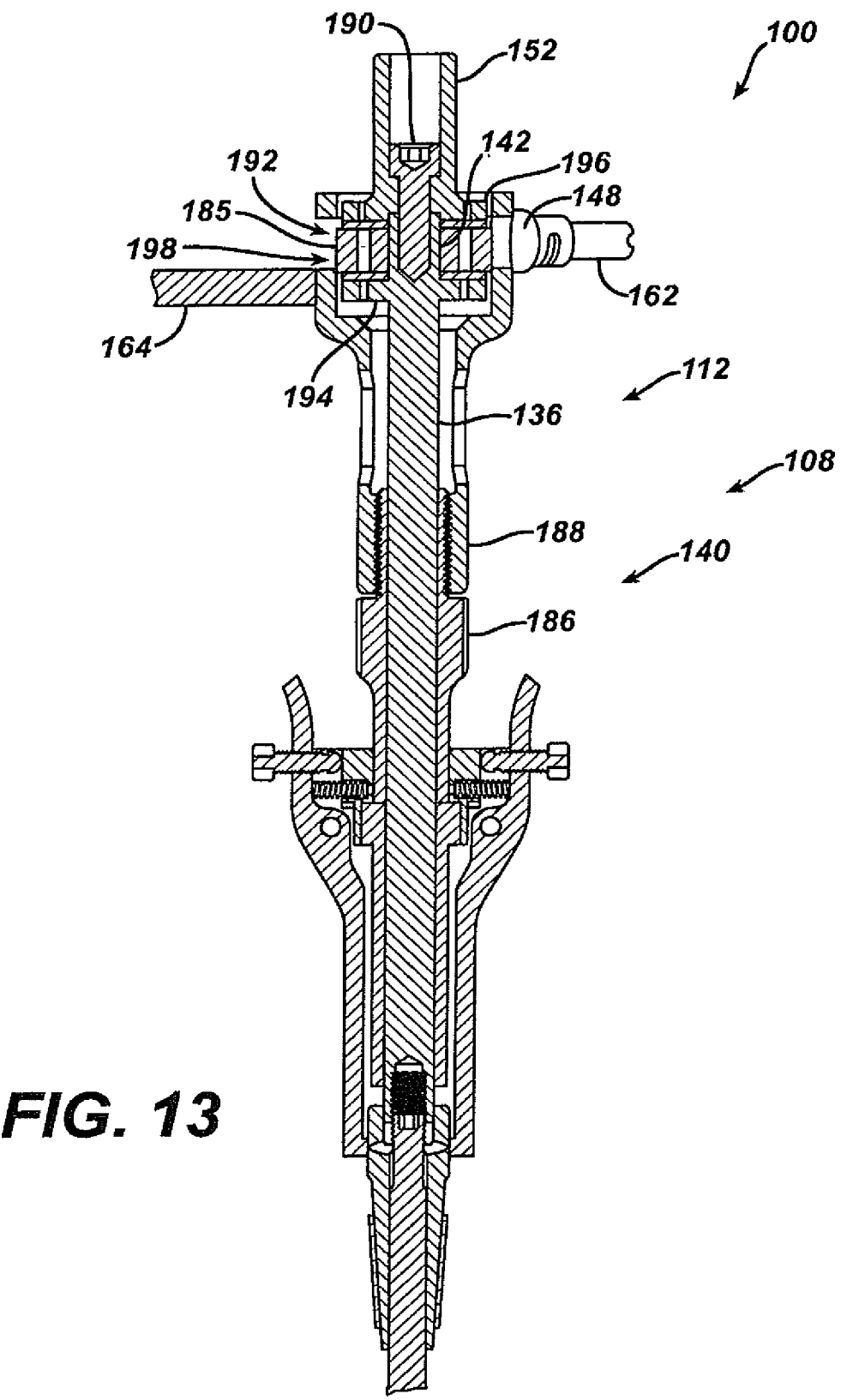
FIG. 13 is a cross-sectional plan view of the assembly tool of FIG. 2 showing the implant of FIG. 8 being disassembled.
Figure 14:
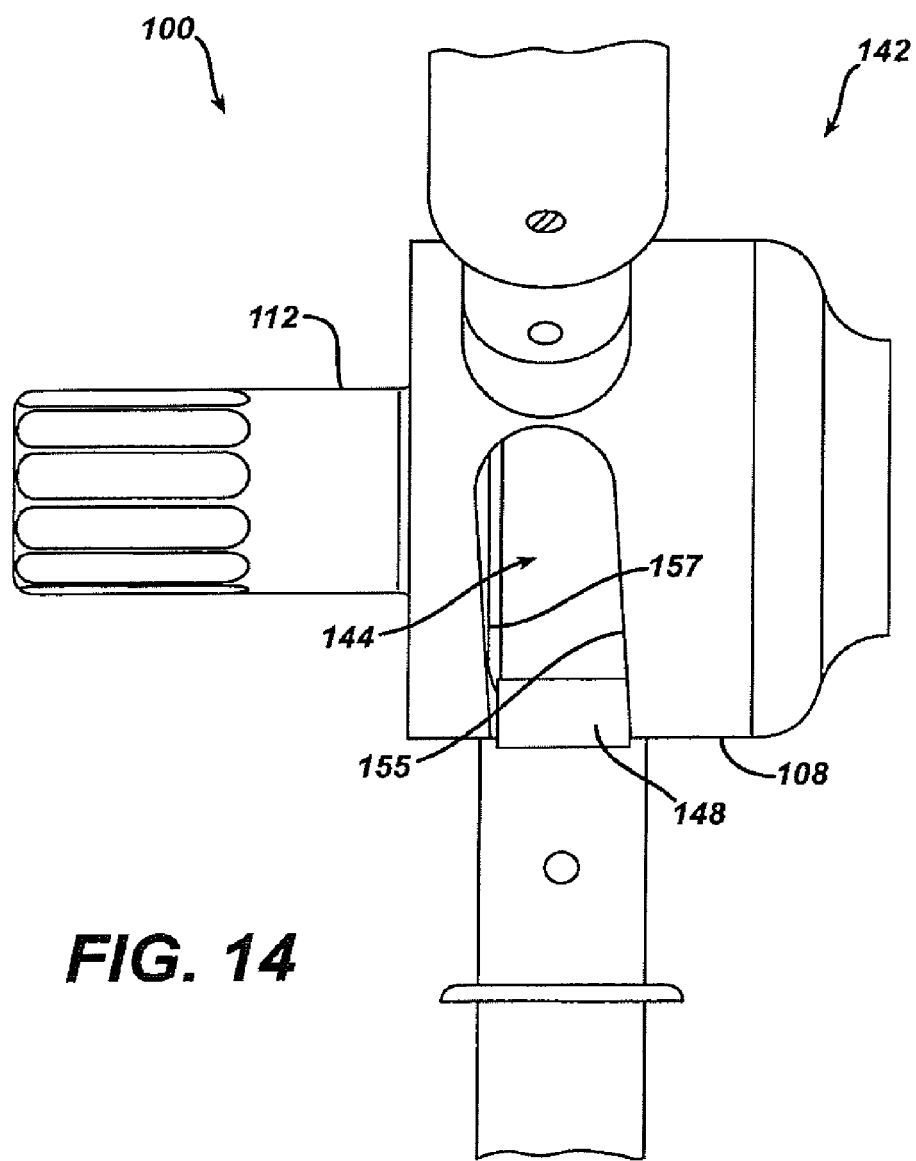
FIG. 14 is a partial enlarged plan view of the assembly tool of FIG. 2 showing the ramp actuation mechanism in greater detail.
Figure 15:
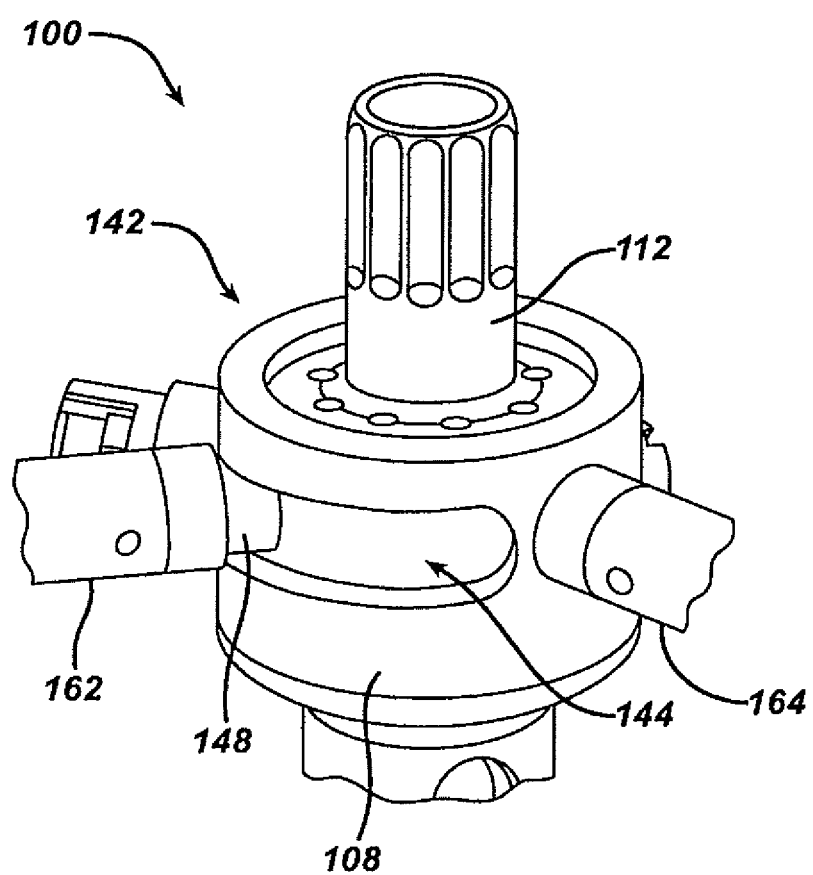
FIG. 15 is a partial enlarged perspective view of the assembly tool of FIG. 2 showing the ramp actuation mechanism in greater detail.

The lower sleeve 186 may be connected to the upper sleeve 188 in any suitable manner, for example, by welding, by press fit, or as shown in FIG. 13, by being threadably connected. The first member 108 may also include a third component in the form of the first member handle 164. The first member handle 164 may be removably connected to the upper sleeve 188 by, for example, a bayonet connection such as that described in FIGS. 18 and 19 herein.

Similarly, the second member 112 may be made of a modular or multi-piece construction. For example, the second member 112 may include a rod portion 136 removably connected to a cap 152. The rod portion 136 may be secured to the cap 152 in any suitable fashion. For example, the cap 152 may be welded to the rod portion 136, or be press fitted thereto. Alternatively, and as shown in FIG. 13, the rod portion 136 may be threadably connected to the cap 152 by means of a screw 190 threadably secured to the rod portion 136 and trapping the cap 152 therebetween. As shown in FIG. 13, the cap 152 and the rod portion 136 cooperate to form a spool 192 therebetween. The spool 192 includes a first retaining portion 194 extending from the rod portion 136 and a spaced-apart and parallel second restraining portion 196. A central portion 198 is positioned between the first restraining portion 194 and the second restraining portion 196.

Continuing to refer to FIG. 13, the second member 112 of the assembly tool 100 further includes a ring 185 rotatably positioned about the central portion 198 of the rod portion 136. The pin 148 is retainably connected to the ring 185. The handle 162 is fixedly secured to the ring 185 by, for example, a press fit or fitted connection similar to the connection of FIGS. 18 and 19.

Figure 23:
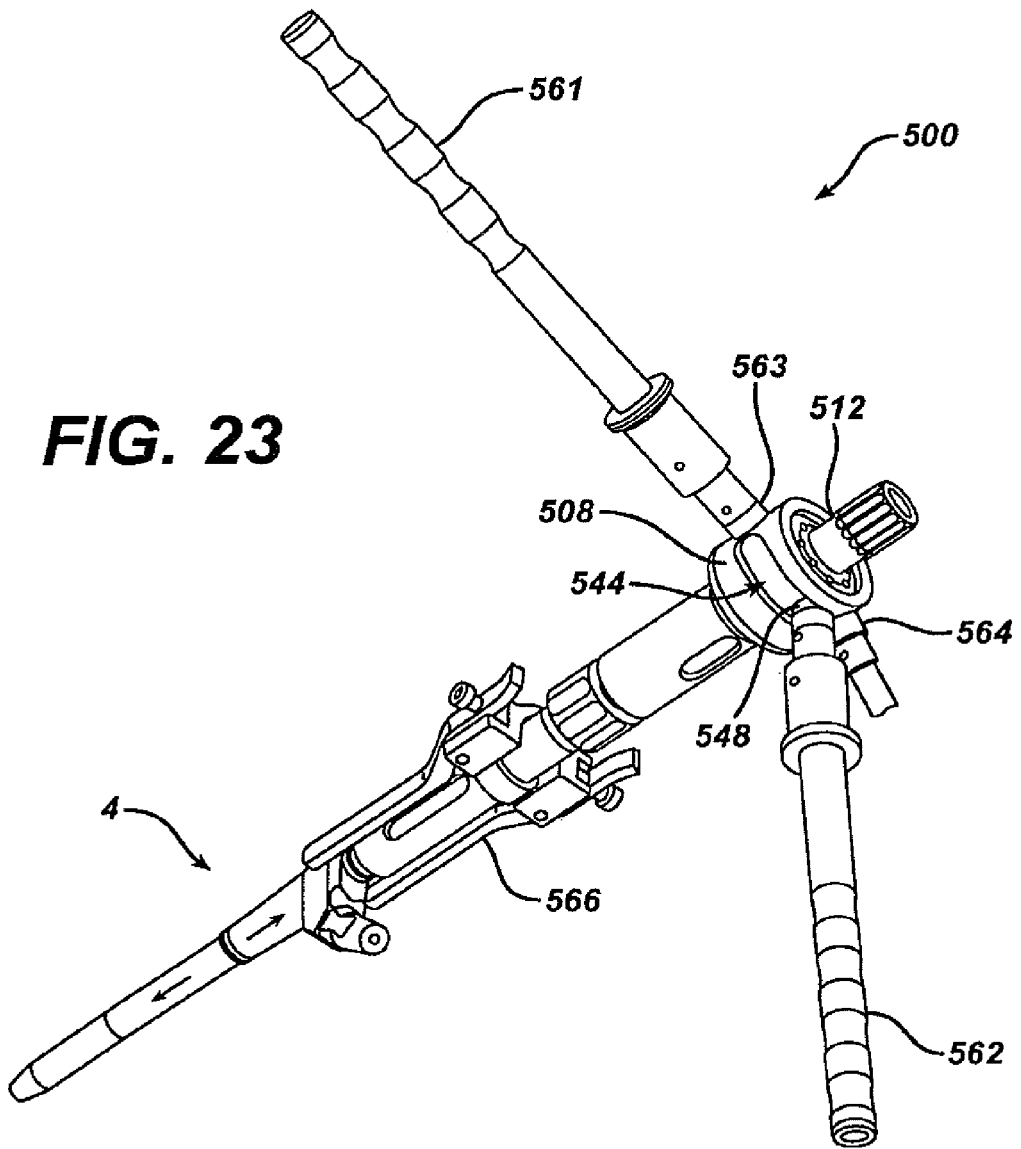
FIG. 23 is a perspective view of the implant of FIG. 4 being disassembled with the assembly tool of FIG. 2.
Figure 24:
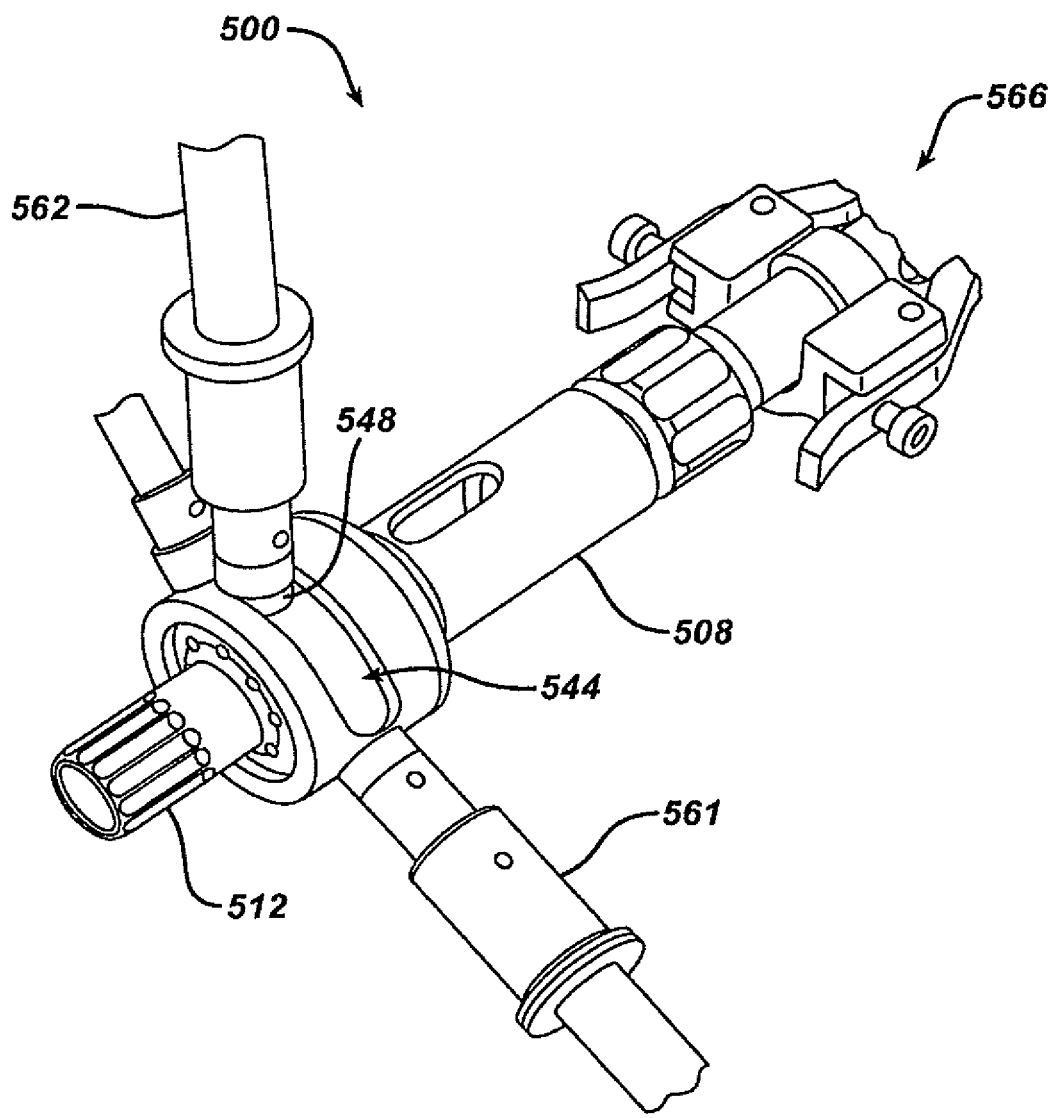
FIG. 24 is a partial enlarged perspective view of the assembly tool of FIG. 2 including the adaptor for use in disassembly.
Figure 25:
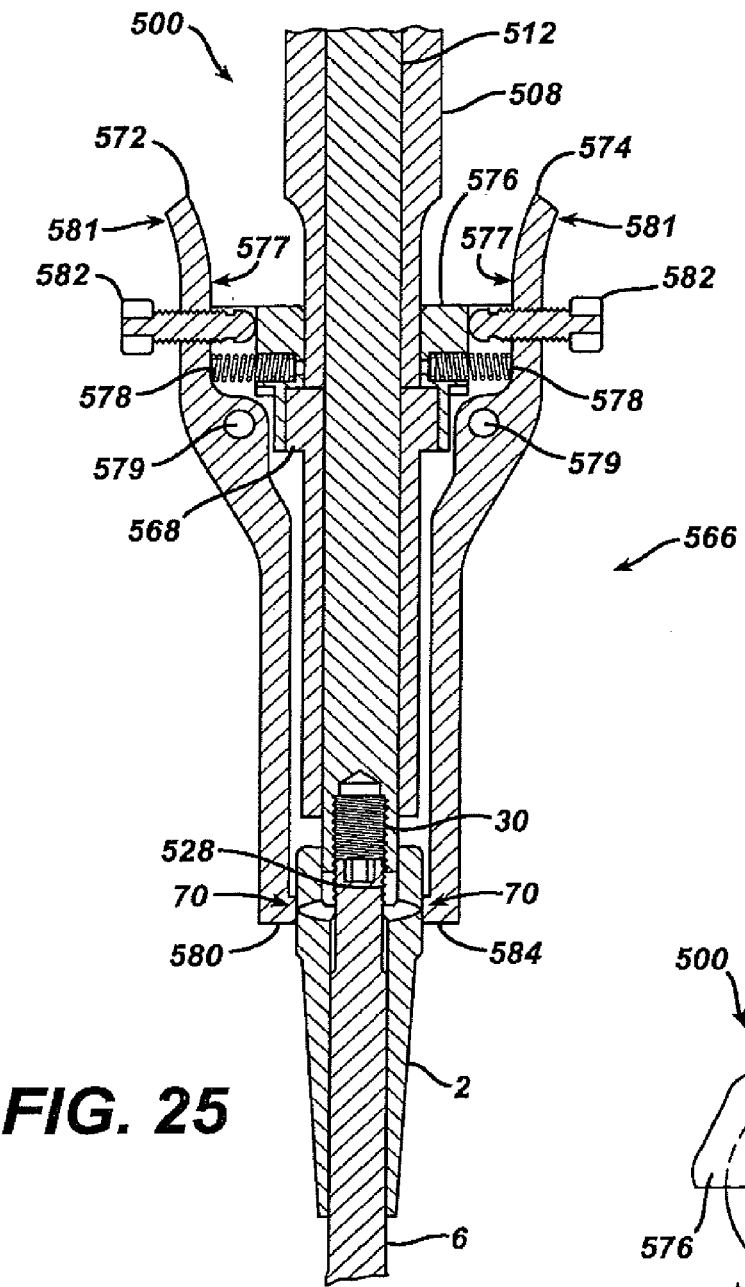
FIG. 25 is a partial cross-sectional plan view of the assembly tool of FIG. 2 showing the implant of FIG. 4 being disassembled and showing the removable disassembly component in position on the assembly tool.

Referring now to FIGS. 23, 24, and 25, assembly tool 500 is shown for use in disassembling the prosthesis 4. The assembly tool 500 is similar to the assembly tool 100 and in fact includes all the components of the assembly tool 100 plus a third member 566 for use in disassembling the prosthesis 4. The assembly tool 500 thus includes a first member 508 identical to the first member 108 as well as a second member 512 identical to the second member 112 of the assembly tool 100 (see FIG. 13).

The assembly tool 500 includes an actuating arm 562 identical to the actuating arm 162 of the tool assembly 100. The assembly tool 500 further includes a restraining arm 561 identical to the restraining arm 162 of assembly tool 100, except that the arm extension 161 of the restraining arm 162 is moved from first arm stem 564 to second arm stem 563. The assembly tool 500 includes a slot 544 identical to the slot 144 of the assembly tool 100. Pin 548, identical to pin 148 of the assembly tool 100, slidably fits within the slot 548.

Referring now to FIG. 25, the third member 566 is shown in greater detail. The third member 566 includes a collar 576 which is slidably fitted over the first member shoulder 568. First arm 572 and second arm 574 are pivotally mounted to the collar 576 by pivot pins 579. The arms 572 and 574 are urged in the direction of arrows 577 by springs 578 positioned between the arms 572 and 574 and the collar 576. Screws 582 are threadably secured to the arms 572 and 574 to limit the movement of the upper portion of the arms 572 and 574 toward the first member 508. First location pin 580 and second location pin 584 are positioned on the first arm 572 and the second arm 574, respectively, for engagement with holes 70 in the proximal body 2 of the prosthesis 4.

When disassembling the prosthesis for utilizing the assembly tool 500, the location pins 580 and 582 are engaged in the holes 70 of the proximal body 2 of the prosthesis 4. Internal threads 528 of the second member 508 are then threadably engaged into the external threads 30 of the distal stem 6 of the prosthesis 4. The second member 512 is then continually tightened until the second member 512 is finger tight to the distal stem 6. The pins 580 and 584 are moved from the proximal body 2 by first moving the arms 572 and 574 in the direction of arrows 581 by means of the operator's fingers. When in position the arms 572 and 574 are released so that the pins 580 and 584 may be properly engaged in the holes 70 of the proximal body 2 of the prosthesis 4.

Figure 26:
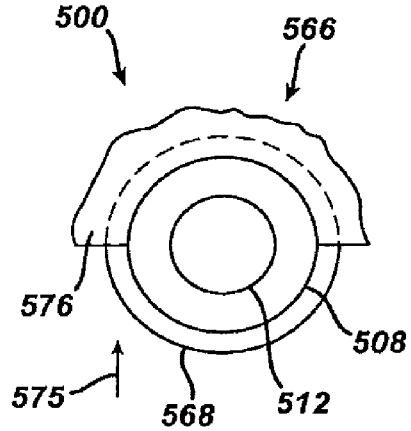
FIG. 26 is a partial top view of the assembly tool of FIG. 2 showing the removable disassembly component in position on the assembly tool.

Referring now to FIG. 26, the collar 576 of the third member 566 is shown in position on the first member 508. The third member 566 is assembled to the first member 508 by moving the third member 566 in the direction of arrow 575.

Figure 27:
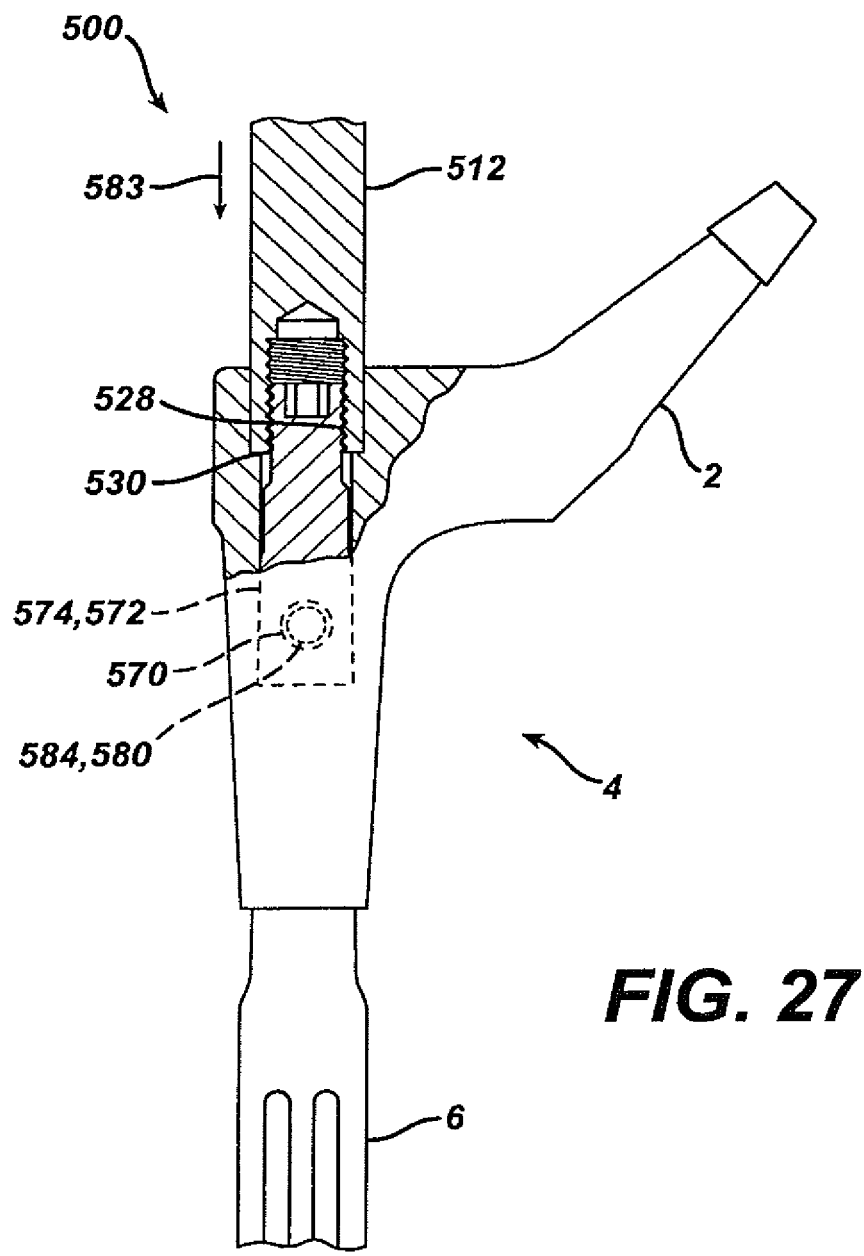
FIG. 27 is a partial enlarged plan view of the implant of FIG. 4 being disassembled with the assembly tool of FIG. 2.

Referring now to FIG. 27, the assembly tool 500 is shown for use with the prosthesis 4 to disassemble the proximal body 2 from the distal stem 6. The pins 580 and 584 of the arms 572 and 574 of the third member 566 are engaged in holes 70 of the proximal body 2 of the prosthesis 4. The internal threads 528 of the second member 512 are threadably engaged with the external threads 30 of the distal stem 6. The second member 512 is then moved downwardly in the direction of arrow 583, thereby separating the distal stem 6 from the proximal body 2.

Figure 28:
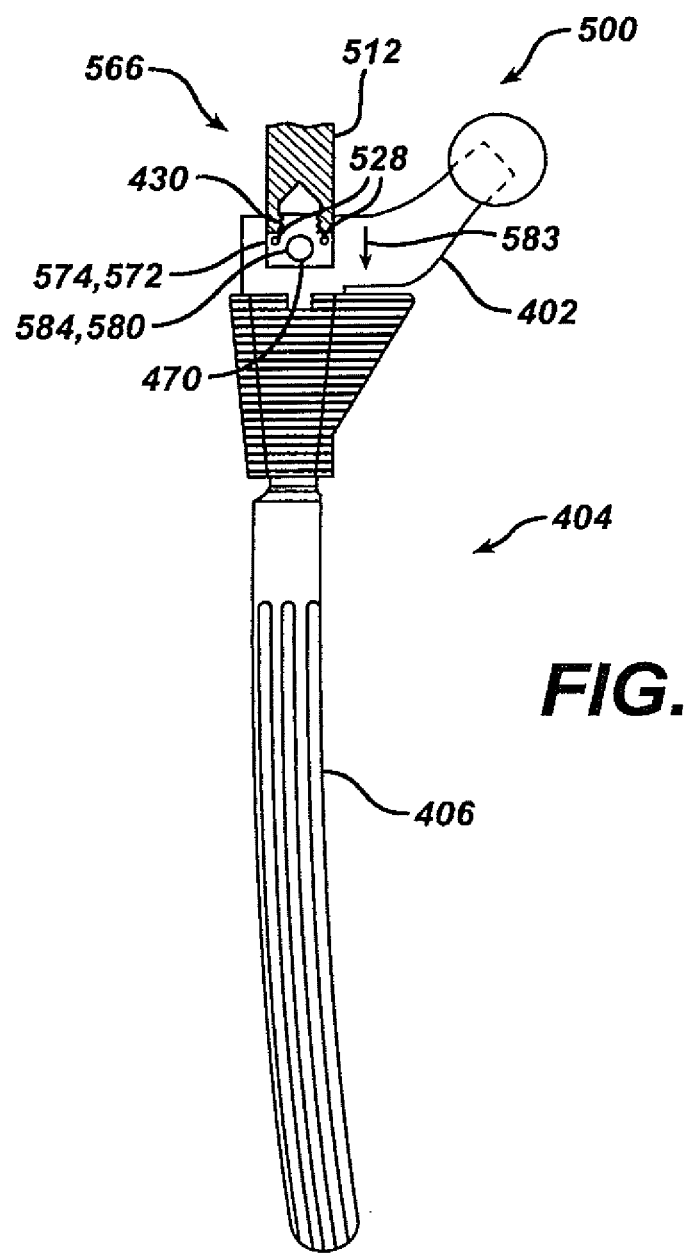
FIG. 28 is a partial enlarged plan view of the implant of FIG. 8 being disassembled with the assembly tool of FIG. 2.

Referring now to FIG. 28, the assembly tool 500 is shown in engagement with the prosthesis 404 to remove the distal stem 406 of the prosthesis 404 from the proximal body 402. The pins 580 and 584 of the arms 572 and 574 of the third member 566 are engaged in holes 470 of the proximal body 402 of the prosthesis 404. The internal threads 528 of the second member 512 are threadably engaged with the external threads 430 of the distal stem 406 of the prosthesis 404. The second member 512 is then moved in the direction of arrow 583 with respect to the proximal body 402 of the prosthesis 404 thereby separating the distal stem 406 from the proximal body 402 of the stem 404.

Figure 29:
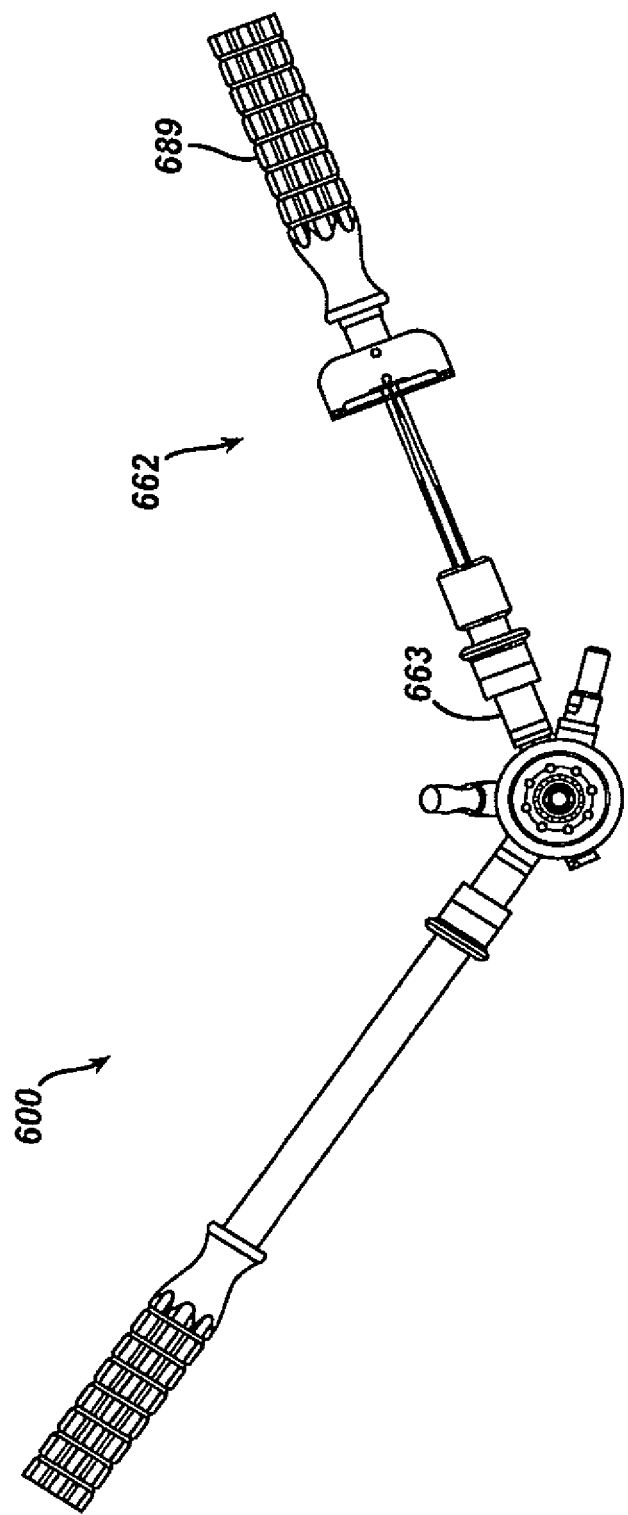
FIG. 29 is a plan view of another embodiment of the present invention in the form of an assembly tool including a torque wrench for measuring the torque applied to the modular implant.

Referring now to FIG. 29, another embodiment of the present invention is shown as assembly tool 600. Assembly tool 600 is similar to assembly tool 100 or assembly tool 500 of FIG. 2 and FIG. 24, respectively, except that articulating arm 662 of the assembly tool 600 is different than the articulating arm 562 of the assembly tool 500 in that the articulating arm 662 includes a torque wrench 689 extending from the arm stem 663. The torque wrench 689 serves to provide a reading of the torque applied by the assembly tool 600. It should be appreciated that the torque wrench 689 may be of a type for recording or reading the applied torque or may be a torque wrench which has a break away or clicking torque at a particular value. Such a torque limiting wrench may provide for an accurate torque to be applied by the assembly tool 600. It should be appreciated that a thrust washer or other force transducer may be positioned in the first member or the second member to monitor the force asserted by the assembly tool.

Referring again to FIG. 10, another embodiment of the present invention is shown as kit 700. Kit 700 includes the assembly tool 100 as well as the prosthesis 4. The assembly tool 100 and the prosthesis 4 form a kit. The kit may be provided with the prosthesis 4 assembled or with the prosthesis 4 disassembled including both the proximal body 2 and the distal stem 6.

Assembly tools 1, 100 and 500 as shown in FIGS. 1, 2 and 24 respectively, may be made of any suitable material and may, for example, be made of a metal. If made of metal, preferably the assembly tool is made of a sterilizable material. The assembly tools 100 and 500 may be made of components of, for example, cobalt chromium alloy, stainless steel alloy, or a titanium alloy. Articulating surfaces of the assembly tool may be surface hardened by processes such as flame hardening.

Figure 30:
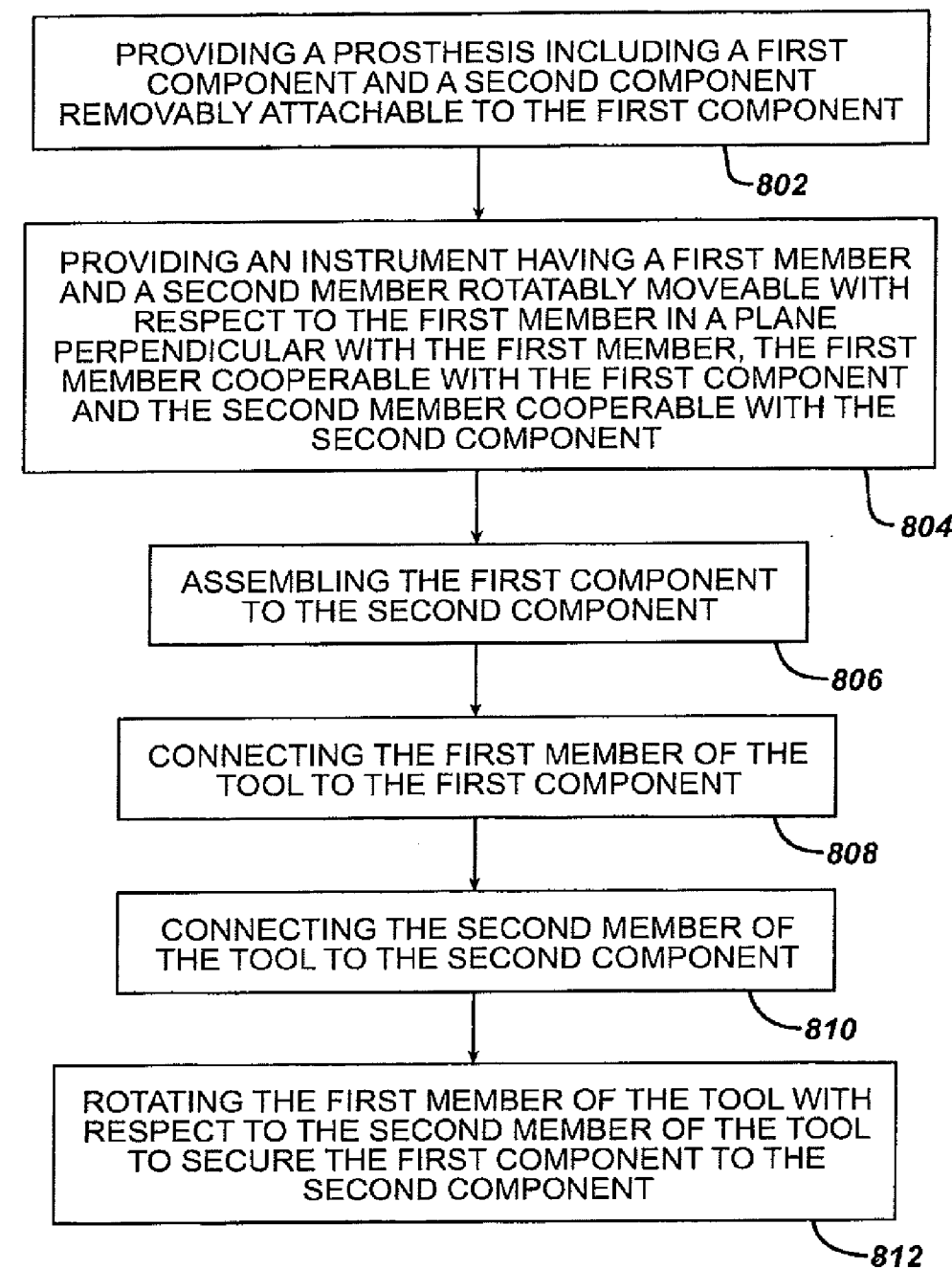
FIG. 30 is a flow chart of a method of using the assembly tool of the present invention according to another embodiment of the present invention.

Referring now to FIG. 30, another embodiment of the present invention is shown as surgical method 800. The method 800 includes a first step 802 of providing a prosthesis including a first component and a second component removably attached to the first component. The surgical procedure 800 also includes a second step 804 of providing an instrument having a first member and a second member rotatably movable with respect to the first member in a plane perpendicular with the first member, the first member cooperable with the second component and the second member cooperable with the second component.

The method 800 may further include a third step 806 of assembling the first component to the second component and a fourth step 808 of connecting the first member of the tool to the first component. The method 800 may further include a fifth step 810 of connecting the second member of the tool to the second component and a sixth step 812 of rotating the first member of the tool with respect to the second member of the tool to secure the second component to the first component.

Figure 31:
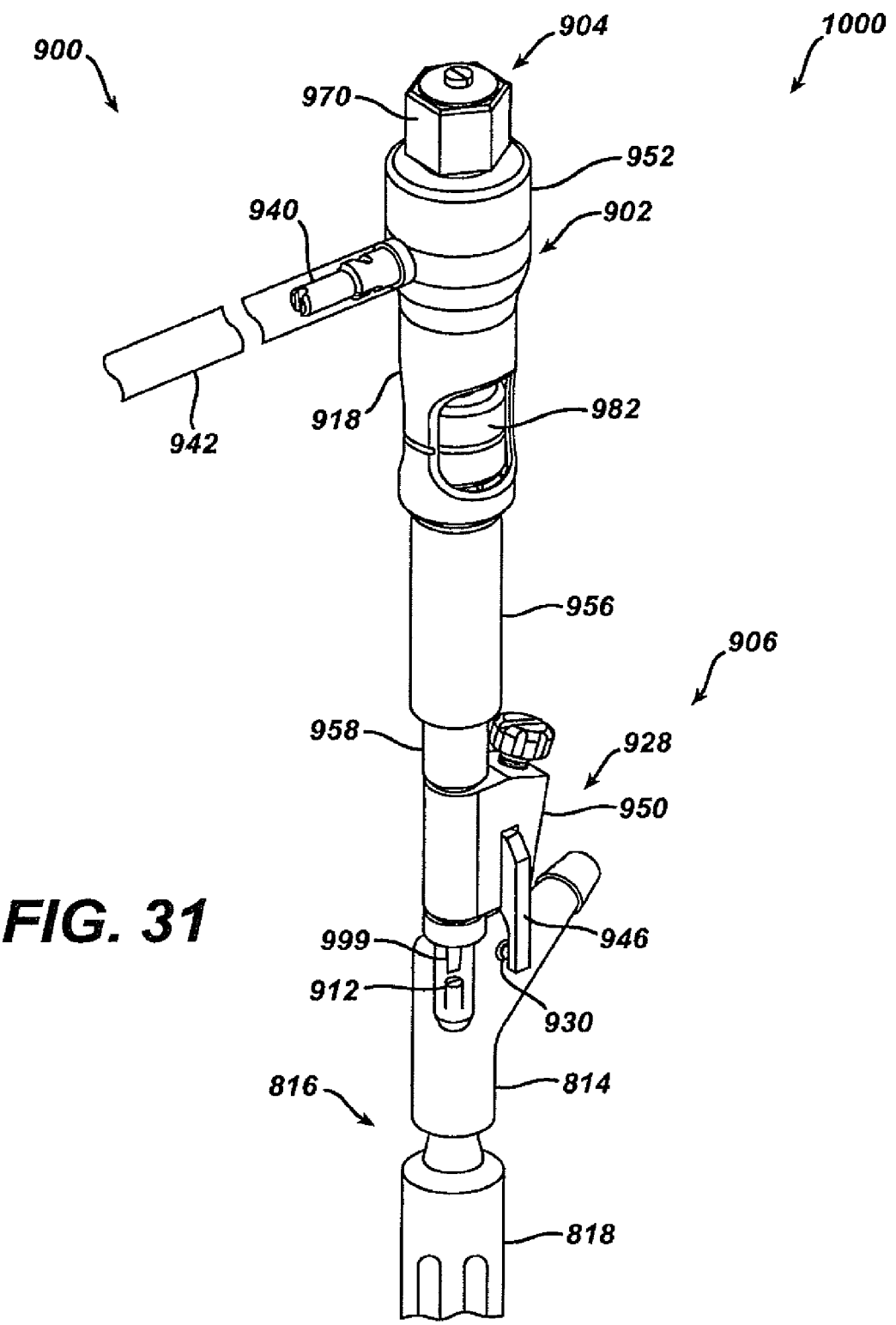
FIG. 31 is a perspective view of an assembly tool assembly tool with alignment feature according to another embodiment of the present invention.

According to the present invention and referring now to FIG. 31, assembly tool 900 is shown for assembly of a first component 814 of a prosthesis 816 to the second component 818 of the prosthesis 816 The prosthesis 816 is for use in joint arthoplasty. According to the present invention, the tool 900 includes a first member 902 operably associated with the first component 814 and a second member 904 operably associated with the second component 818.

As shown in FIG. 31, the first member 902 and the second member 904 are adapted to provide for the assembly of first component 814 of the prosthesis 816 to the second component 818 of the prosthesis 816. The second member 904 is operably associated to the second member 902 to provide relative motion between the first member 902 and the second member 904 for assembly of the first component 814 to the second component 818.

As shown in FIG. 31, the assembly tool 900 further includes an angular orientor 906, that cooperates with the first member 902 or the second member 904 for either replicating or measuring the relative angular orientation of the first component 814 with respect to the second component 818.

Referring now to FIG. 32, articulating reamer 820 is shown for preparing a cavity 822 in a long bone 824. The cavity 822 provides for a position in the long bone 824 for the insertion of, for example, prosthesis 816 of FIG. 31. Articulating reamer 820 is particularly well suited for use in revision surgeries. In revision surgeries, the distal stem is placed more distally than a primary prosthesis so that the distal stem may engage undisturbed bone that has not previously supported a prosthesis.

The long bone 824, in particularly the femur for use in supporting the distal stem of a hip prosthesis is typically curved or arcuate. The long bone 824 thus may have an arch or radius of curvature R defined by for example, a radius of curvature R. The position of the arch or curvature of long bone 824 is a reasonable indicator of the anatomy of the patient.

Thus the position of the curvature of the long bone 824 may be a relative indicator of the proper position of, for example the natural femoral head with respect of the position of the curvature of a long bone 824. The position of the curvature of the long bone 824 may thus provide an indication of the proper alignment of the first component 814 to the second component 818 of the prosthesis 816 of FIG. 31.

Referring again to FIG. 32, articulating reamer 820 includes a distal portion 826, that articulates with respect to the first or shaft portion 828 of the reamer 820 about pivot point 830. A counterbore reamer 832 may slideably fit over shaft portion 828 of the articulating reamer 820 for reaming the proximal portion of the long bone 824 for receiving the prosthesis 816. The articulating reamer 820 may include a connector 834 positioned on the proximal portion 828 of the articulating reamer 820. The articulating reamer 820 and the counterbore reamer 832 combine to form reamer assembly 812 and are well suited for use of long bones 824, which are arcuate. A more complete description of use of articulating and counterbore reamers and their use with orthopaedic trials and implants for hip revision surgeries can be more understood by reference to U.S. patent application Ser. No. 10/606,304 filed Jun. 25, 2003 entitled "NON-LINEAR REAMER FOR BONE PREPARATION AND ASSOCIATED METHOD" incorporated in its entirety by reference.

Figure 33:
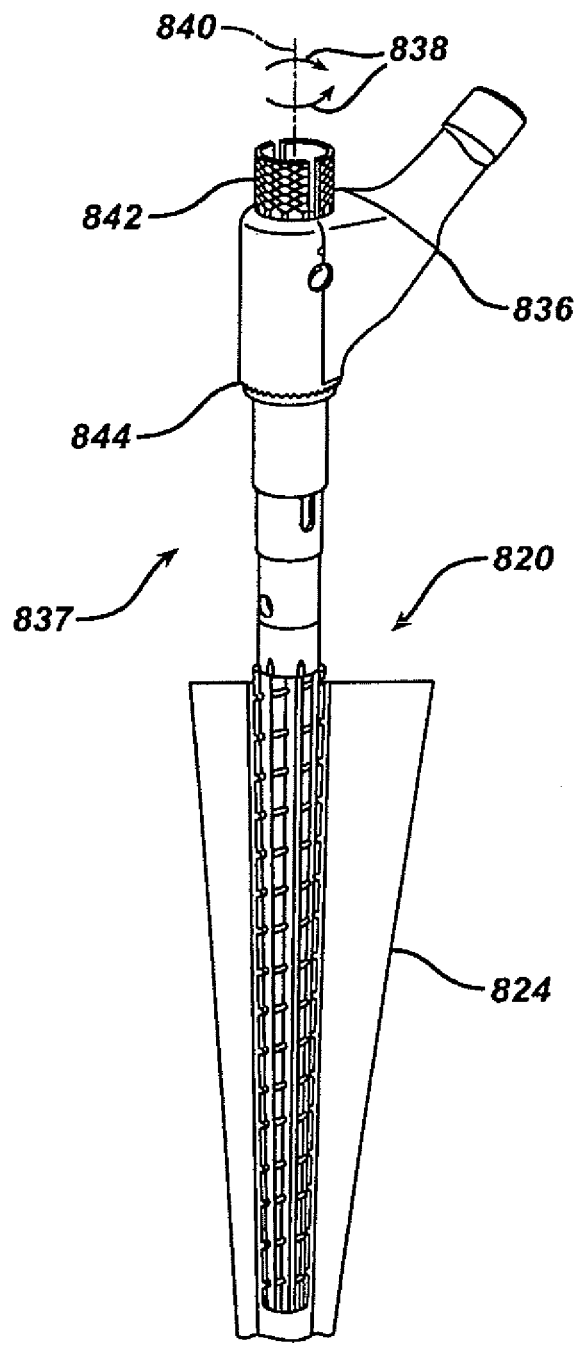
FIG. 33 is a perspective view of a proximal body trial in position on the articulating reamer of FIG. 32 for use with an implant that may be assembled with the assembly tool of the present invention.

Referring now to FIG. 33, a modular body trial 836 is shown in position on the articulating reamer 820. The modular body trial 836 and the articulating reamer 820 may be used in revision hip arthoplasty with the prosthesis 816 and the alignment tool 900 of the present invention as shown in FIG. 31.

Referring again to FIG. 33, articulating reamer 820 remains in the medullary canal of the long bone 824 after the reaming operation has been complete. The proximal body trial 836 is thus assembled into the articulating reamer 820 while the reamer 820 is still in the canal of the long bone to form trial reamer assembly 837. This permits the trialing of the prosthesis without the use of a modular trial and avoids the inaccuracy as well as the time involved in such an additional step of removing the articulating reamer and inserting the distal end of the proximal body trial.

While the articulating reamer 820 is in location in the long bone, the proximal body trial 836 may be rotated in the direction of arrows 838 along longitudinal axis 840 to properly position proximal trial body 836 in the patient. For example, nut 842 may be loosened and the proximal body trial 836 may be rotated in the direction of arrows 838 with teeth 834 being used to control by finite angular movements of, the trial 836. For example if 24 teeth are positioned on the trial 836 each tooth represents 15 degrees of movement. When the proximal body trial is in the proper orientation, the nut 842 may be hand tightened to secure the trial 836 into position.

Figure 34:
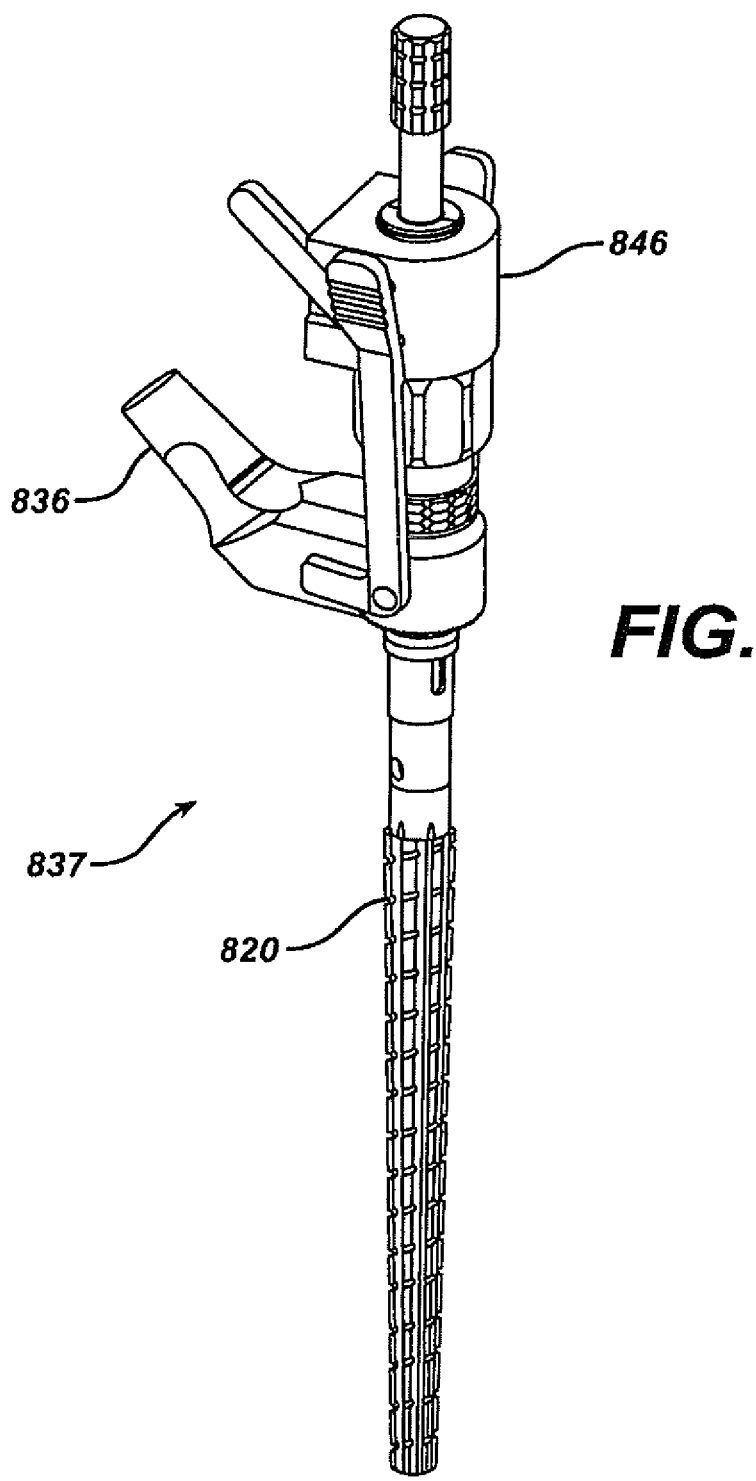
FIG. 34 is a perspective view of the proximal body trial/articulating reamer assembly of FIG. 33 in cooperation with an alignment tool, the proximal body trial/articulating reamer assembly for use with an implant that may be assembled with the assembly tool of the present invention.

Referring now to FIG. 34, once the proximal body trial 836 is in the proper position in the body, an alignment tool 846 may be utilized to measure the preferred anglar orientation of the proximal body trial 836 to the articulating reamer 820. The alignment tool 846 is shown in greater detail in U.S. patent application Ser. No. 10/327,196 entitled "ALIGNMENT DEVICE FOR MODULAR IMPLANTS AND METHODS" incorporated here in its entirety by reference.

Figure 35:
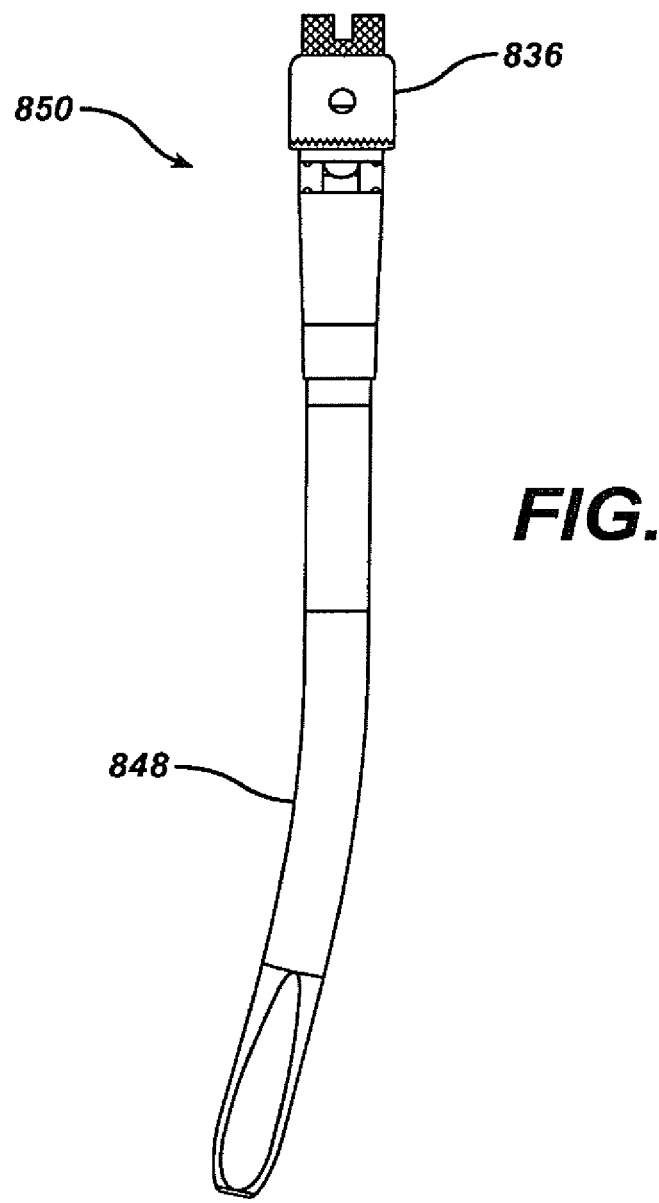
FIG. 35 is a plan view of a proximal body/arcuate distal stem trial assembly for use with an implant that may be assembled with the assembly tool of the present invention.

Referring now to FIG. 35, the proximal body trial 836 is shown assembled with an arcuate distal trial assembly 848 to form the trial assembly 850. The assembly 850 may be utilized instead of the body trial articulating reamer assembly 837 of FIG. 33. The trial assembly 850 may be used in addition to the proximal body trial articulating reamer assembly 837 as an additional step to verify the appropriateness of the trial and corresponding prosthesis for the patient.

Figure 36:
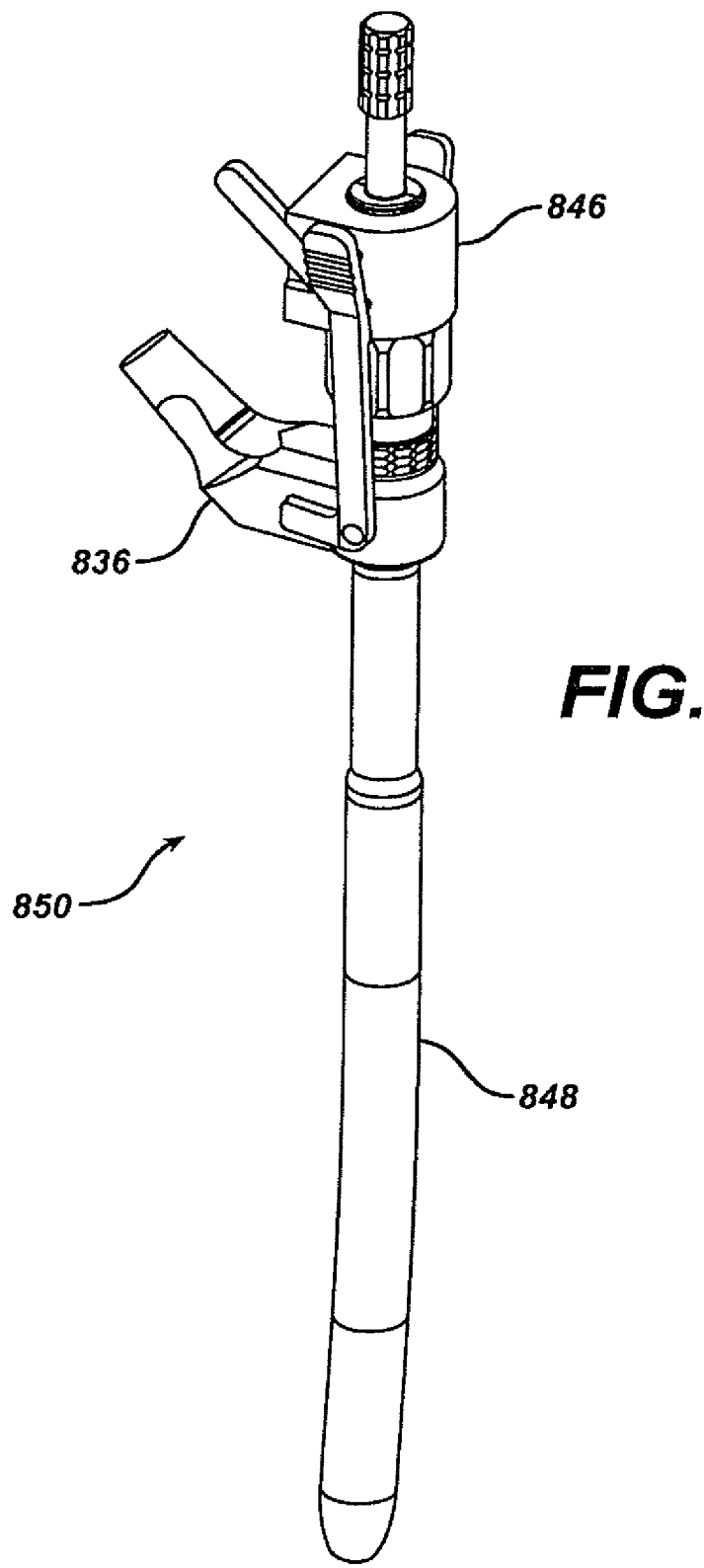
FIG. 36 is a perspective view of the proximal body/arcuate distal stem trial assembly of FIG. 34 in cooperation with the alignment tool of FIG. 34, proximal body/arcuate distal stem trial assembly for use with an implant that may be assembled with the assembly tool of the present invention.

Referring now to FIG. 36, the assembly 850 is shown with the alignment tool 846 in position on the proximal body trial 836. The alignment tool 846 may be utilized to properly orient the proper body trial with respect to arcuate distal stem trial 848 or be used to record the relative position of the proximal body trial 836 to the arcuate distal stem trial 848.

Figure 37:
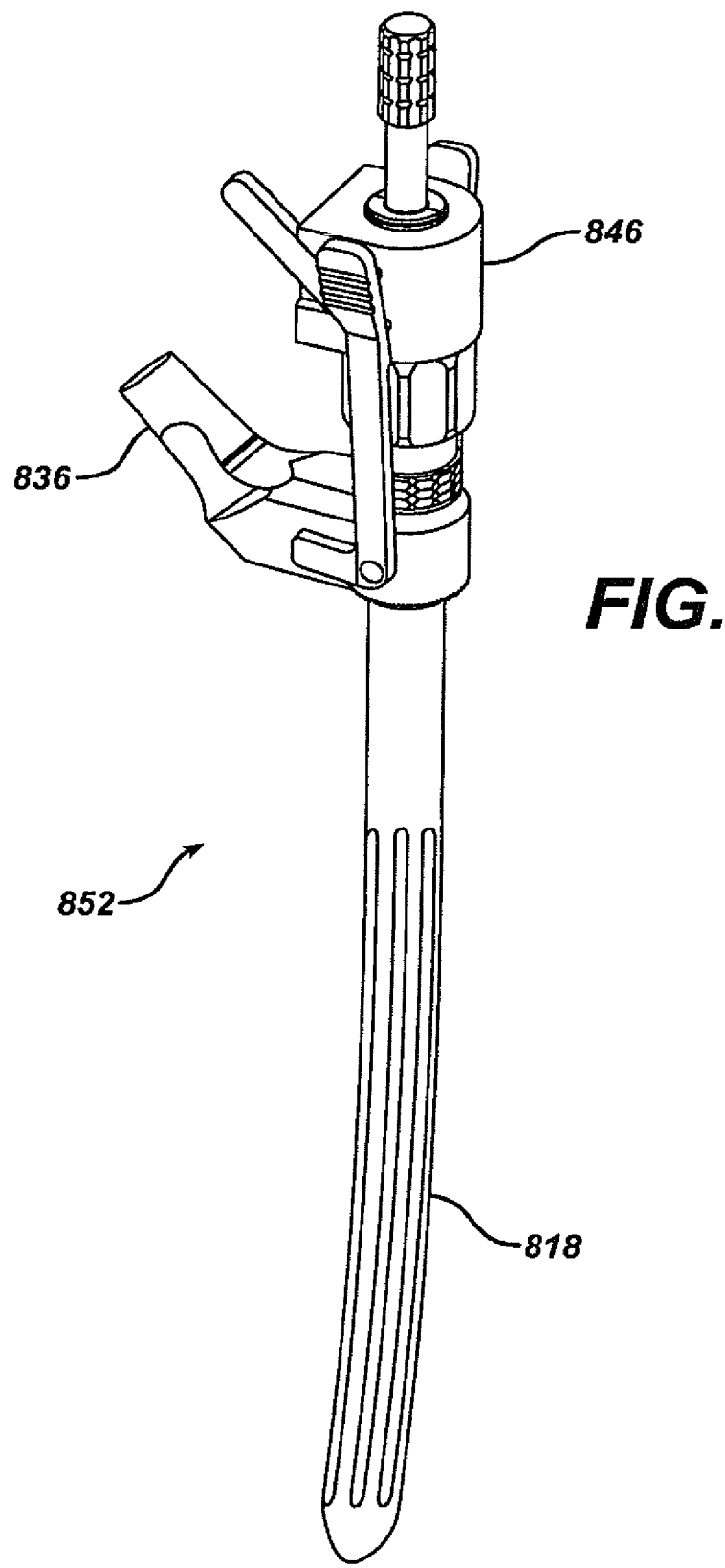
FIG. 37 is a perspective view of a proximal body trial/arcuate distal stem implant assembly in cooperation with the alignment tool of FIG. 34, the proximal body trial/arcuate distal stem implant assembly for use with an implant that may be assembled with the assembly tool of the present invention.

Referring now to FIG. 37, the alignment tool 846 is shown in position on trial assembly 852. Trial implant assembly 852 includes proximal body trial 836 as well as acruate distal stem implant or second component 818. The alignment tool 846 is used to angularly orient proximal body trial 836 to acruate distal stem 818 in a position similar to that of the trial assembly 850 or the proximal body trial acruate reamer assembly 837 (see FIGS. 36 and 33, respectively). The acruate distal stem trial 848 or the articulating reamer 820 may be removed from the canal of the long bone and the arcuate distal stem implant 818 inserted in the long bone. The proximal body trial 836 is positioned with respect to the acruate distal stem implant 818 by use of the alignment tool 846 utilizing in the measurements or settings obtained from trial assembly 850 or the reamer trial assembly 837.

Figure 38:
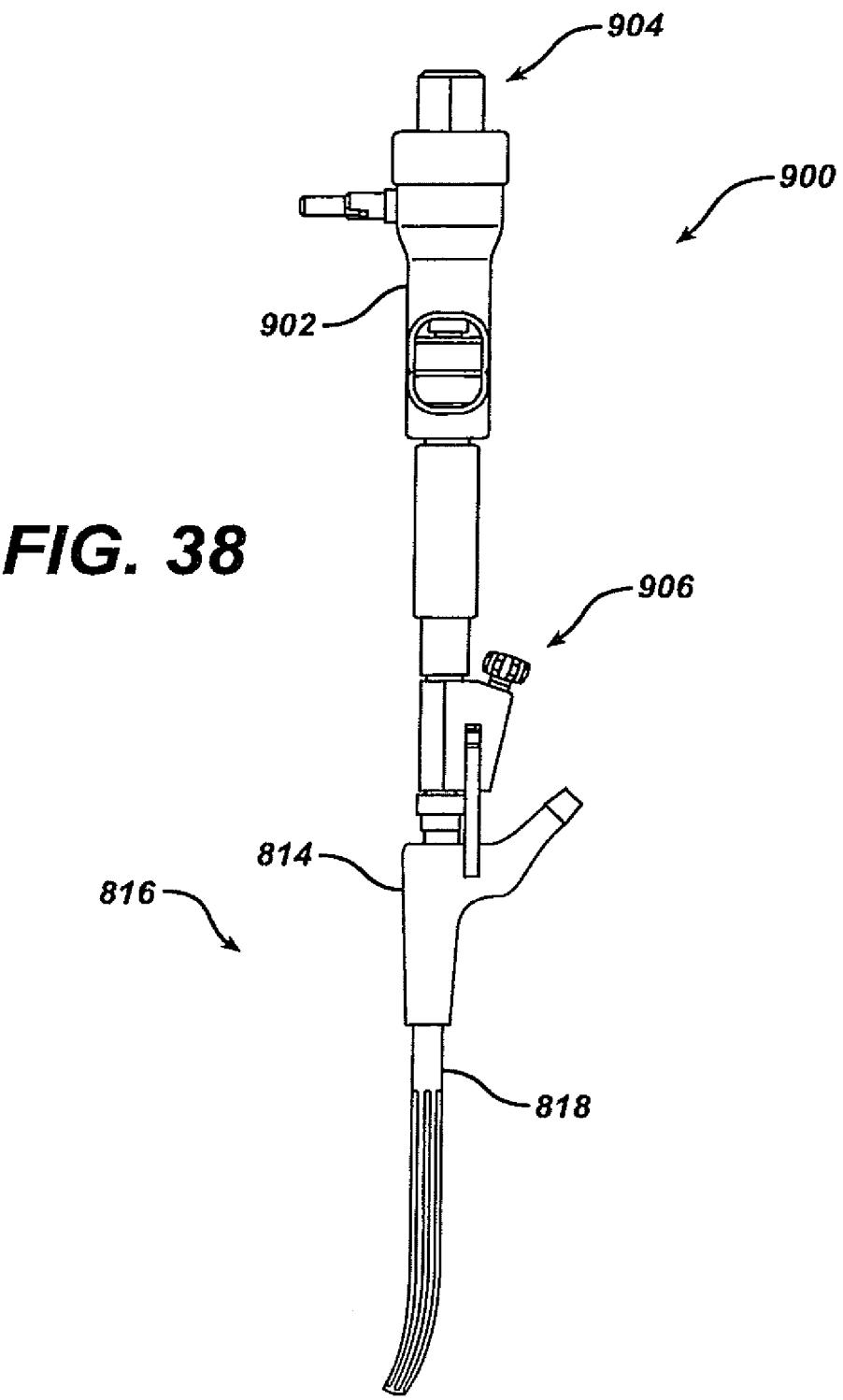
FIG. 38 is a plan view of a proximal body implant/arcuate distal stem implant assembly in cooperation with the assembly tool with alignment feature of FIG. 30.

Referring now to FIG. 38, the assembly tool with alignment feature 900 of the present invention is shown in position on implant assembly or prosthesis 816.

Alignment information may be obtained from alignment tool 846 positioned on trial implant assembly 852 of FIG. 37, from trial assembly 850 of FIG. 33 or from the proximal trial body articulating reamer assembly 837 of FIG. 33. The alignment information may be used to determine the proper anglar orientation of the arcuate distal stem implant with respect to the proximal body implant 814 to provide for a properly assembled implant assembly 816.

Figure 39:
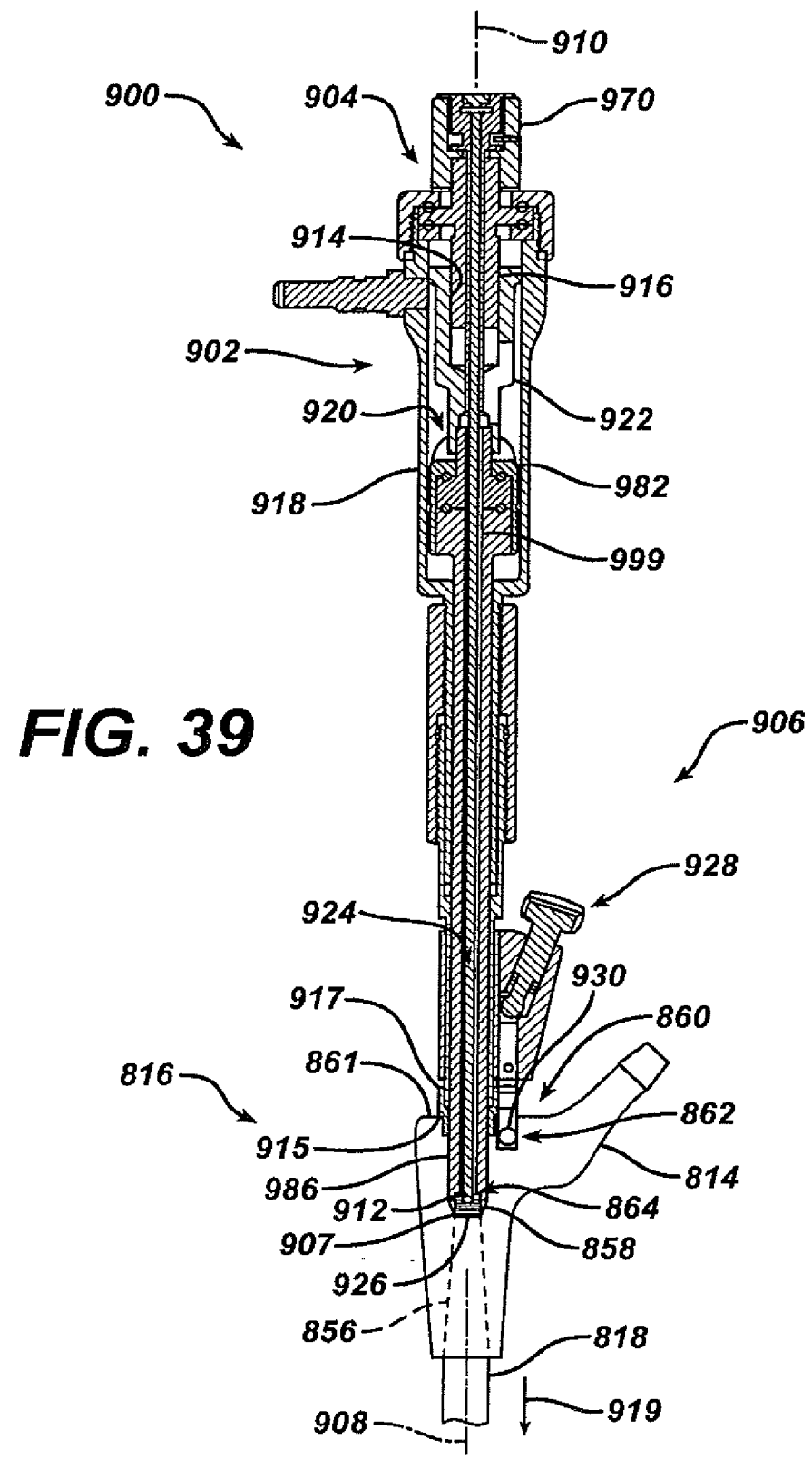
FIG. 39 is a plan view partially in cross section of the assembly tool of FIG. 30 in cooperation with the implant assembly of FIG. 38.

Referring now to FIG. 39, the assembly tool 900 is shown in greater detail. The assembly tool 900 may, as shown in FIG. 39, be configured such that the first member 902 defines first member longitudinal 908. Similarly, the second member 904 may define a second member longitudinal axis 910. The second member 904 may be adapted to provide relative motion of the second member 904 with respect to the first member 902 when the second member 904 is rotated relative to the first member 902 about the second member longitudinal axis 910.

The relative motion of the second member 904 with respect to the first member 902 may be utilized to affect the relative motion of the proximal body 814 or the first component with respect to the distal stem or second component 818 to urge the distal stem 818 into engagement with the proximal body 814.

The assembly tool 900 may be adapted as shown in FIG. 39 to provide for the first member 902 including a first member relative motion feature 914. For example, the first member relative motion feature may be in the form of threads 914 formed on first member 902. Similarly, the second member 904 may include a second member relative motion feature 916. The second member relative motion feature 916 may be in the form of, for example, threads formed on second member 904. The first member relative motion feature 914 and the second member relative motion feature 916 cooperate with each other to provide the relative motion of the first member 902 with respect to the second member 904.

As shown in FIG. 39, the first member relative motion feature 914 or the second member relative motion feature 916 may include, as discussed above, threads. As shown in FIG. 39, the first member 902 may include a body 918 defining a generally cylindrical opening 920 in the body 918. The second member 904 of assembly tool 900 may further include a portion 922 of the second member 904, which is matingly fitted to transverse within the cylindrical longitudinal opening 920 of the first member 902. The portion 922 may be in the form of, for example, a translating member.

As shown in FIG. 39, the assembly tool 900 may further include a cooperating member 924 for cooperating with the second component or distal stem 818. The cooperating member 924 cooperates with the angular orientation feature 906 to replicate and/or measure the angular orientation of the first component 814 with respect to the second component or distal stem 818. The cooperating member 924 may have any suitable size and shape and may for example, be in the form of a cylindrical rod extending longitudinally through assembly tool 900. The cooperating member 924 may include the second member relative motion feature or tang 912.

As shown in FIG. 39, the assembly tool 900 may be configured such that the first component or proximal body 814 of the implant assembly 816 includes an internal taper 854. Similarly, the distal stem or second component 818 of the implant assembly 816 may include an external taper 856. The second component 818 may further an external thread 858 extending from the external taper 856. The second member 904 may include an internal thread 926 for making an engagement with external threads 858 of the second component 818.

As shown in FIG. 39, the assembly tool 900 may be configured such as the first member longitudinal axis 908 and the second member longitudinal axis 910 are coincident.

While the angular orientation feature 906 of the assembly tool 900 may have any suitable size, shape, and configuration, the angular orientation feature 906 may for example, include first orientor 928 connected to the first member 902. The first orientor 928 cooperates with the first component or proximal body 814 of the implant assembly 816. The first component 814 includes a first timing feature 860. The first orientor 928 is operably associated with the first timing feature 860. For example, and is shown in FIG. 39 the first orientor may include a pair of pins 930, which mate with openings 862 located on the first component 814.

The angular orientation feature 906 may further include a second orientor in the form of, for example tang 912. The tang 912 is operably associated with the second member 904 for cooperation with the distal stem or second component 818 of the implant assembly 816. The second component 818 includes a second timing feature 864 in the form of, for example, a slot. The second orientor or tang 912 is operably associated with the second timing feature 864, for example, the slot.

Figure 40:
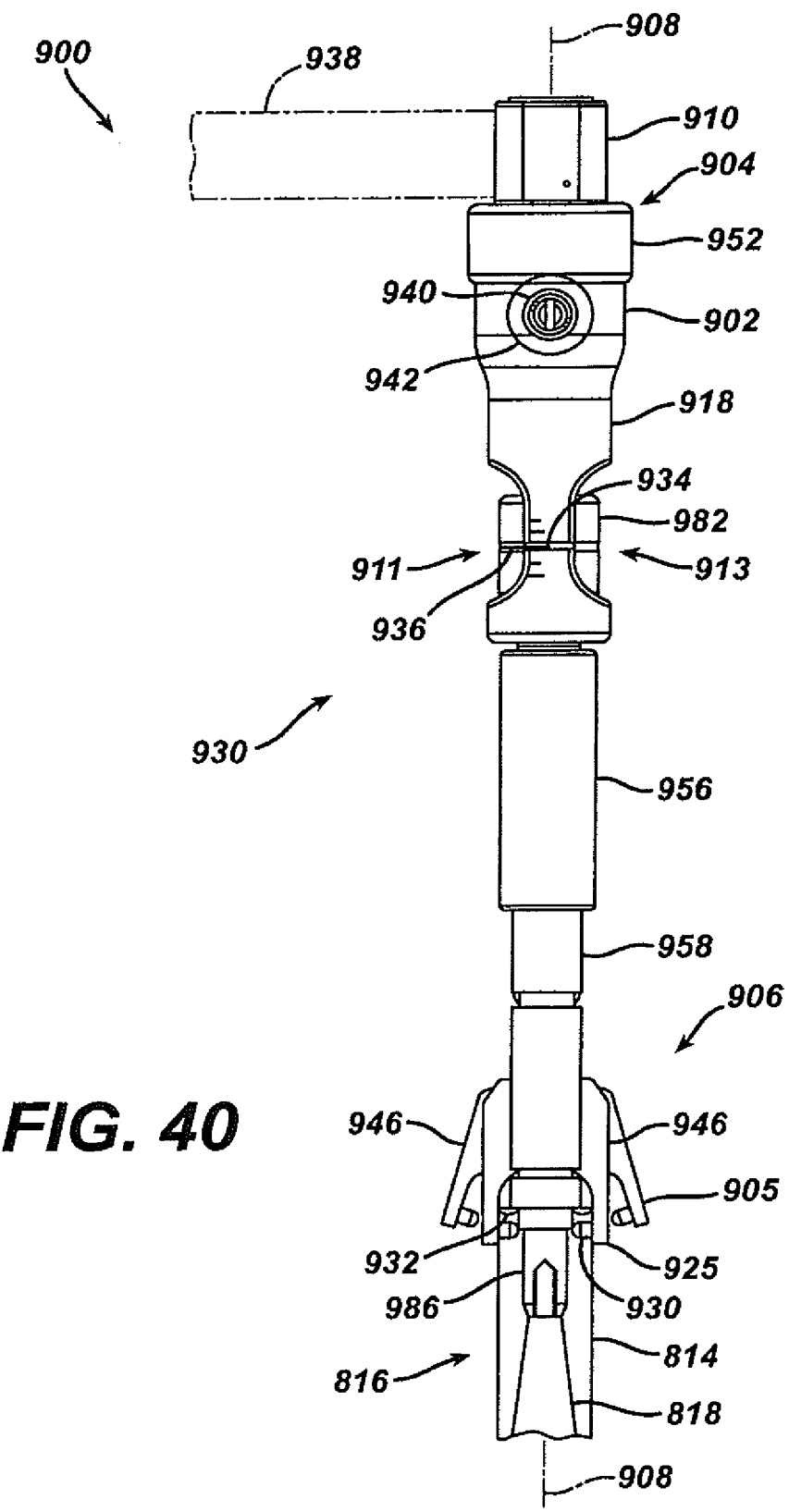
FIG. 40 is aside view partially in cross section of the assembly tool of FIG. 30 in cooperation with the implant assembly of FIG. 38.

Referring now to FIG. 40, the assembly tool 900 may further include a device for preventing or controlling overtightening or securing of the first component 814 to the second component 818 of the implant assembly 816.

The assembly tool 900 may include a displacement measuring device 930 or a force measuring device 932, or both. The displacement measuring device 930 may be utilized for measuring the displacement of the first component 814 relative to the second component 818. Similarly, the force measuring device 932 may be utilized for the measuring of the force related to the relative motion of the first component 814 with respect to the second component 818.

The displacement measuring device 930 may be for example, in the form of indicia 930 including a first mark 934 on for example, first member 902 and a second mark 936 moveable with, for example, second component 818. The distance between the first mark 934 and the second mark 936 may be representative of the displacement of the first component 814 with respect to the second component 818.

Force measuring device 932 may be in the form of, for example thrust washer 932. It should be appreciated that additional force measuring devices in the form of for example, a strain gage or similar devices may be utilized. Alternatively, the force measuring device 932 may be in the form of, for example, torque wrench 938. The torque wrench 938 may be a hand or power tool. The torque wrench 938 may include a feature (not shown) to limit torque such as a clutch or power tool control.

Figure 41:
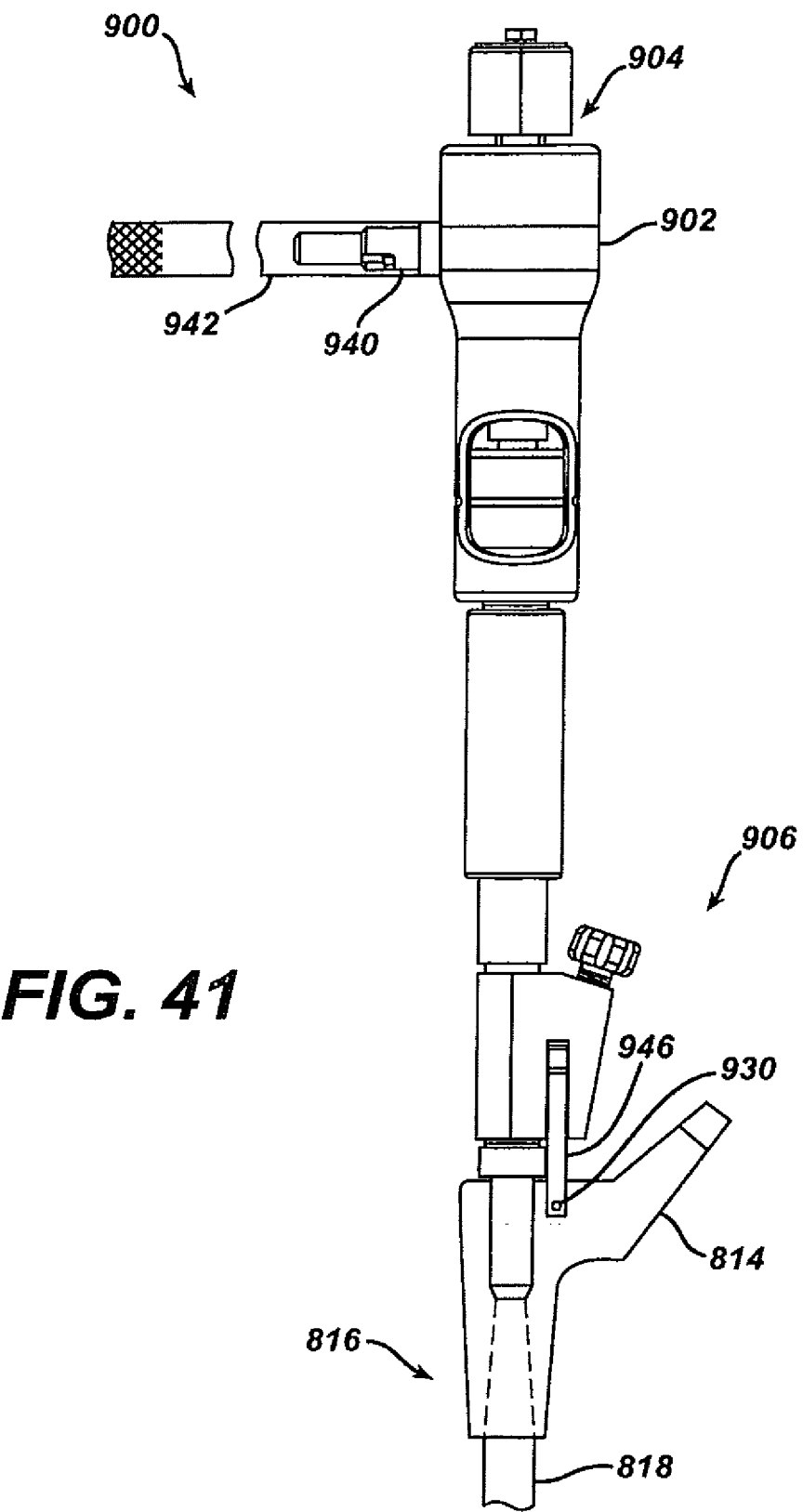
FIG. 41 is a plan view of the assembly tool of FIG. 30 in cooperation with the implant assembly of FIG. 38.

Referring now to FIG. 41, the assembly tool 900 may be configured such that the first member 902 and or the second 904 include a handle 942 extending outwardly from the first member 902 or the second member 904. For example, and as is shown in FIG. 41, the handle 942 extends outwardly from handle stem 940, which extends outwardly from first member 902 of the assembly tool 900. The handle 942 is utilized to assist in holding and stabilizing the assembly tool 900 and to provide resistance to the assembly tool 900 as it is utilized to remove or join the implant assembly 816.

Figure 42:
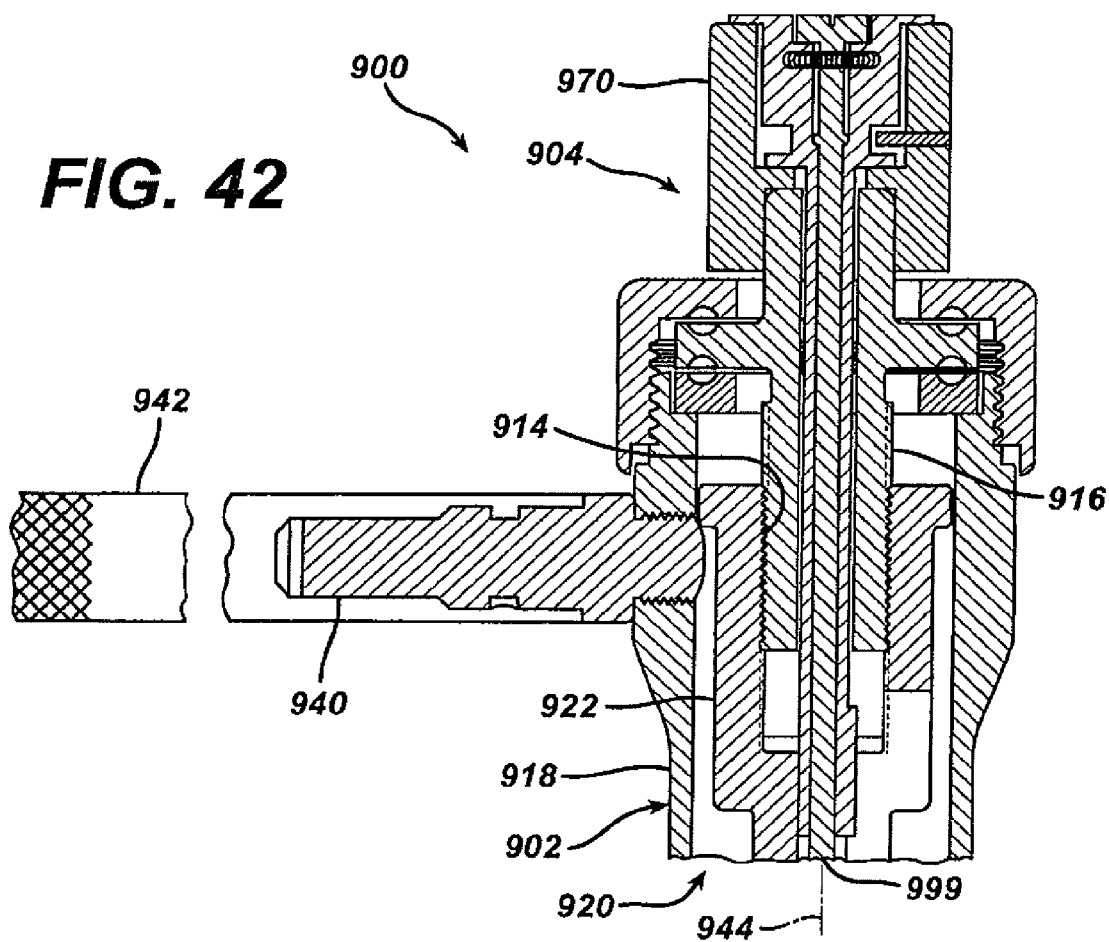
FIG. 42 is a partial plan view in cross section of the assembly tool of FIG. 30 showing the torque input end in greater detail.
Figure 45:
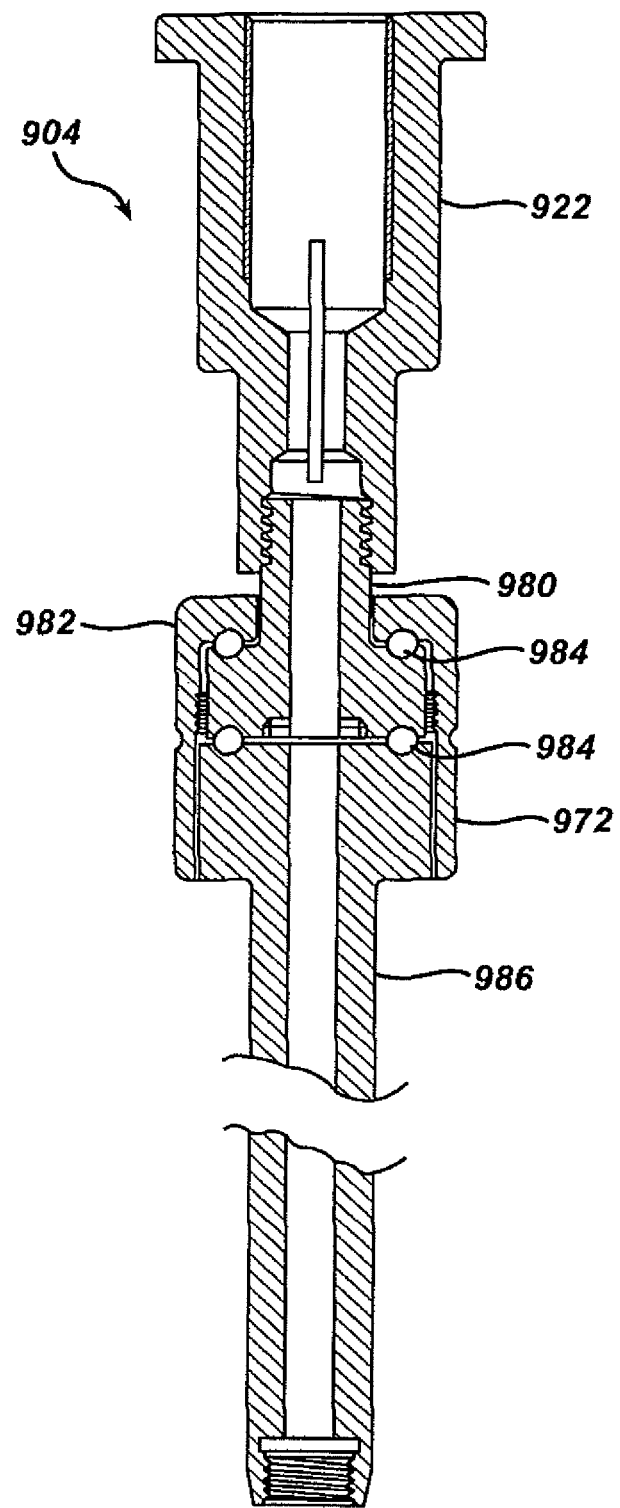
FIG. 45 is a partial plan view in cross section of the assembly tool of FIG. 30 showing the inner force transmitting portion in greater detail.

Referring now to FIGS. 42 and 45, the assembly tool 900 may be configured such that the first member 902 defines a central cavity 920 in the first member 902. Further the assembly tool 900 may be configured such that first member 902 also includes a translating member or translating portion 922 cooperable with the first member 902. The translating member 922 may be fitted at least partially in the central cavity or opening 920. The translating member 922 may define a translating member longitudinal axis 944. The translating member 922 may be adapted as shown in FIG. 42, to translate along the translating member longitudinal axis 944 when the second member 904 is rotated.

Figure 46:
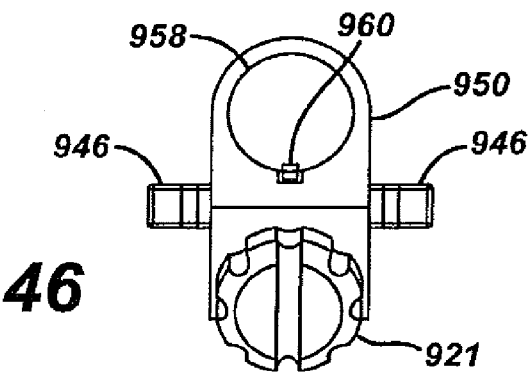
FIG. 46 is a partial top view of the assembly tool of FIG. 30 showing the proximal body alignment portion in greater detail.
Figure 47:
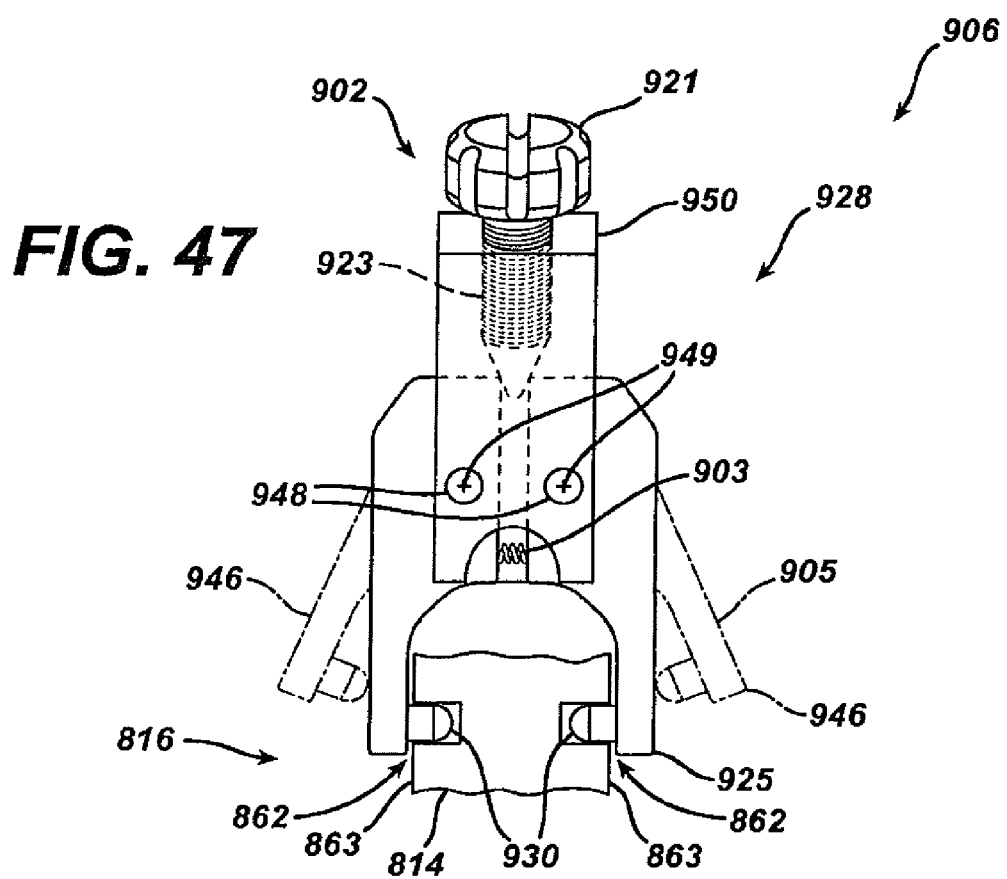
FIG. 47 is a partial end view of the proximal body alignment portion of the assembly tool of FIG. 30.

Referring now to FIGS. 46 and 47, the first orientor 928 of the angular orientation feature 906 is shown in greater detail. While the first orientor 928 may have any suitable shape or configuration capable of orienting first component 814, the first orientor 928 for example, may include a pair of spaced apart arms 946, which rotate about pivot pins 948. Engagement pins 930 are matingly fitted into the openings 862 formed in the proximal body 814 of the implant assembly 816. The first orientor 928, as shown in FIG. 47, is thus pivotally connected to the first member 902. The pins 948, shown in FIG. 47, are connected to first orientor body 950.

Figure 48:
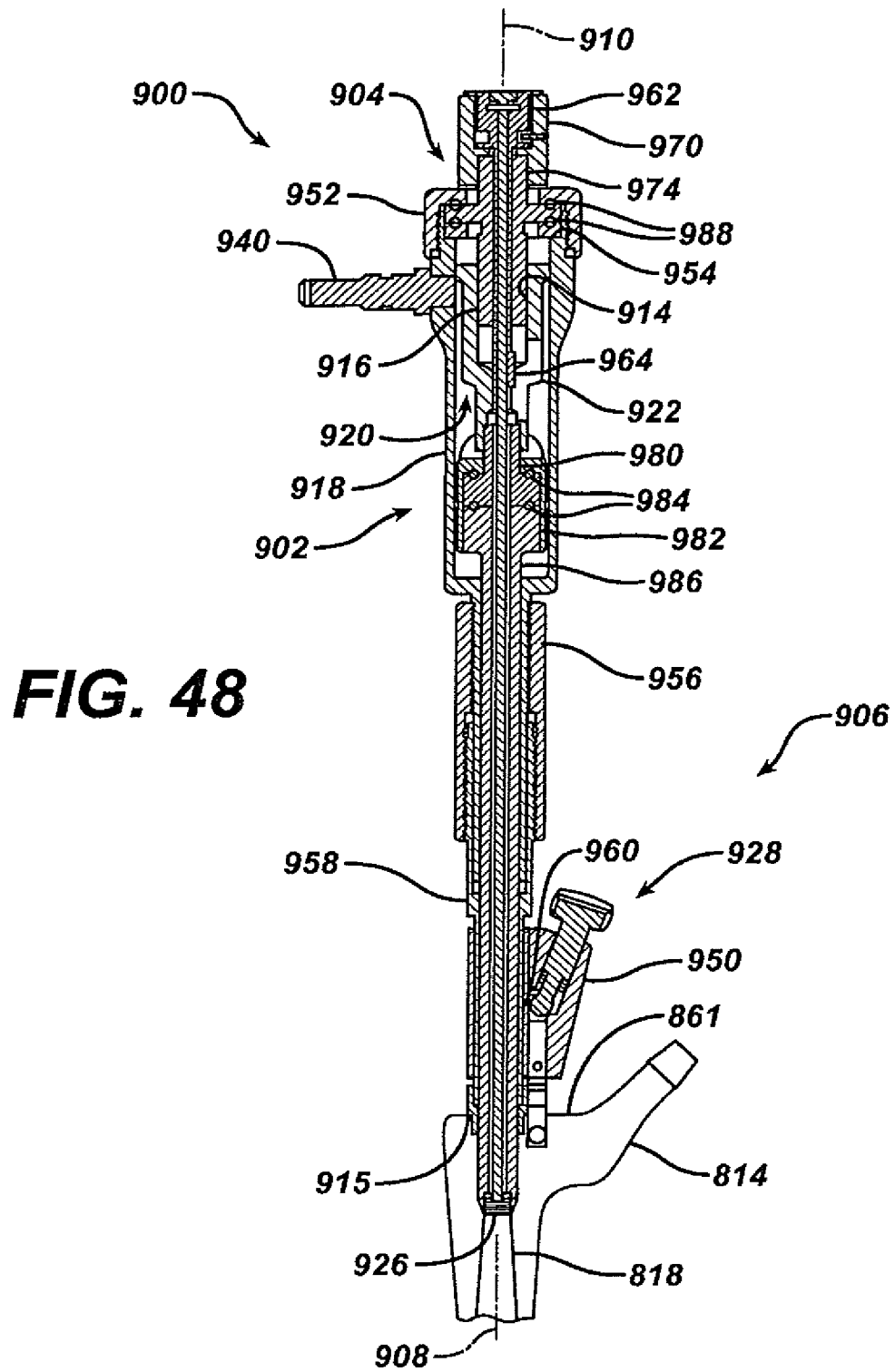
FIG. 48 is a plan view in cross section of the assembly tool of FIG. 30.

Referring now to FIG. 48, the body 950 of the first orientor 928 is slideably fitted to body 918 of the assembly tool 900. The ability of the first orientor 928 to slideably and pivotally be movable to respect to the assembly tool 900 permits the pins 930 to engage the proximal body 814 of the implant 816 in many different positions permitting a variety of proximal body configurations to be compatible with assembly tool 900.

While the first member 902 and the second member 904 may each have an integral or one-piece construction, it should be appreciated the first member 902 and the second member 904 may be made of two or more components. For example and referring now to FIG. 48, the assembly tool 900 may include a modular first member 902 and a modular or multi-piece second member 904.

For example and is shown in FIG. 48, the first member 902 may include the body 918. Body cap 952 may be for example, threadably secured to proximal end 954 of the body 918 of the first member 902.

As shown in FIG. 48, a turnbuckle 956 is threadably secured to the body 918 and an orientation sleeve 958 is threadably secured to the turn buckle 956. The orientor housing 950 slideably fits over the orientation sleeve 958 and axially extending key 960 positioned between the orientor housing 950 and the orientation sleeve 958 serves to prohibit rotation of the orientor housing 950 about the orientation sleeve 958. The turn buckle 956 permits the first member 902 to be adjustable along the first member longitudinal axis 908.

The first member 902 may first include inner spool 962. The inner spool 962 is oriented angularly with the body 918 and the remaining portion of first member 902. The inner spool 962 is connected to the body 918 by being slideably connected and angularly oriented by means of keyway 964 to translating member 922. The translating member 922 is angularly connected to the body 918 by means of tabs 966 extending from the translating member 922, which slideably cooperate with recesses 968 formed in body 918 of the first member 902. (See FIG. 58)

Figure 43:
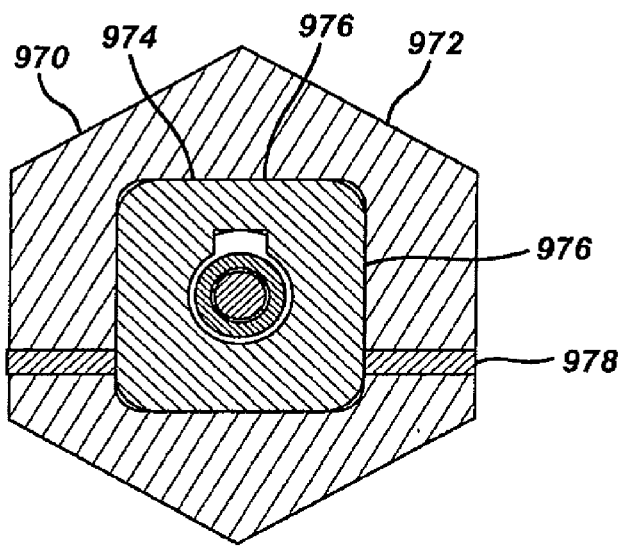
FIG. 43 is a cross sectional view of FIG. 42 along the line 43-43 in the directions of the arrows.

Continuing to refer to FIG. 48, the second member 904 may also be modular or be made of more than one component. For example and is shown in FIG. 48, the second member 904 includes a nut 970. The nut 970 may include external flats 972 (see FIG. 43) and may for example, and is shown in FIG. 43 include six flats 972 or be hexagonal. A drive shaft 974 may be operably connected to 970.

For example and referring again to FIG. 43, the drive shaft 974 may include flats 976, which cooperate with the drive nut 970. A pin 978 may be utilized to secure the drive shaft 974 to the nut 970.

Referring again to FIG. 44, the second member 904 further includes the translating member 922. The translating member 922 is slideably positioned within the opening 920 formed in the body 918 of the first member 902. The translating member 922 is threadably connected to the drive shaft 974 of the second member 904.

Figure 44:
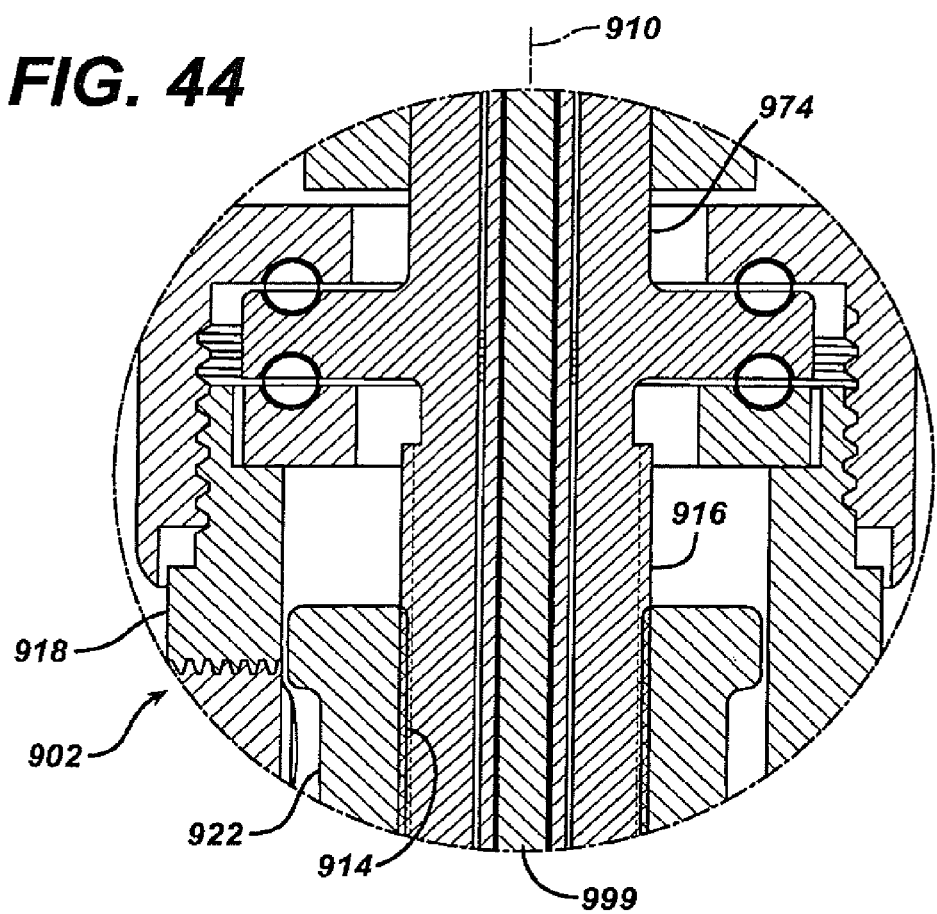
FIG. 44 is a partial plan view in cross section of FIG. 37 showing a portion of the torque input end in greater detail.

For example and is shown FIG. 44, the translating member 922 include internal threads 914, which matingly engage with external threads 916 formed on the drive shaft 974. As the drive shaft 974 rotates with the nut 970 of the second member 904, the translating member 922 translates along second member longitudinal axis 910. Tabs 966 formed on translating member 922 cooperate with recesses 968 formed on the body 918 of the first member 902 (see FIG. 58).

Referring again to FIG. 45, the second member 904 further includes a translator adaptor 980, which may secured to the translating member 922 by any suitable means. For example and is shown in FIG. 45, the translator adaptor 980 is secured to the translating member 922 by means of a threaded engagement.

The second member 904 further includes a thumb wheel sleeve 982 which, as shown in FIG. 45, may be pivotally secured to the adaptor 980 by bearings 984. A proximal body adaptor stem 986 may be secured to thumb wheel sleeve 972 by any suitable method. For example and is shown in FIG. 45, the proximal body adaptor stem 986 may be threadably secured to the thumb wheel sleeve 982.

The drive shaft 974 of the second member 904 may be rotatably secured to the housing 918 of the first member 902 by means of second bearings 988 sandwiching the drive shaft 974 between body cap 952 and body 918 of the first member 902.

Figure 49:
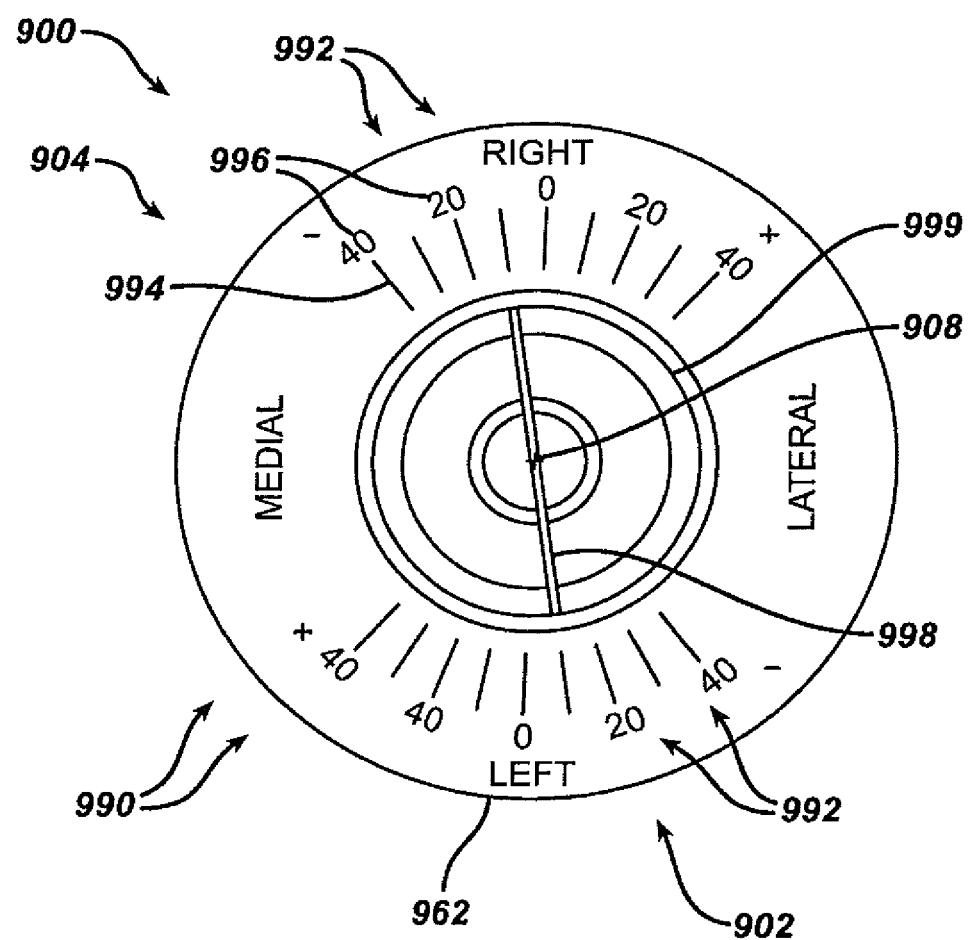
FIG. 49 is a partial top view of the assembly tool of FIG. 30 showing the distal stem alignment groove and the proximal body alignment indicia in greater detail.

Referring now to FIG. 49, the angular orientation feature of the assembly tool 900 further includes indicia 990 on the first member 902 or the second member 904. For example and is shown in FIG. 49, indicia 990 may include spool indicia 992 formed on inner spool 962 of the first member 902. The spool indicia 992 may include marks 944 extending from first member longitudinal axis 908. Spool indicia 992 may further include letters or numerals 996 adjacent radial marks 994 formed on the inner spool 962. The indicia 990 is shown in FIG. 49 may further include a radial mark 998 formed on central alignment stem 999.

Figure 50:
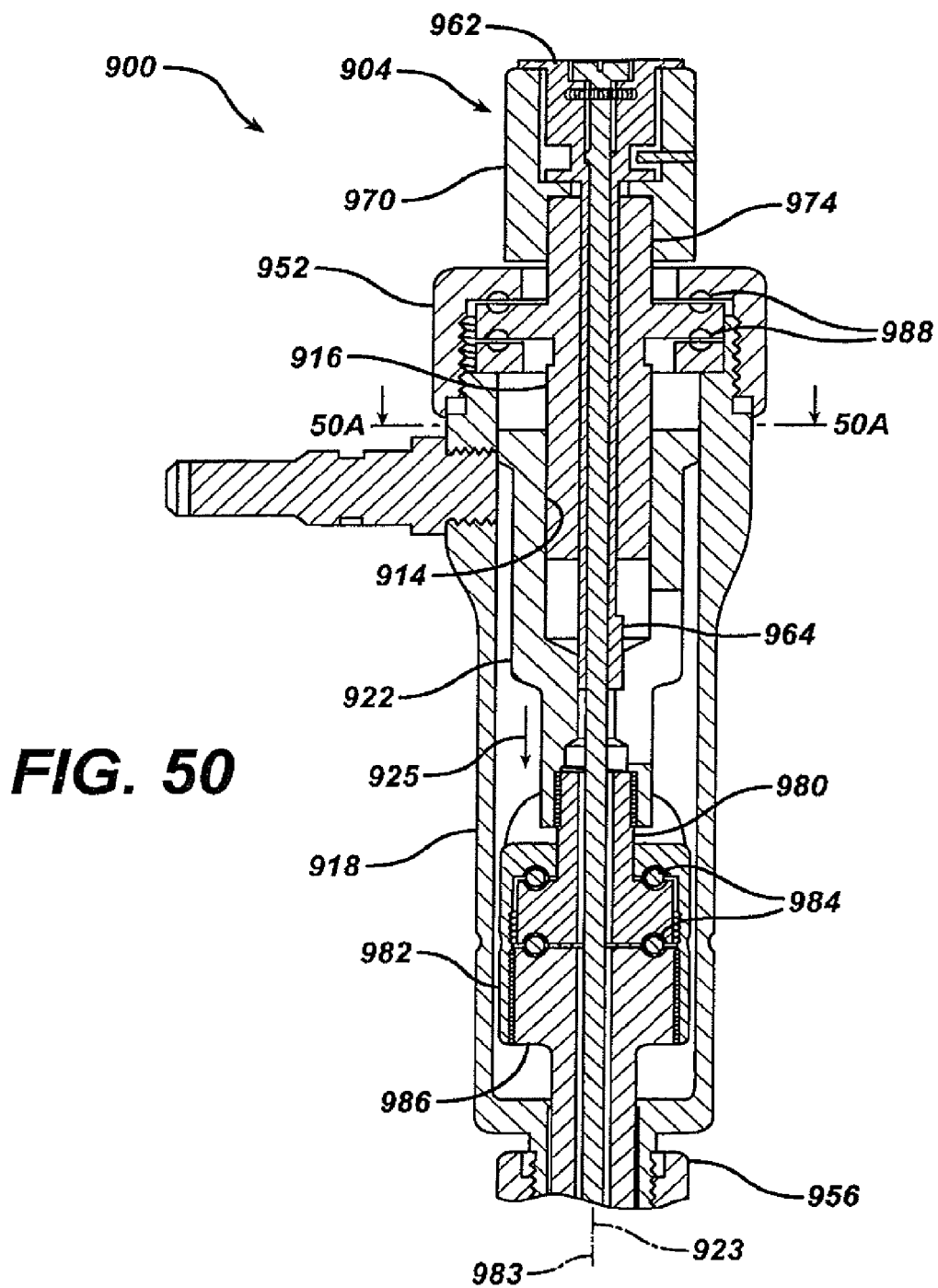
FIG. 50 is a partial plan view in cross section of the assembly tool of FIG. 30 showing the upper portion in greater detail.

Referring now to FIG. 50, the assembly 900 may be configured as is shown in FIG. 50 with the second member 904 further including a rotatable member, for example thumb wheel sleeve 982. The thumb wheel sleeve 982 defines a thumb wheel longitudinal axis 983 of the thumb wheel sleeve 982. The wheel sleeve 982 is cooperable with the translating member 922. The rotatable member or wheel sleeve 982 is adapted to translate along the rotatable longitudinal axis 983 with the translating member 922 when the translating member 922 translates along the translating member longitudinal axis 923. The rotatable member 982 is adapted to be manually rotated about the rotatable member longitudinal axis 983 to advance the proximal body adaptor stem 986 in the direction of arrow 925.

Referring now to FIG. 39-51, the assembly tool 900 is shown in use with the implant assembly 916. The assembly tool 900 may, as shown FIG. 39-51, include numerous components which are assembled together. The assembly tool 900 may be made of any suitable, durable material or materials. For example, the assembly tool 900 may be made of a durable plastic, a metal, or a composite material.

Preferably the assembly tool 900 is designed to be sterilizable by commercially available sterilization techniques, for example, by auto-claving. The assembly tool 900 may be made a variation of metals. The assembly tool 900 may for example, be made of a metal, such as a cobalt chromium alloy, a stainless steel alloy, or a titanium alloy. The assembly tool 900 may use for assembly and disassembly 916. It should be appreciated that the assembly tool 900 may be used to secure and release proximal body 814 from the distal stem 818 of the implant assembly 816.

Alignment tool 846 (see FIG. 34) may be utilized to measure or set the angle orientation of the first component 814 with respect to the second component 818. Alternatively, a measurement may be made with, for example, the alignment tool 846 of FIG. 34, to determine the angular orientation preferred from example, trialing of the trial assembly 850 of FIG. 35 or the proximal body trial and articulating reamers assembly 837 of FIG. 34 to determine the appropriate angular orientation of the first component 814 to second component 818. The angular orientation desired may be measured by utilizing the alignment tool 848 of FIG. 36 and the assembly tool 900 may be utilized to set or align the angular orientation of the component 814 to the second component 818.

The assembly tool 900 is assembled onto the prosthesis 816 by advancing the assembly 900 along the second member longitudinal axis 908 of the assembly tool 900. As shown in FIGS. 40, 46, and 47 the angular orientation feature 906 is adjustable to assist the assembly tool into engagement with the first component 814 of the implant 816.

For example and is shown in FIGS. 46 and 47, the first orientor 928 of the angular orientation feature 906 includes a spring 903, which is used to move the arms 904 to second position or assembly position 905 as is shown in phantom. In the assembly position 905, the pins 930 are extending apart sufficiently to permit the pins 930 to clear sidewalls 863 of the proximal body 814 of the prosthesis 816. After the first orientor 928 passes along the sidewalls 863 of the proximal body 814. The proximal body adaptor stem 986 of the second member 904 engages the second component or distal stem 818 (see FIG. 48).

Referring again to FIG. 39, internal threads 926 located on end 907 of the proximal body adaptor stem 986 are next threadably engaged with external threads 858 located on the distal stem 818 of the implant 816. The internal threads 926 are engaged with the external threads 858 by rotating the proximal body adaptor stem 986 by using for example, thumb and index finger to rotate the thumb wheel sleeve 982.

Referring to FIG. 40, the thumbs wheel sleeve 982 may be reached for rotation by placing one's thumb and index finger against the thumb wheel sleeve 982 through first window 911 and second window 913 formed in the body 918 of the first member 902 of the assembly tool 900.

Referring again to FIG. 39, the proximal body adaptor stem 986 is rotated until the internal threads 926 of the proximal body adaptor stem 986 are in complete engagement with the external threads 858 on the distal stem 818. At this point the assembly tool 900 is advanced downward in the direction of the arrow 919 along the first member longitudinal axis 908 until the lower end 915 of orientor cap 917 of the orientor housing 950 contacts the proximal face 861 of the proximal body 814 of the prosthesis 816.

Once the assembly 900 is seated against the proximal face 861 of the proximal body 814 and now referring FIGS. 46 and 47 thumb screw 921 is threadably secured to the orientor housing 950 of the first orientor 928. The thumb screw 921 is rotated to advance thumb screw stem 923 against the arms 946 of the first orientor 928. As the stem 923 is advanced the arms 946 move from assembly position 905 as shown in phantom to the operating position 925 as shown in solid. Pins 930 are fitted within the openings 862 in the proximal body 814 of the implant assembly 816.

It should be appreciated that the orientor housing 950 may be slideably moved along the orientor sleeve 958 so that the pins 930 will engage in the openings 862. When the arms 946 of the first orientor 928 of the assembly tool 900 are in the operating position 925, the angular orientation of the proximal body 814 to the distal stem 818 may be verified.

For example and referring now to FIG. 49, the radial mark 998 on the central aligning stem 999 corresponds to the angular position of the distal stem 818 while the spool indicia 992 on the inner spool 962 of the first member 902 indicate the angular position of the proximal body 814 of the prosthesis 816. For example and is shown in FIG. 49, the radial mark 998 of the central alignment stem 999 shows that the alignment stem 999 or distal stem 818 are in position at a negative to 10 degree right position relative to the first member or proximal body 814.

Once the assembly tool 900 is properly positioned on the prosthesis as shown in FIGS. 39-41 and is described heretofore, the torque wrench 938 is positioned on nut 970 and is rotated to secure the distal stem 818 into the proximal body 814.

Figure 50A:
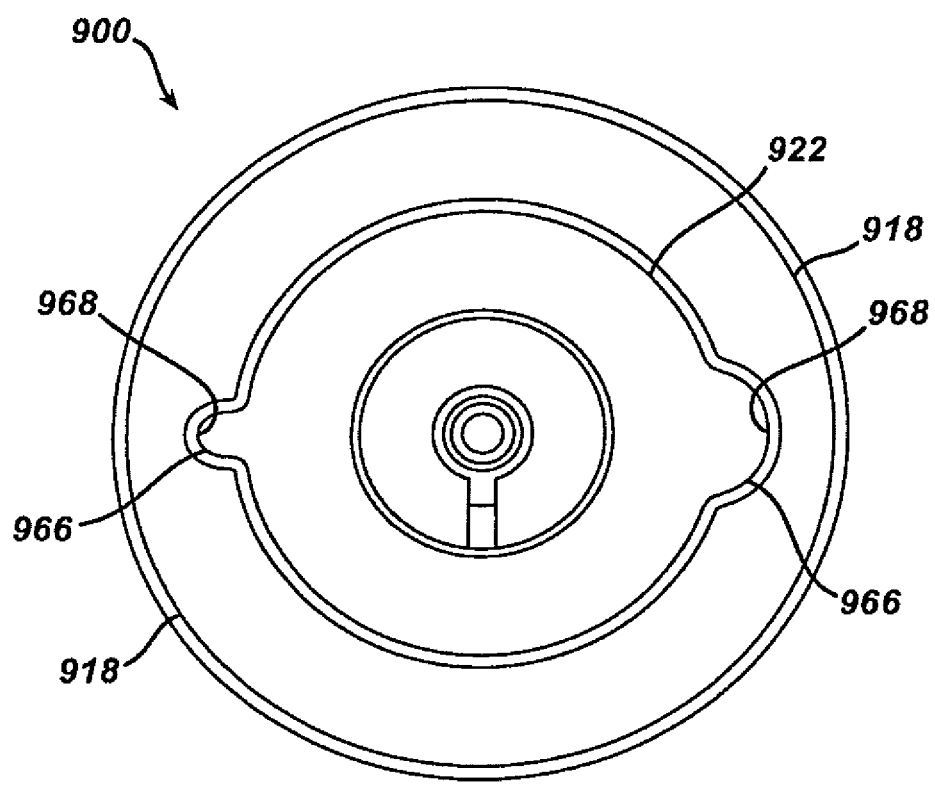
FIG. 50A is a cross sectional view of FIG. 50 along the line 50A-50A in the directions of the arrows.
Figure 51:
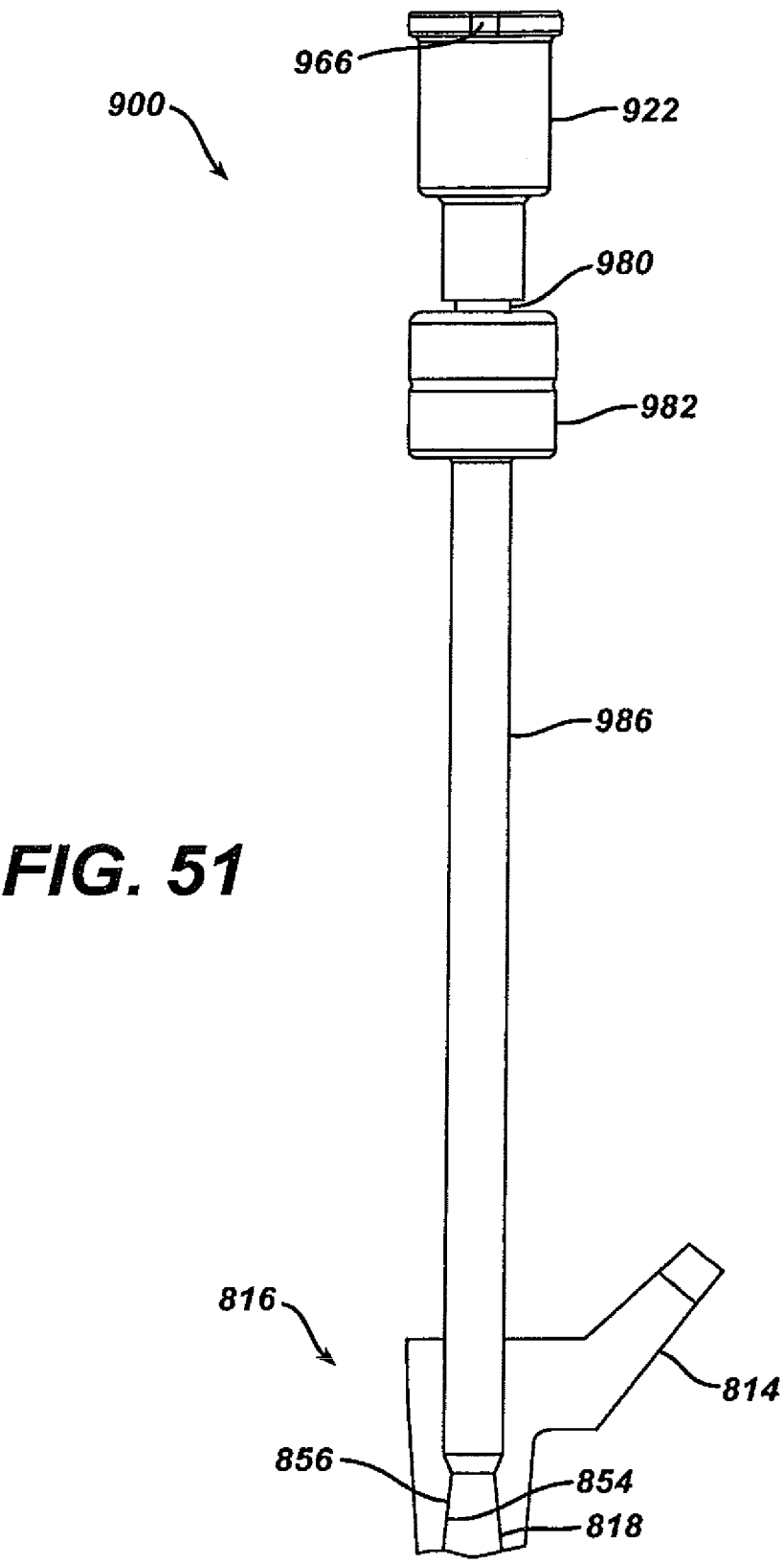
FIG. 51 is a partial plan view of the inner force transmitting portion of FIG. 45 in greater detail.

Referring now to FIGS. 50, 50A, and 51, as the nut 970 is rotated, the drive shaft 974 which is secured to the nut 970 also rotates with the nut 970. As the drive shaft 970 rotates, the external threads 916 on the drive shaft 974 engage with internal threads 914 formed on the translating member 922. Since the translating member 922 includes tabs 966, which mate with the recesses 968 (see FIG. 50A), the translating member 922 may not rotate about axis 983. Thus, as the drive shaft 974 rotates, the translating member 922 translates downwardly into the direction of arrow 925.

The translating member 922 is fixably secured to the translating adaptor 980. The translating adaptor 980 is positioned between the thumb wheel sleeve 982 and the proximal body adaptor stem 986. Thus as the translator adaptor 980 moves downwardly in the direction of arrow 925, the thumb wheel sleeve 982 and the proximal body adaptor stem 986 likewise move downwardly in the direction of arrow 925.

Referring now to FIG. 48, since the proximal body adaptor sleeve 986 is threadably engaged to the distal stem 818, the distal stem 818 moves upwardly into the direction of arrow 931 as the nut 970 and drive shaft 974 are rotated.

As shown in FIG. 40, the torque wrench 938 is used to limit the force placed upon the nut 970 and correspondingly on the distal body adaptor stem 986, the torque wrench 938 eventually limits the force placed on the distal stem 818 of the prosthesis 816.

Figure 52:
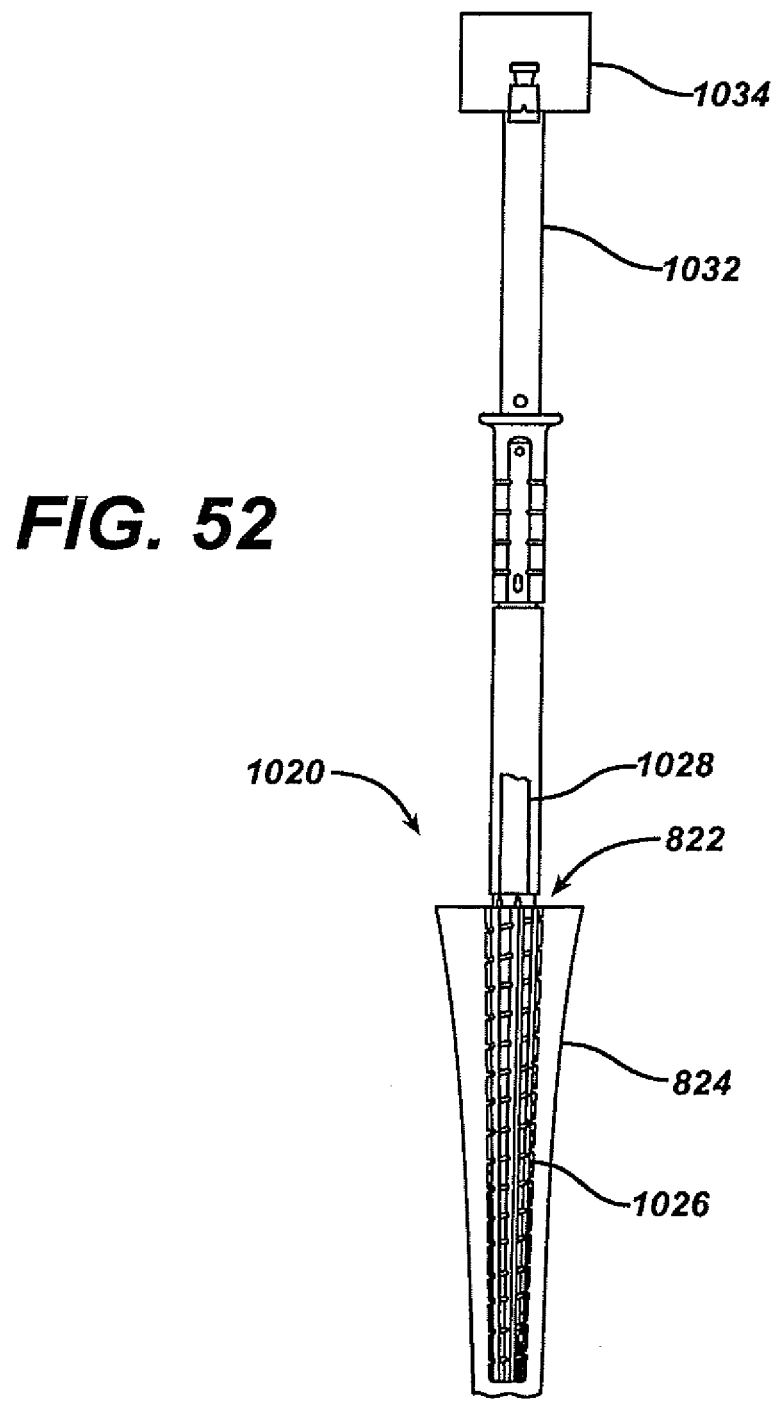
FIG. 52 is a plan view of a unitary reamer for use to prepare a cavity in a long bone for the insertion of an implant that may be assembled with assembly tool of FIG. 37.

Referring now to FIG. 52, an unitary, fixed or straight reamer 1020 is shown for use to prepare the cavity 822 of the long bone 824 for insertion of the implant that may be assembled with the assembly tool of FIG. 31. The fixed reamer 1020 includes, as is shown in FIG. 52, a reamer cutting portion 1026 which engages bone in the cavity 822 of the long bone or femur 824. The fixed reamer 1020 also includes a reamer stem 1028 extending from the reamer cutting portion 1026. A reamer driver 1032 engages the reamer stem 1028 and is used for connection to a driving device 1034.

Figure 53:
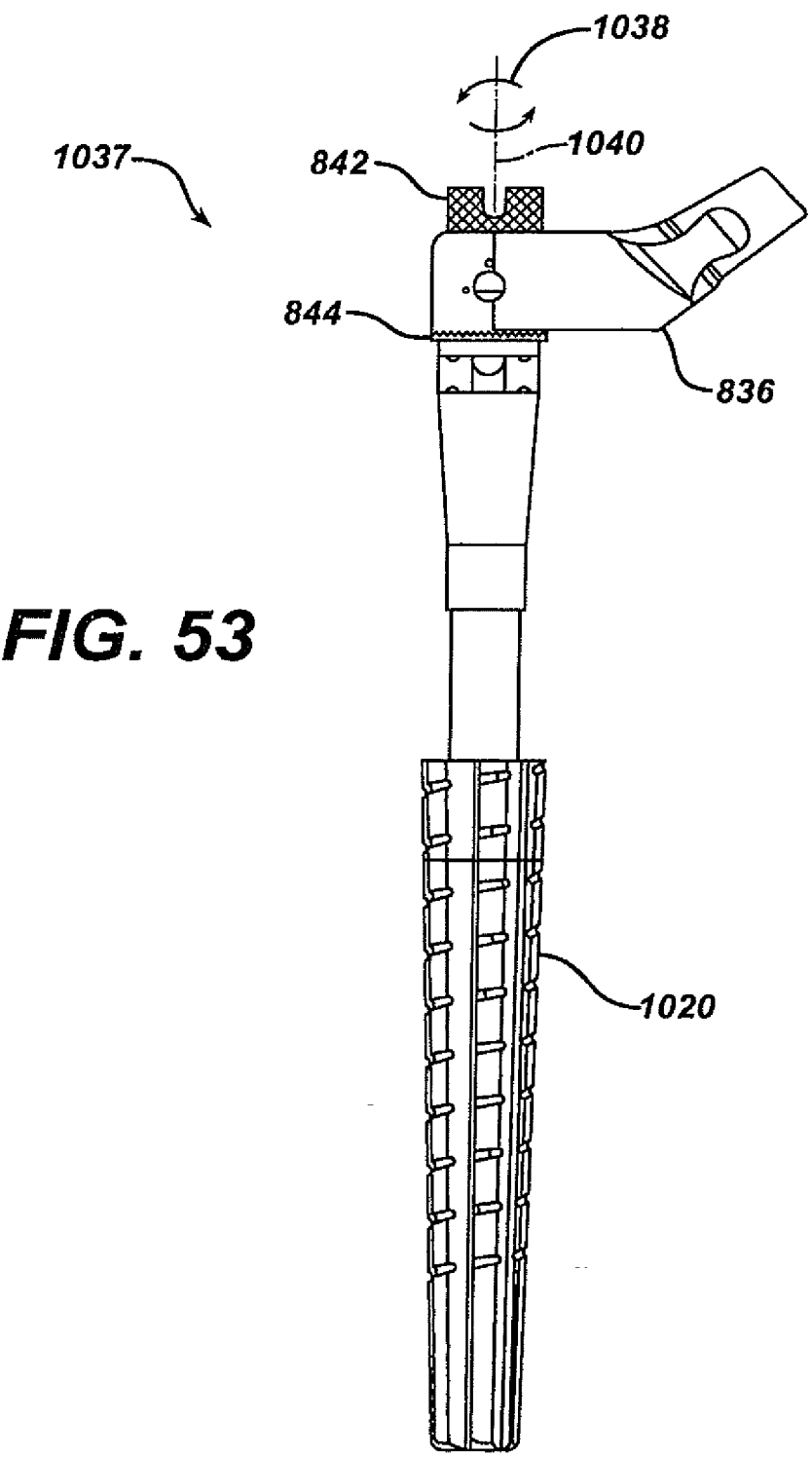
FIG. 53 is a plan view of a proximal body trial in position on the unitary reamer of FIG. 52 for use with an implant that may be assembled with the assembly tool of FIG. 37.

Referring now to FIG. 53, a proximal body trial fixed reamer assembly 1037 is shown. The assembly 1037 includes the proximal body trial 836 of FIG. 33 installed in position on the fixed reamer 1020 of FIG. 52 for use with an implant the may be assembled with the assembly tool of FIG. 31.

The angular orientation of the proximal body trial 836 may be varied around longitudinal axis 1040 in the directions of arrows 1038. A nut 842 may be loosened on the proximal body trial 836 and the teeth 844 on trial 836 may be used to indicate a finite angular motion about the longitudinal axis 1040. For example, if the trial 836 has 24 teeth on the proximal body trial 836, each tooth may represent a motion of for example, 15 degrees.

Figure 54:
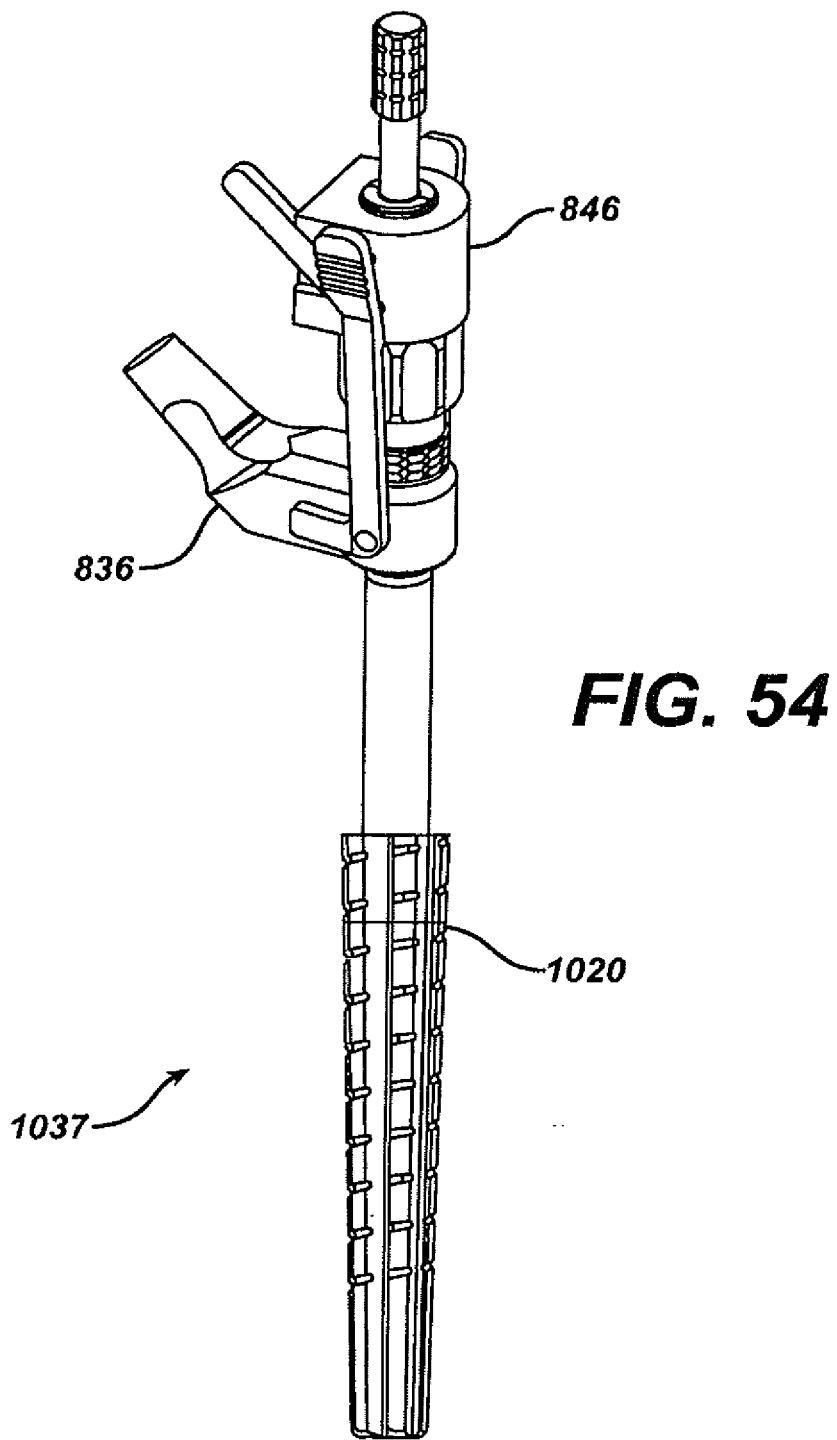
FIG. 54 is a perspective view of the proximal body/unitary reamer assembly of FIG. 53 in cooperation with the alignment tool of FIG. 33, the proximal body/unitary reamer assembly for use with an implant that may be assembled with the assembly tool of FIG. 37.

Once the proper alignment is determined by trialing of the proximal body 836 with regard to the straight or fixed reamer 1020, referring now to FIG. 54, the next step is performed. The alignment tool 846 of FIG. 34 may be positioned on the proximal body trial 836 of FIG. 33 to determine and record the proper alignment of the distal stem or fixed reamer 1020 with respect to the proximal body trial 836.

Figure 55:
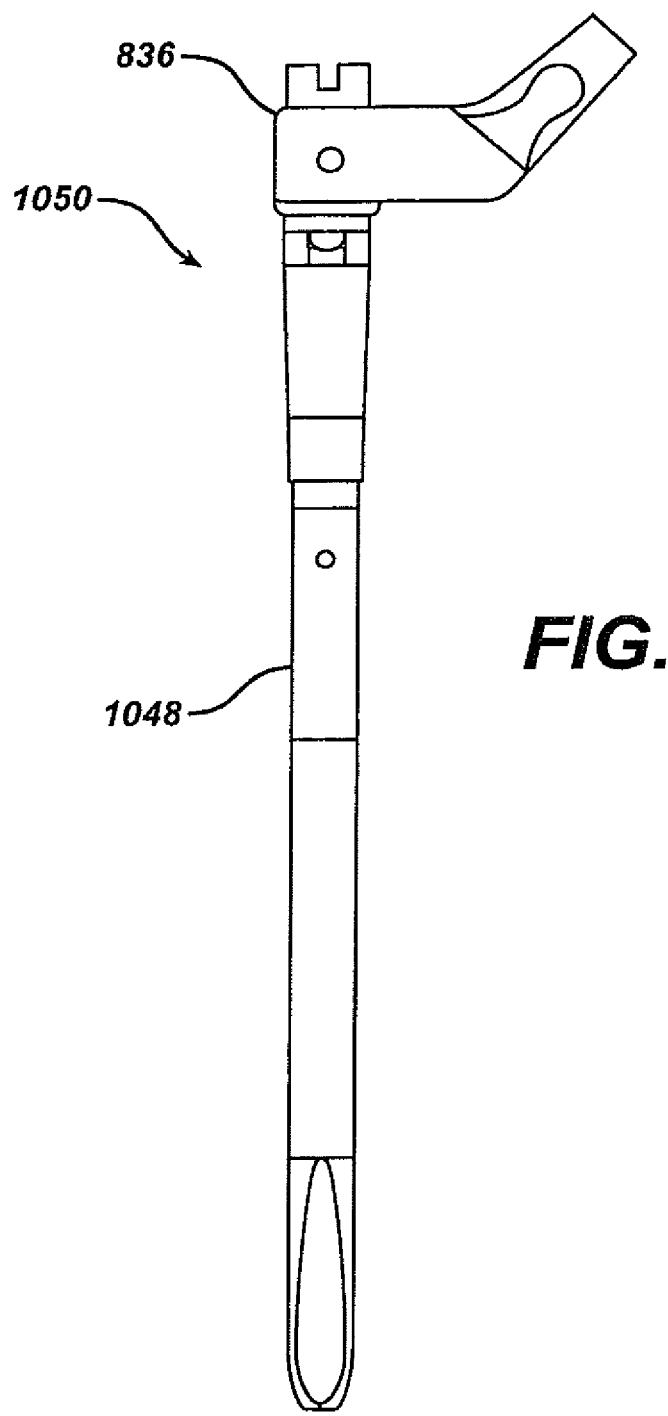
FIG. 55 is a plan view of a proximal body/straight distal stem trial assembly for use with an implant that may be assembled with the assembly tool of FIG. 37.

Referring now to FIG. 55, a trial assembly 1050 is shown for use with an implant that may be assembled with assembly tool of FIG. 31. The trial assembly 1050 may include a straight distal trial 1048 secured to the proximal body trial 836 of FIG. 33.

Figure 56:
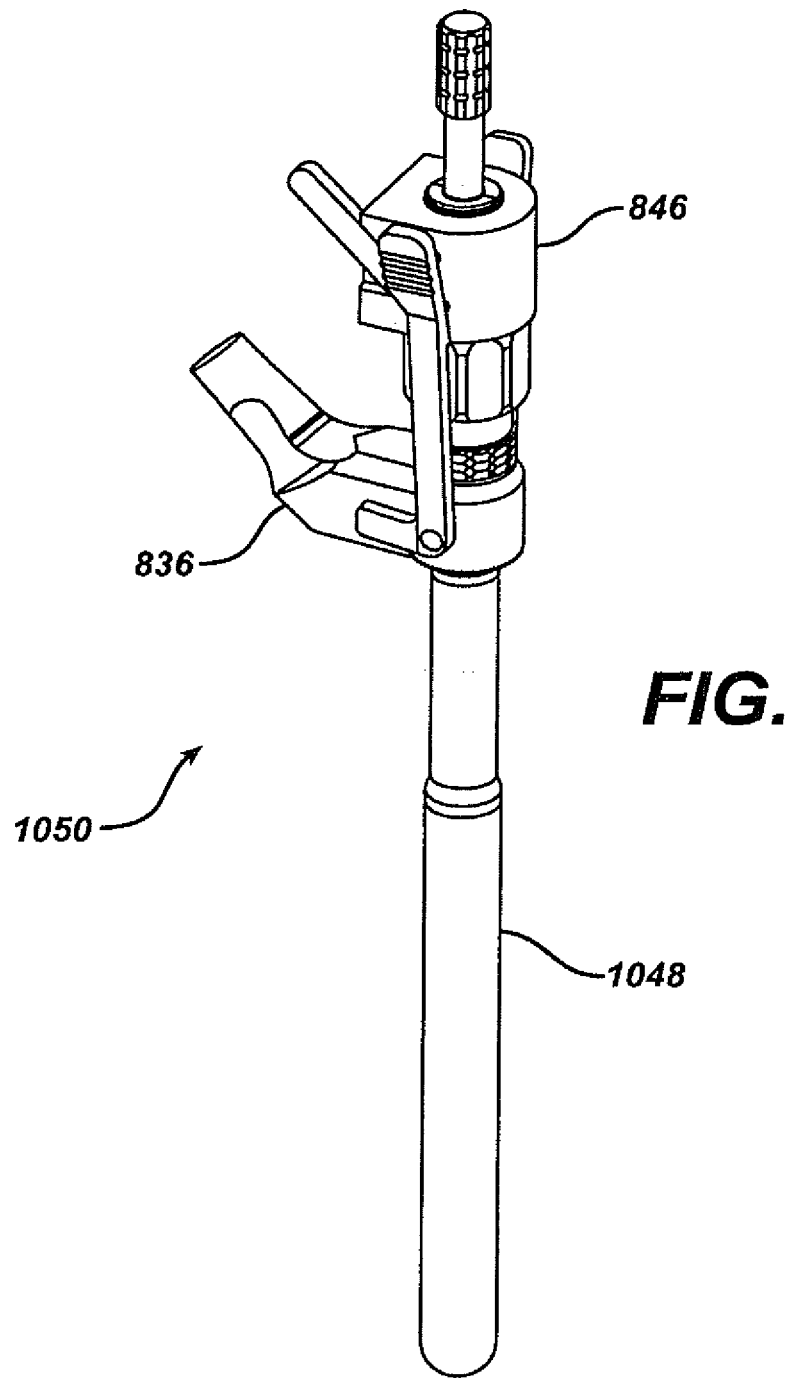
FIG. 56 is a perspective view of the proximal body/straight distal stem trial assembly of FIG. 55 in cooperation with the alignment tool of FIG. 33, the proximal body/straight distal stem trial assembly for use with an implant that may be assembled with the assembly tool of FIG. 37.

Referring now to FIG. 56, the trial assembly 1050 of FIG. 55 is shown with the alignment tool 846 of FIG. 34 positioned on the proximal body trial 836. It should be appreciated that the use of the proximal body 836 may be eliminated and the trialing may be made solely from reamers and distal implants.

Figure 57:
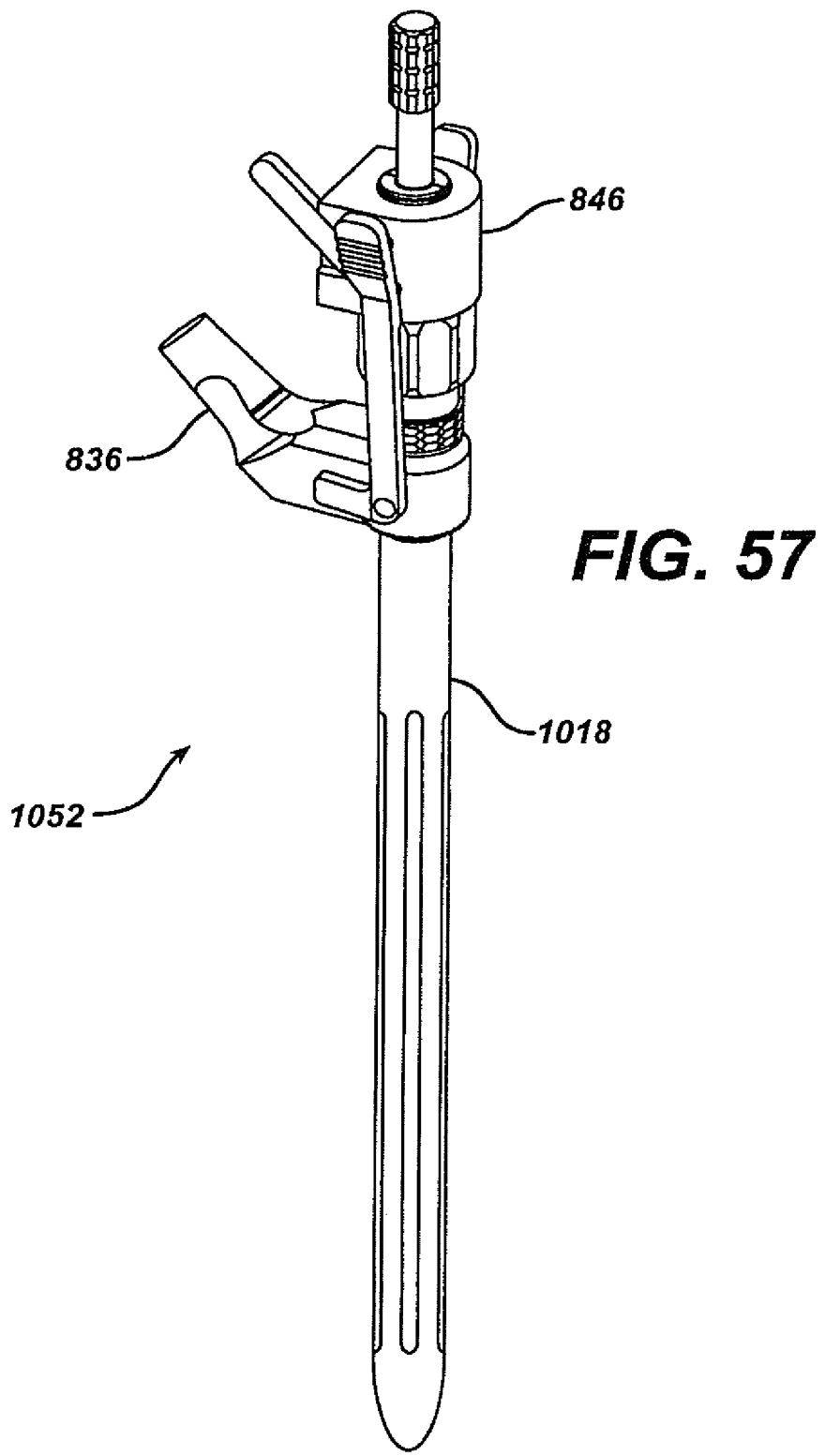
FIG. 57 is a perspective view of a proximal neck trial/straight distal stem implant assembly in cooperation with the alignment tool of FIG. 33, the proximal body trial/arcuate distal stem implant assembly for use with an implant that may be assembled with the assembly tool of FIG. 37.

Referring now to FIG. 57, a trial implant assembly 1052 is shown for use with an implant that may be assembled with the assembly tool of the present invention. For example and is shown in FIG. 57, the trial implant assembly 1052 includes a straight distal stem implant 1018 to which proximal body trial 836 of FIG. 33 may be assembled. The alignment tool 846 of FIG. 34 may be utilized to determine the angle orientation of the proximal body trial 836 with respect to the straight distal implant 1018.

Figure 58:
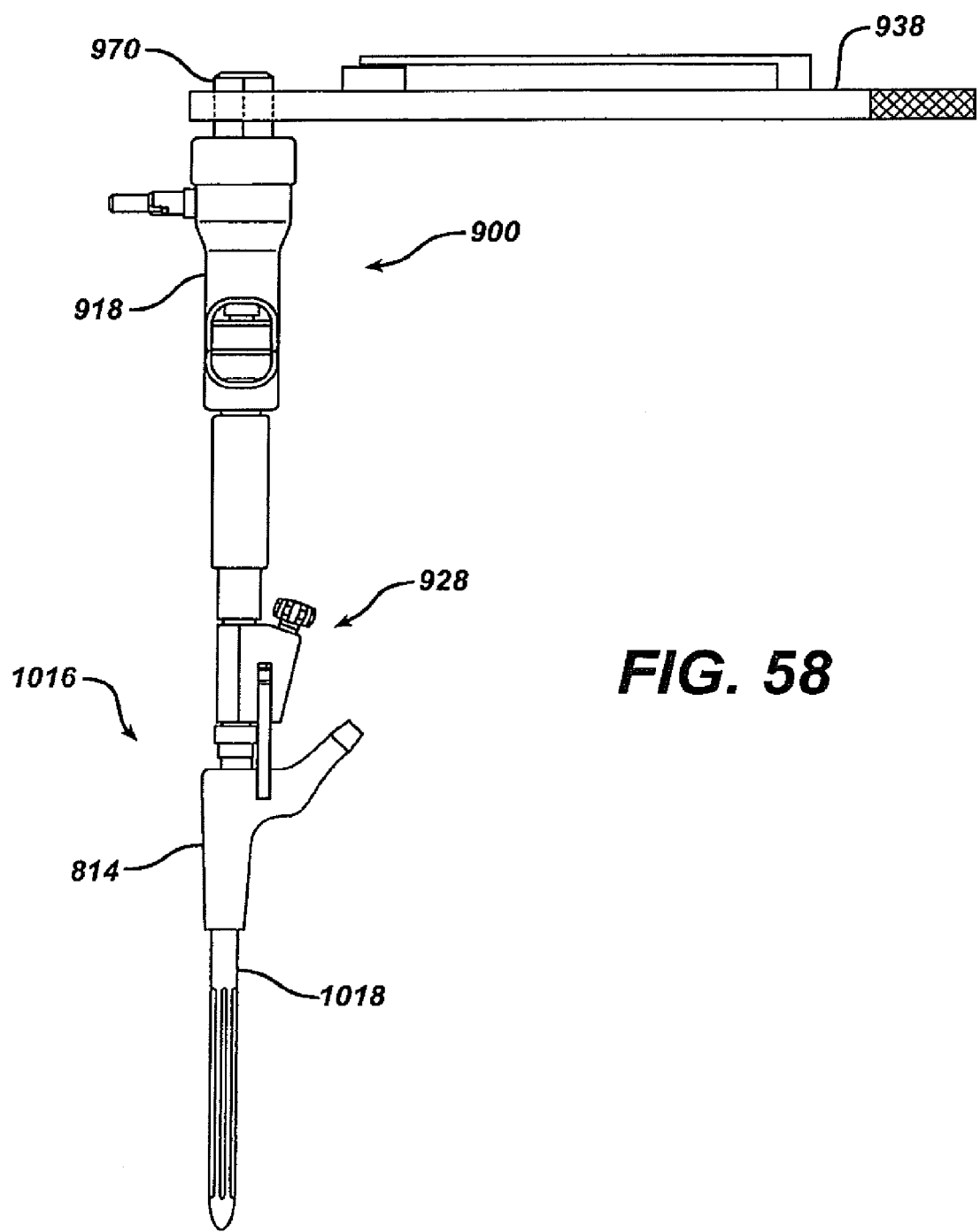
FIG. 58 is a plan view of a proximal body implant/straight distal stem implant assembly in cooperation with the assembly tool of FIG. 37.

Referring now to FIG. 58 implant assembly 1016 is shown for use with assembly tool with alignment feature 900 of FIG. 31. The implant assembly 1016 includes the straight distal stem implant 1018 of FIG. 57 secured to proximal body 814 of FIG. 38. The angular orientor 928 of the assembly tool 900 is secured to proximal body 814 of the implant assembly 1016. The torque wrench 938 is secured to nut 970.

Figure 59:
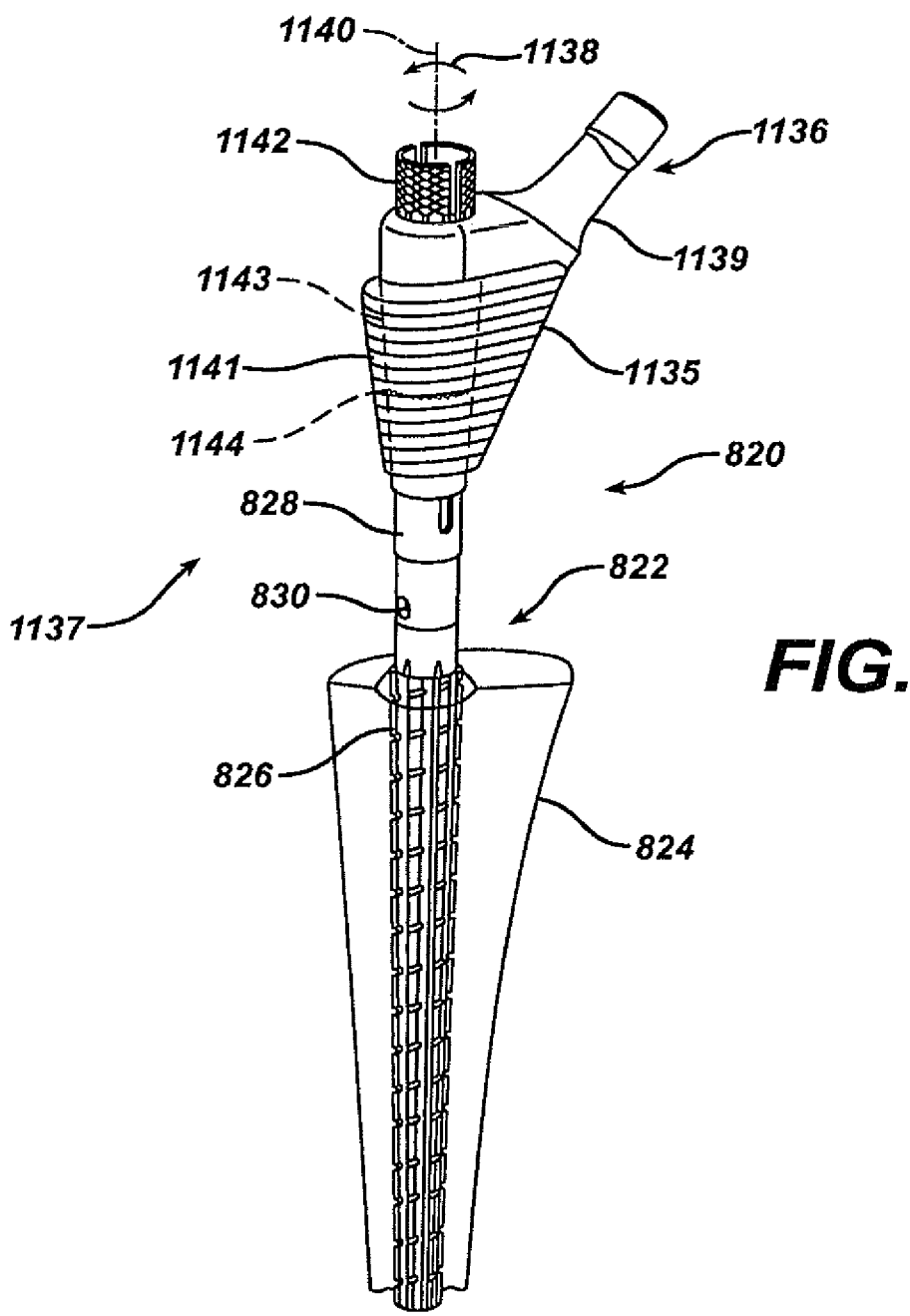
FIG. 59 is a plan view of a proximal body trial with a proximal body sleeve in position on the articulating reamer of FIG. 31 for use with an implant that may be assembled with the assembly tool of FIG. 37.

Referring to FIG. 59, yet another trial reamer assembly is shown as trial assembly 1137. The trial reamer assembly 1137 of FIG. 59 includes the articulating reamer 820 of FIG. 32 to which, a proximal body trial 1136 is attached. The proximal body trial 1136 includes a neck portion 1139 including an external taper 1141 to which internal taper 1143 of a proximal sleeve trial 1135 is matingly fitted forming trial assembly 1137. The proximal sleeve trial 1135 is used to provide additional proximal support for the trial 1136. The angular orientation of the body portion 1139 of the assembly 1137 may be angularly adjusted along longitudinal axis 1140 by rotating the neck portion 1139 about longitudinal axis 1140 in direction of the arrows 1138. A nut 1142 may be rotated to loosen the teeth 1144 of the body portion 1138. As the teeth 1144 are allowed to disengage, one tooth spacing, the proximal body trial 1136 may rotate relative to the articulating reamer 840.

Figure 60:
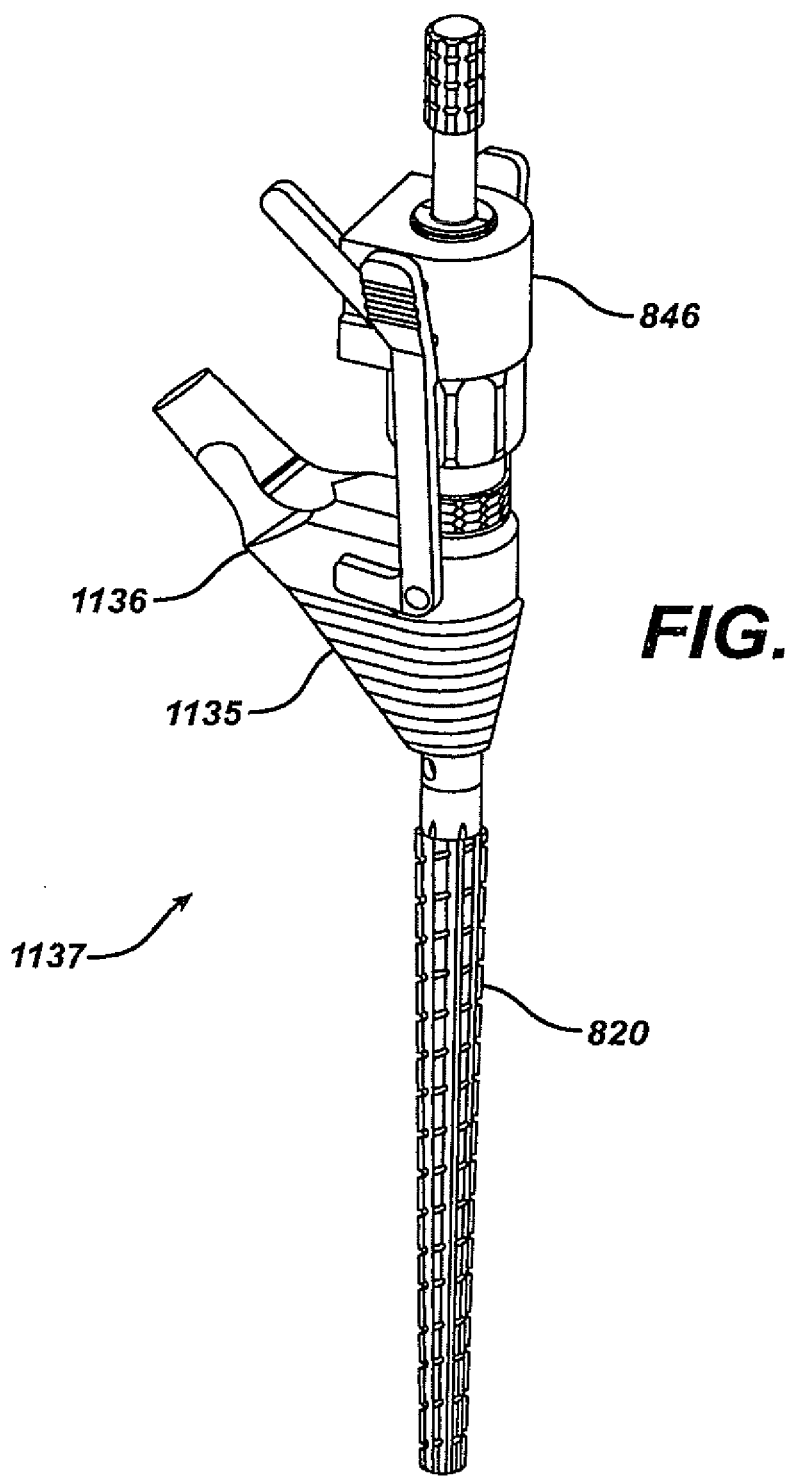
FIG. 60 is a perspective view of the proximal neck trial with a proximal body sleeve/articulating reamer assembly of FIG. 59 in cooperation with the alignment tool of FIG. 33, the proximal body trial with a proximal body sleeve/articulating reamer assembly for use with an implant that may be assembled with the assembly tool of FIG. 37.

Referring now to FIG. 60, the proximal body trial articulating reamer assembly 1137 is shown with alignment tool 846 of FIG. 34 in position on proximal body trial 1136. Alignment tool 846 is utilized to measure the angular orientation of the proximal body trial 1146 with respect to the articulating reamer 820.

Figure 61:
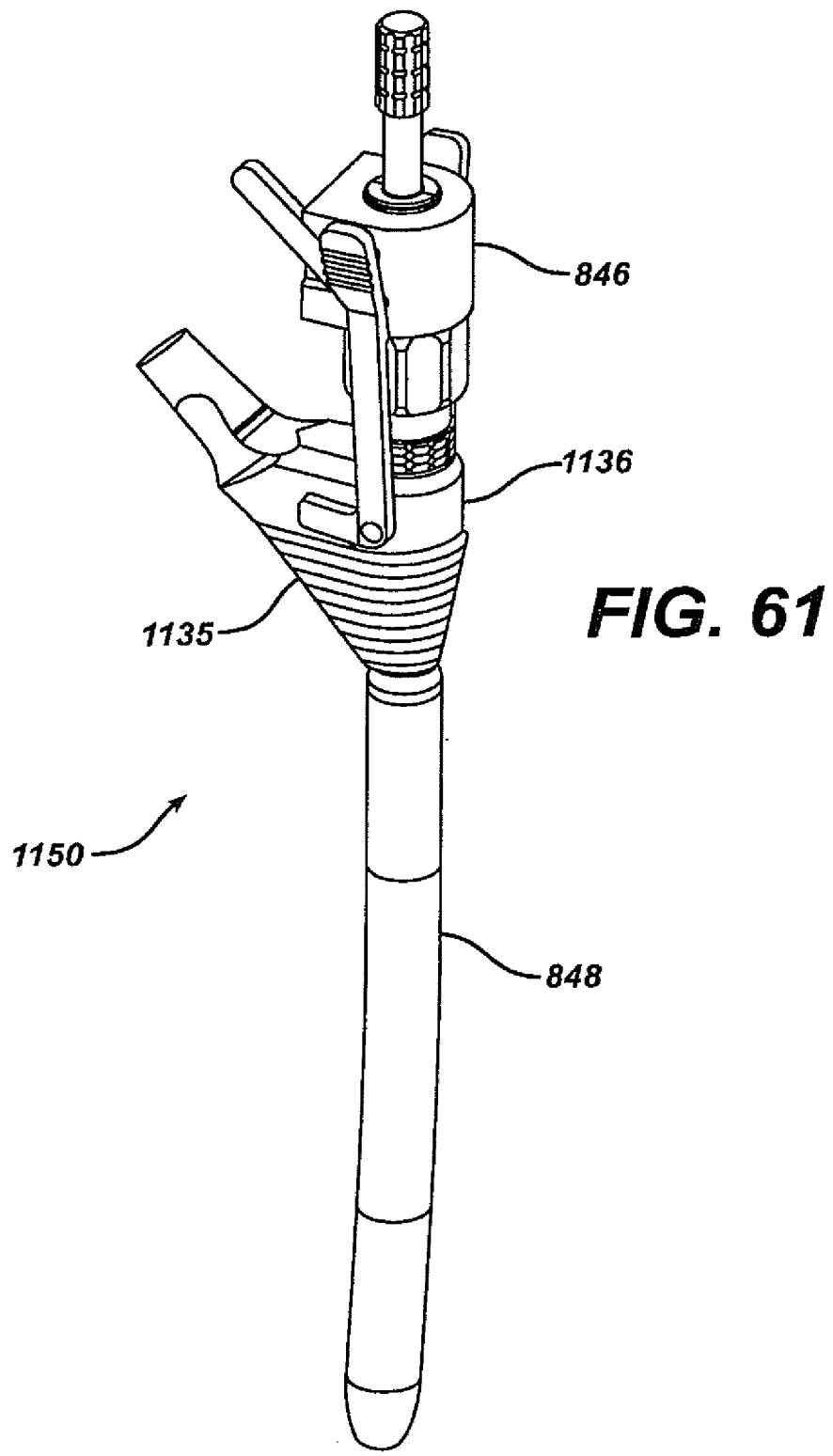
FIG. 61 is a plan view of a proximal body with a proximal body sleeve/arcuate distal stem trial assembly for use with an implant that may be assembled with the assembly tool of FIG. 37.
Figure 62:
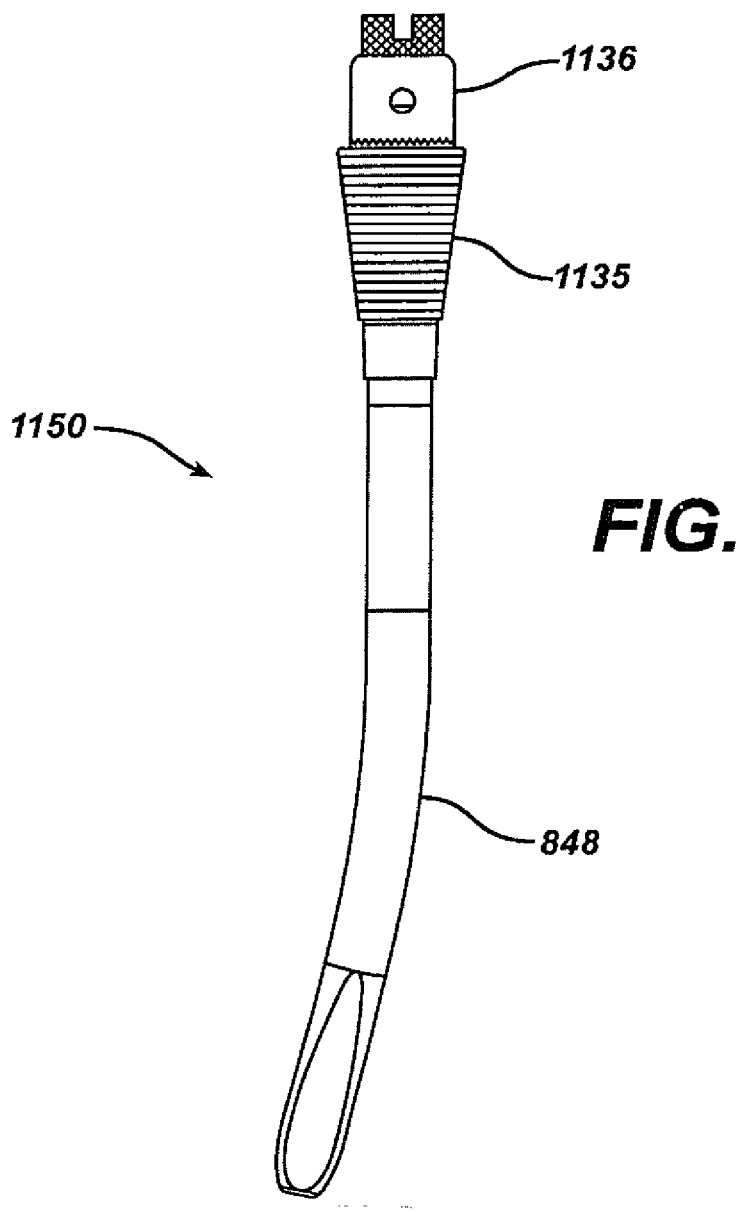
FIG. 62 is a plan view of the proximal body with a proximal body sleeve/arcuate distal stem trial assembly of FIG. 61 in cooperation with the alignment tool of FIG. 33, the proximal body with a proximal body sleeve/arcuate distal stem trial assembly for use with an implant that may be assembled with the assembly tool of FIG. 37.

Referring now to FIGS. 61 and 62, the trial assembly 1160 is shown. The trial assembly 1150 include the arcuate distal trial 848 of FIG. 35 with the proximal body trial 1136 and proximal sleeve trial 1135 in position on the distal trial 848. It should be appreciated that the use of distal trial 848 may be avoided.

Figure 63:
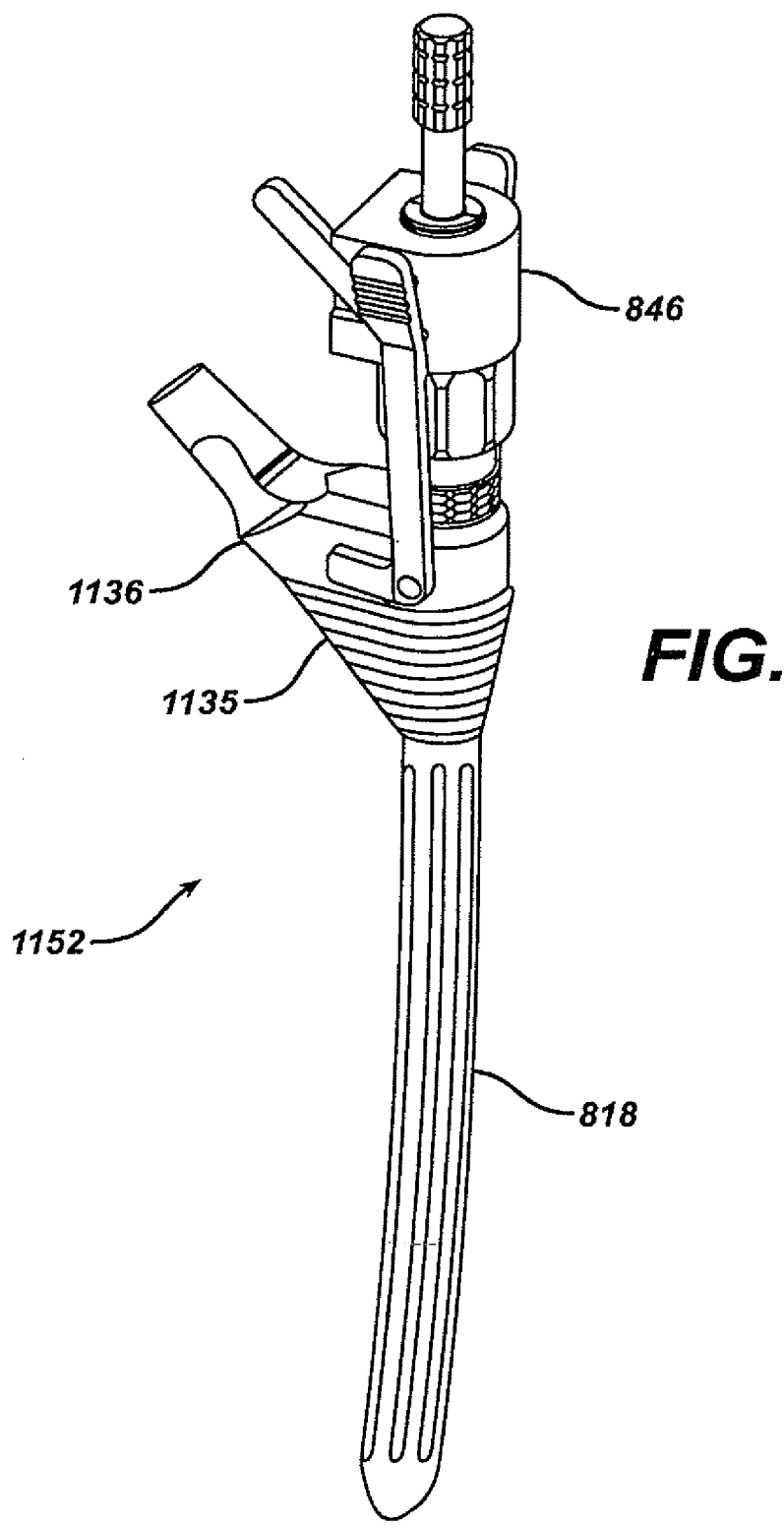
FIG. 63 is a perspective view of a proximal body trial with a proximal body sleeve/arcuate distal stem implant assembly in cooperation with the alignment tool of FIG. 33, the proximal body trial/arcuate distal stem implant assembly for use with an implant that may be assembled with the assembly tool of FIG. 37.

Referring now to FIG. 63, implant assembly 1152 is shown for use with an implant that may be tightened by the assembly tool of the present invention. The trial implant assembly 1152 includes the acruate distal implant 818 of FIG. 37 with the proximal body trial 1136 and the proximal sleeve trial 1135 in position on the acruate distal implant 818. The alignment tool 846 of FIG. 34 may be utilized to measure the angular orientation of the proximal body trial with respect to the acruate distal implant 818.

Figure 64:
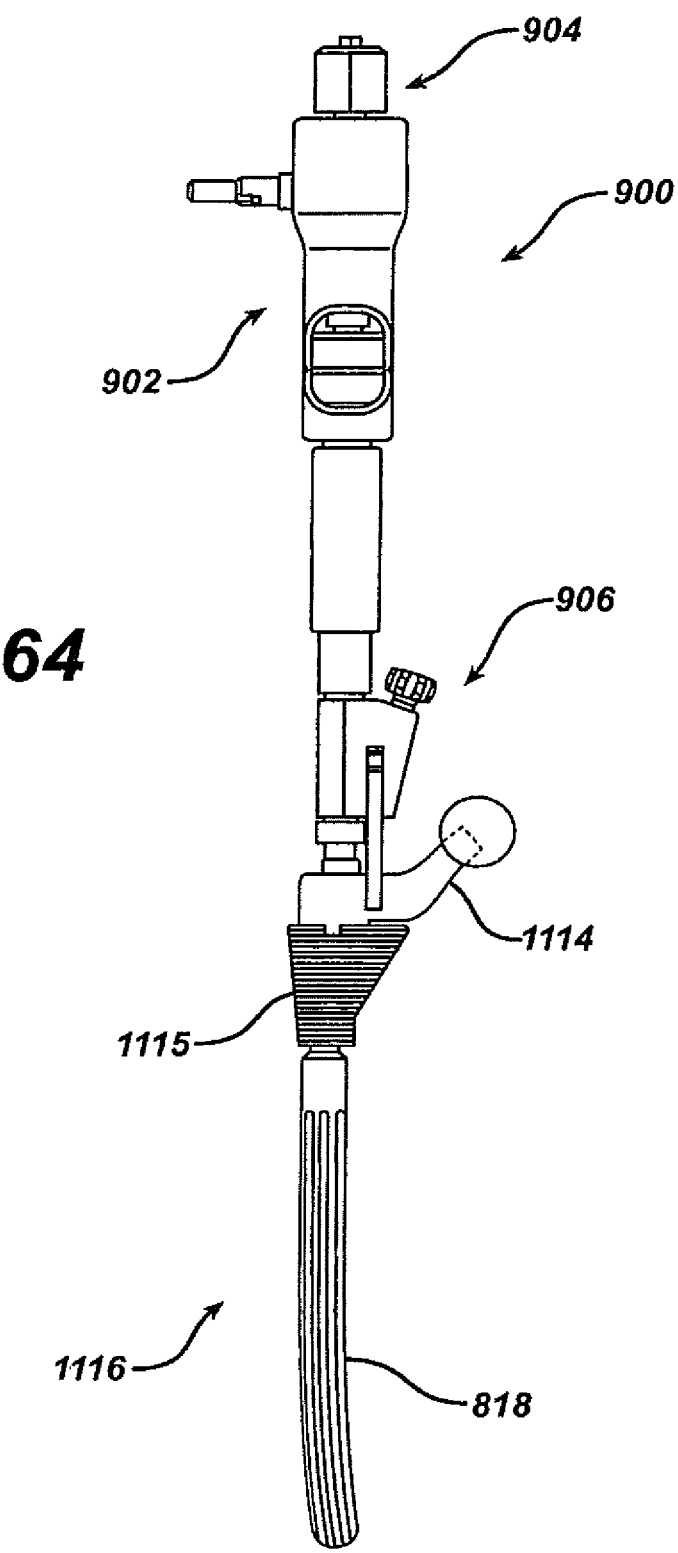
FIG. 64 is a plan view of a proximal body implant with a proximal body sleeve/arcuate distal stem implant assembly in cooperation with the assembly tool of FIG. 37.

Referring now to FIG. 64, the assembly alignment tool 900 of the present invention is shown in position on implant assembly 1116. The implant assembly 1116 includes the acruate distal stem implant 818 of FIG. 37 to which proximal body implant 1114 is secured. A proximal body sleeve 1115 is positioned between the proximal body 1114 and the acruate distal stem 818. The assembly/alignment tool 900 may be used to align and tighten as well as to disassemble the proximal body implant to the distal stem implant 818.

Figure 65:
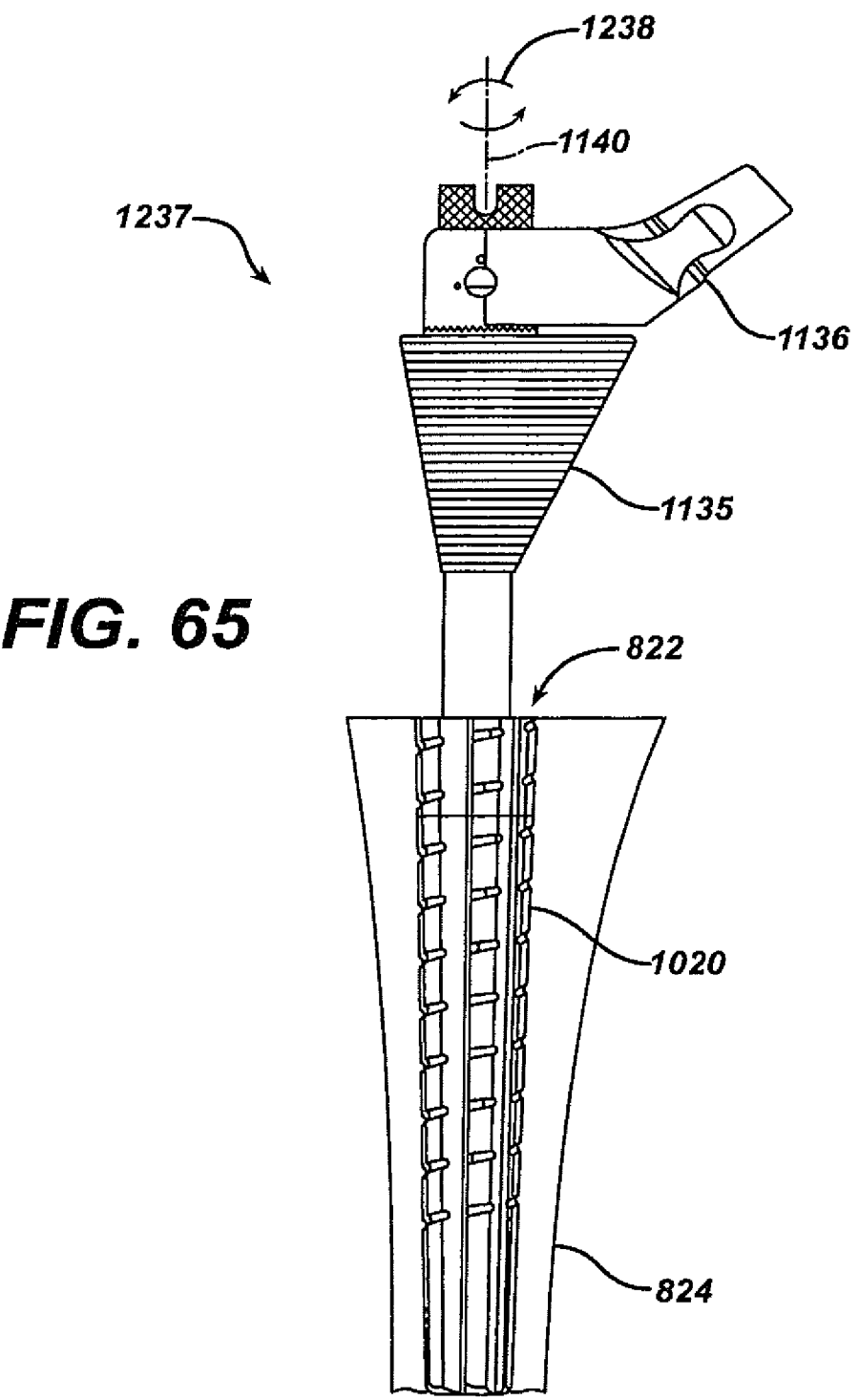
FIG. 65 is a plan view of a proximal body trial with a proximal body sleeve in position on the unitary reamer of FIG. 52 for use with an implant that may be assembled with the assembly tool of FIG. 37.

Referring now to FIG. 65, yet another proximal body trial reamer assembly is shown which may be utilized with an implant that may be tightened with an assembly alignment tool of the present invention. For example and is shown in FIG. 65, a proximal body trial/straight reamer assembly 1237 is shown. The assembly 1237 includes the straight reamer 1020 of FIG. 52 to which proximal body trial 1136 and proximal sleeve trial 1135 of FIG. 59 is secured. The proximal body trial 1136 may be rotated with respect to the straight reamer 1020 about longitudinal axis 1140 in the direction of arrows 1238.

Figure 66:
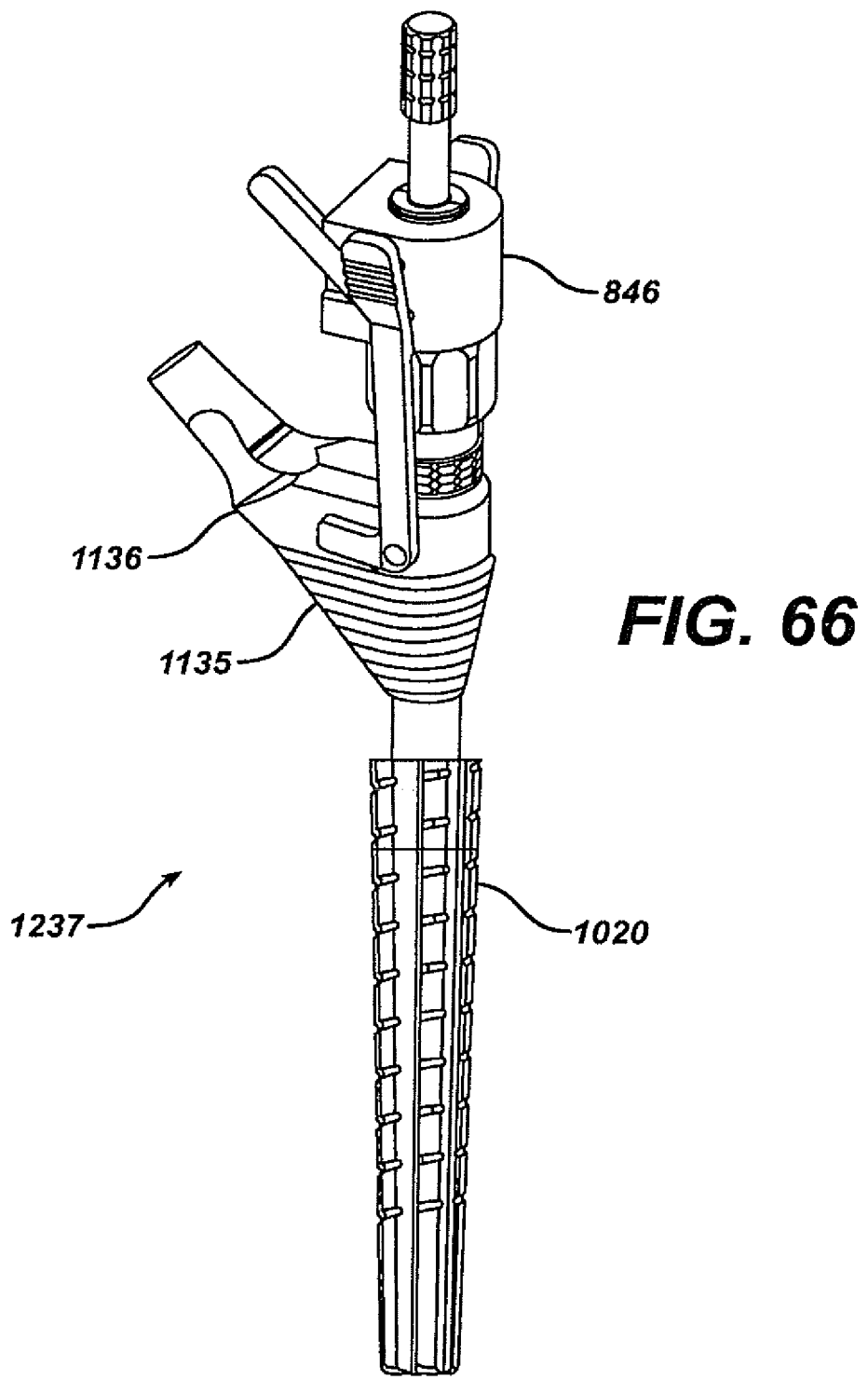
FIG. 66 is a perspective view of the proximal body with a proximal body sleeve/unitary reamer assembly of FIG. 53 in cooperation with the alignment tool of FIG. 33, the proximal body with a proximal body sleeve/straight reamer assembly for use with an implant that may be assembled with the assembly tool of FIG. 37.

Referring now to FIG. 66, the proximal body/trial straight reamer assembly 1237 of FIG. 65 is shown with alignment tool 846 of FIG. 34 in position on the proximal body trial 1136 of the trial straight reamer assembly 1237.

Figure 67:
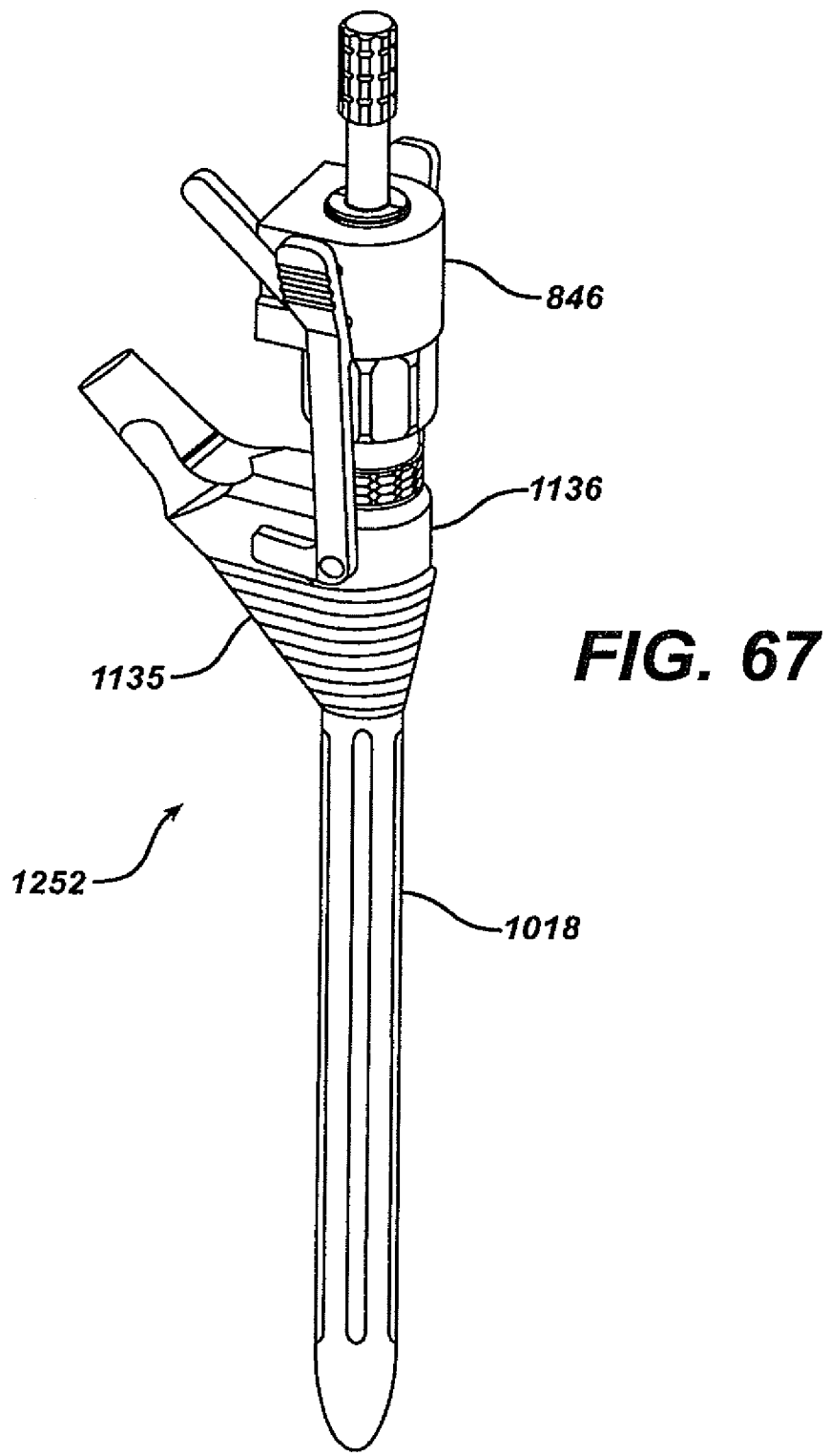
FIG. 67 is a plan view of a proximal body with a proximal body sleeve/straight distal stem trial assembly for use with an implant that may be assembled with the assembly tool of FIG. 37.

Referring now to FIG. 67, a trial implant assembly 1252 is shown for use with an implant assembly that may be assembled with the assembly alignment tool of the present invention. The trial implant assembly 1252 includes the straight distal implant 1118 of FIG. 57 to which proximal body trial 1136 of FIG. 59 is secured. Proximal sleeve 1135 of FIG. 59 is positioned between the straight distal implant 1118 and the proximal body trial 1136. Alignment tool 846 of FIG. 34 may be utilized to angular orient or to measure the angle of orientation of the proximal body trial 1136 to the straight distal implant 1118.

Figure 68:
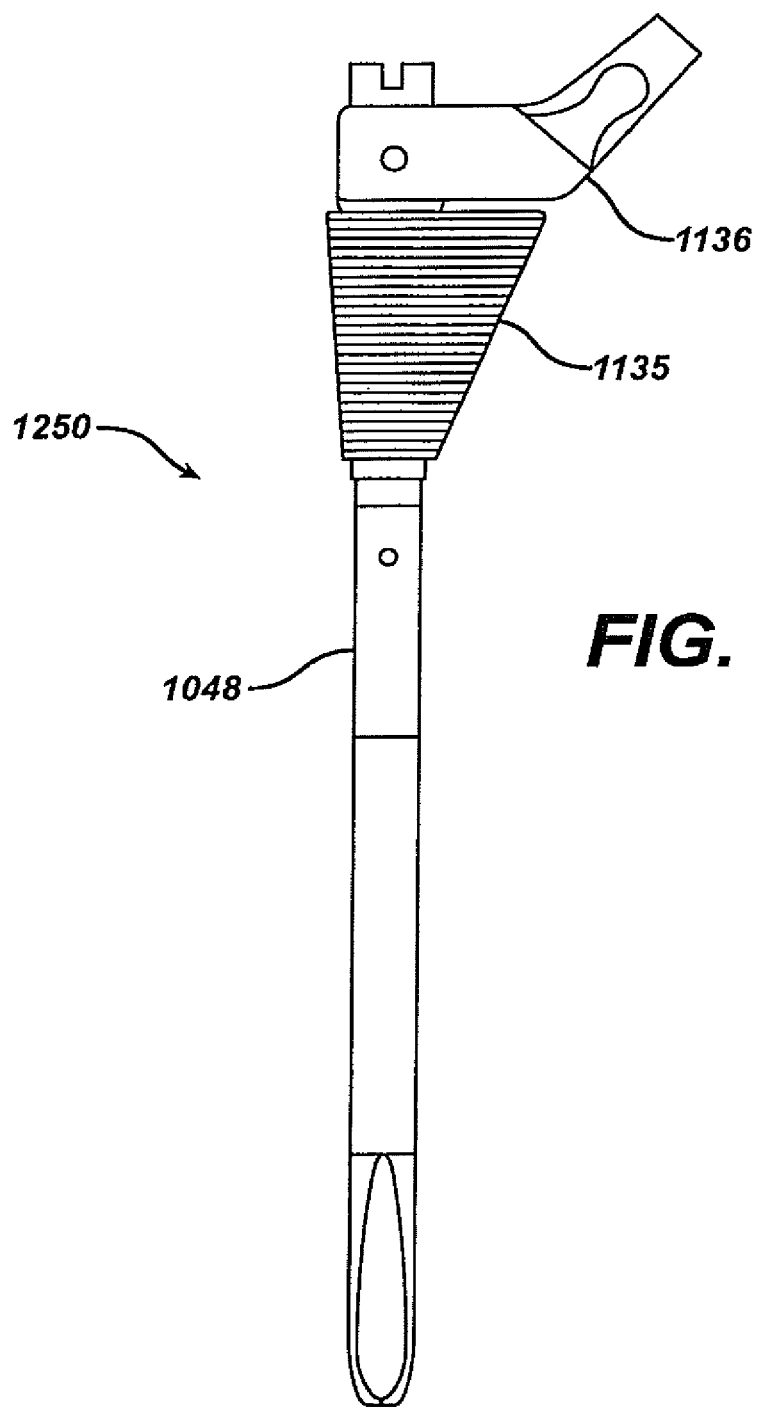
FIG. 68 is a perspective view of the proximal body with a proximal body sleeve/straight distal stem trial assembly of FIG. 55 in cooperation with the alignment tool of FIG. 33, the proximal body with a proximal body sleeve/straight distal stem trial assembly for use with an implant that may be assembled with the assembly tool of FIG. 37.

Referring now to FIG. 68, trial assembly 1250 is shown for use with an implant that may be assembled using the assembly and alignment tool of the present invention. The trial assembly 1250 includes the straight distal trial 1048 of FIG. 55 to which body trial 1136 of FIG. 59 is secure. Proximal sleeve trial 1135 of FIG. 59 may be positioned between the proximal body trial 1136 and the straight distal stem trial 1148.

Figure 69:
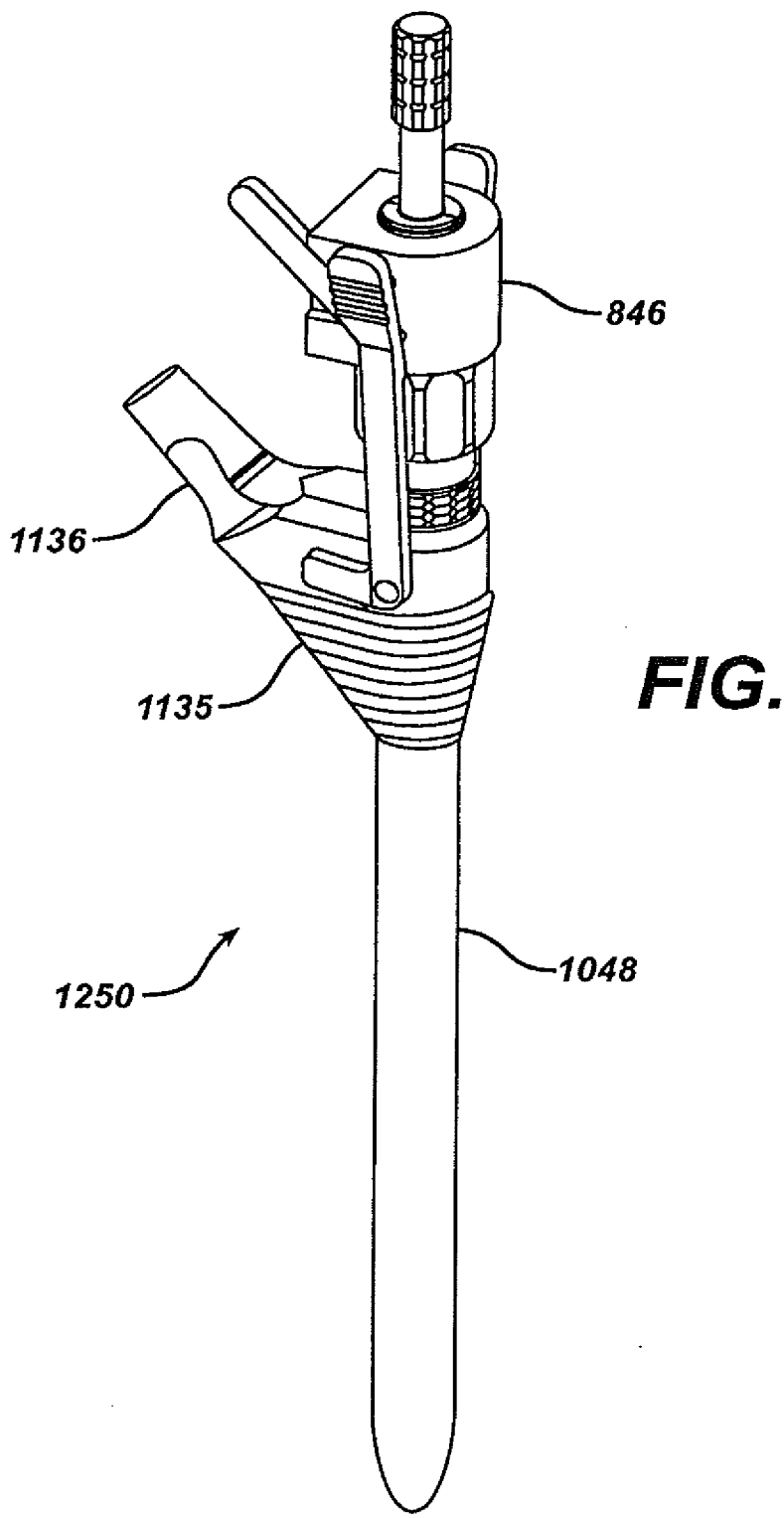
FIG. 69 is a perspective view of a proximal body trial with a proximal body sleeve/straight distal stem implant assembly in cooperation with the alignment tool of FIG. 33, the proximal body trial with a proximal body sleeve/arcuate distal stem implant assembly for use with an implant that may be assembled with the assembly tool of FIG. 37.

Referring now to FIG. 69, alignment tool 846 of FIG. 34 is shown in position on trial assembly 1250 of FIG. 68. The trial assembly 1250 includes a proximal body trial 1136 to which the straight distal stem trial 1048 is positioned. It should be appreciated that the distal trial 1048 may be avoided.

Figure 70:
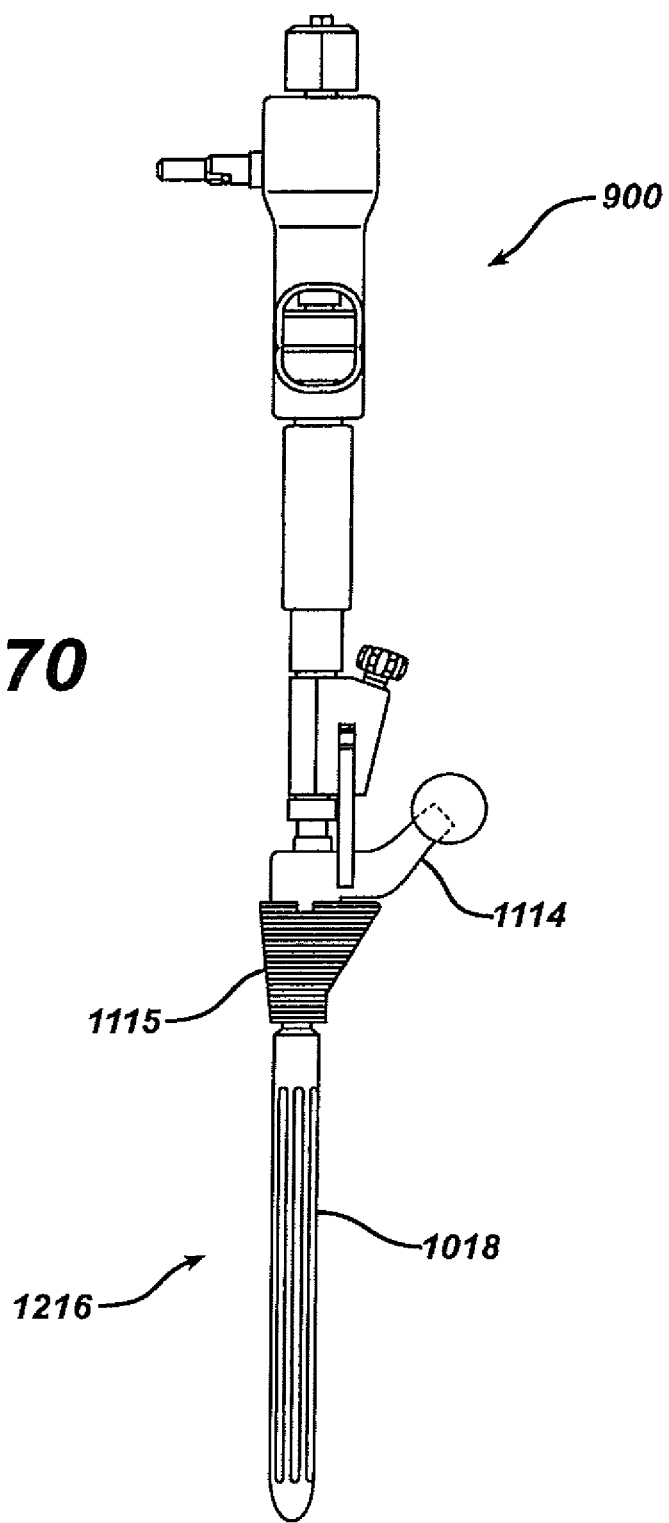
FIG. 70 is a plan view of a proximal body implant with a proximal body sleeve/straight distal stem implant assembly in cooperation with the assembly tool of FIG. 37.

Referring now to FIG. 70, implant assembly 1216 is shown for use in assembly/alignment tool 900 of FIG. 31.

The implant assembly includes the implant straight distal stem 1018 of FIG. 58 to which implant proximal body 1114 of FIG. 64 is attached. The implant proximal sleeve 1115 of FIG. 64 is positioned between the proximal body 1114 and the implant straight distal stem 1118.

Referring now to FIG. 71, a method 1300 for performing orthopaedic surgery is shown. The method includes a first step 1310 of providing a prosthesis including a first component and a second component removably attached to the first component. The method includes a second step 1312 of providing an instrument that has a first member operably associated with the first component. The first member includes a first member relative motion feature and a body defining a generally cylindrical longitudinal opening in the body.

The instrument also includes a second member operably associated with the second component. The second member is operably associated with the first member for relative motion between the first member and second member for assembly of the first component of the prosthesis to the second component.

The instrument further includes an angular orientation feature cooperating with the first member and the second member for replicating and or measuring the relative angular orientation of the first component with respect to the second component.

The method 1300 further includes a third step 1314 of assembling the first component to the second component. The method 1300 further includes a fourth step 1316 of connecting the first member of the tool to the first component and a fifth step 1318 of connecting the second member of the tool to the second component. The method 1300 further includes a sixth step 1320 of rotating the first member of the tool with respect to the second member of the tool to secure the first component to the second component.

According to the present invention and referring now to FIG. 72, another embodiment of the present invention is shown as a method of performing orthopaedic surgery 1400. The method 1400 includes a first step 1410 of providing a trial prosthesis including a stem trial portion for implantation at least partially into the femoral canal of a femur and a neck trial portion extending from the stem portion. The method 1400 further includes a second step 1412 of positioning the stem trial portion in the femoral canal.

The method 1400 further includes a third step 1414 of positioning the neck trial portion relative to the stem trial portion and a fourth step 1416 of securing the neck trial portion to the stem trial portion. The method 1400 also includes a fifth step 1418 of trialing the trial prosthesis and a sixth step 1420 of attaching an instrument to the trial stem portion and a neck trial portion.

The method 1400 further includes a seventh step 1422 of measuring the relative position of the stem trial portion to the neck trial portion. The method 1400 further includes an eighth step 1424 of providing an implant prosthesis including a stem implant portion for implantation at least partially into the femoral canal of femur and a neck implant portion extending from the stem portion.

The method 1400 further includes a ninth step 1426 of providing an instrument to secure the stem implant portion to the neck implant portion while angularly orienting the stem implant portion to the neck implant portion.

Figure 73:
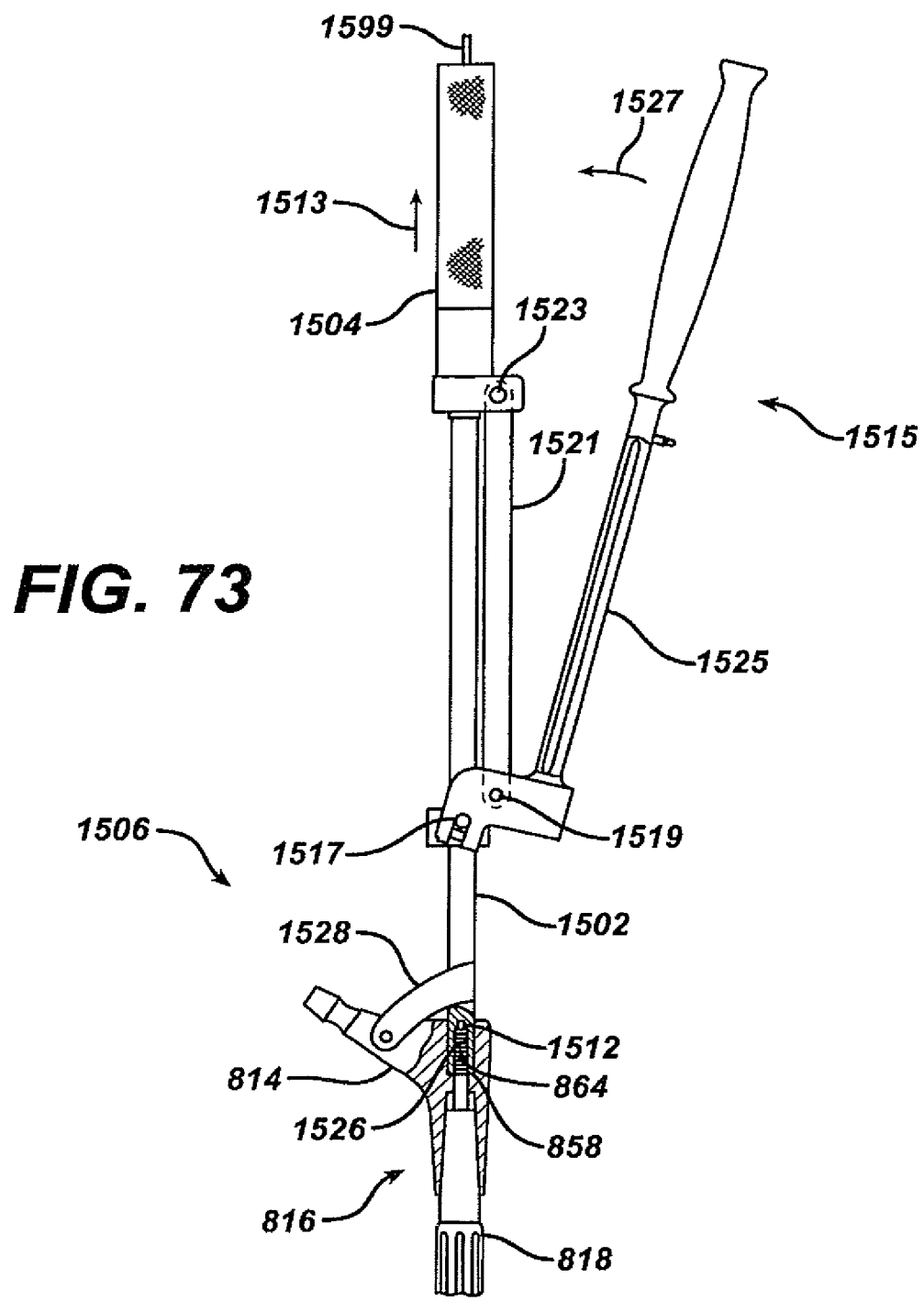
FIG. 73 is a plan view of a proximal body implant/arcuate distal stem implant assembly in cooperation with an assembly tool according to yet another embodiment of the present invention showing an assembly tool with a lever mechanism.

Referring now to FIG. 73, another embodiment of the present invention is shown as assembly tool 1500. Assembly tool 1500 is used for assembling the first component, for example, proximal body 814 of prosthesis 816 to a second component for example, distal stem 818 of the prosthesis 816 for use in joint arthoplasty. The tool 1500 includes a first member 1502 in the form of, for example, a body having a cylindrical opening.

Figure 73A:
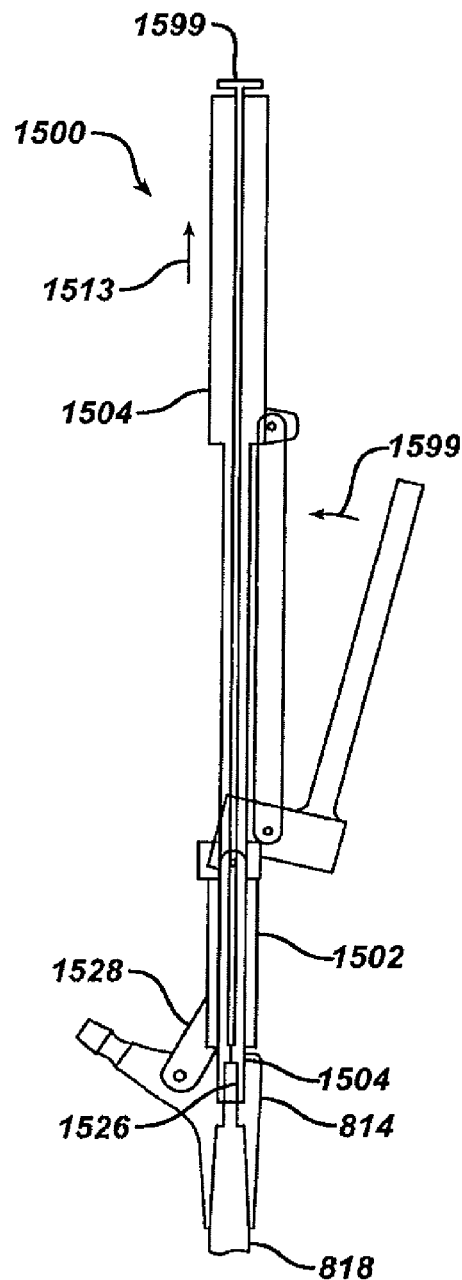
FIG. 73A is a partial plan view partially in cross section of FIG. 73 showing the actuation members in greater detail.

First member 1502 is operably associated with the proximal body 814 of the prosthesis 816. For example and is shown in FIG. 73A, a first orientor 1528 similar to the first orientor 928 of FIG. 48 of assembly tool 900 may be utilized to orient the proximal body 814 to the first member 1502 of the assembly tool 1500.

The assembly tool 1500 may further include a second member 1504. The second member 1504 is operably associated with the second component or distal stem 818. For example and is shown in FIG. 73, the second member 1504 is in the form of a tube or sleeve and is slidably fitted within the first member 1502. The second member 1504 may include internal threads 1526, which engage with external threads 858 of the distal stem 818. The first member 1502 and the second member 1504 are adapted to provide for the assembly of the proximal body 814 of the prosthesis 816 to the distal stem 818 of the prosthesis 816.

The second member 1504 is operably associated with the first member 1502 for relative motion between the first member 1502 and the second member 1504 for assembly of the first component or proximal body 814 to the distal stem or the second component 818.

The assembly tool 1500 further includes an angle orientation feature 1506. The angular orientation feature 1506 cooperates with the first member 1502 and the second member 1504 for replicating and/or measuring of the relative angular orientation of the proximal body 814 with respect to the distal stem 818.

Figure 73B:
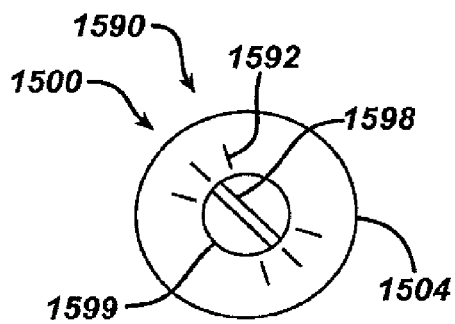
FIG. 73B is a top view of FIG. 73 showing an alignment feature in greater detail.
Figure 73C:
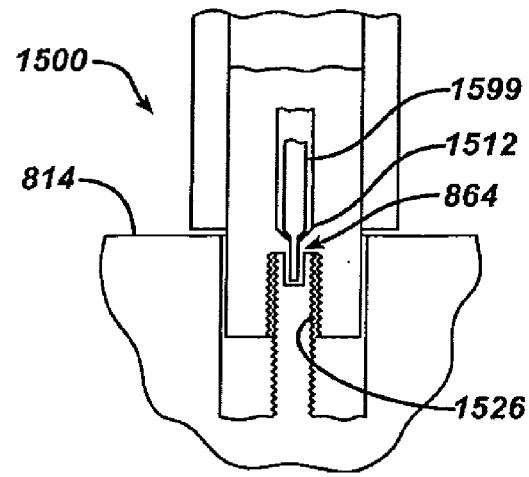
FIG. 73C is a partial plan view partially in cross section of FIG. 73 showing the attachment to the distal stem of the prosthesis in greater detail.

Referring now to FIG. 73C, the assembly tool 1500 as shown in FIG. 73 includes a central rod or central alignment stem 1599 which is slidably fitted within the second member 1504. The central alignment stem 1599 includes a second orientor or tang 1512, which engages with slot 864 formed in the distal stem 818 of the prosthesis 816.

To align the proximal body 814 to the distal stem 818, the proximal body 814 is aligned with the first member 1502 through the first orientor 1528 while the distal stem 818 is angularly oriented with respect to the alignment stem 1599 by the tang or second orientor 1512.

Referring now to FIG. 73B, radial mark 1598 located on the central alignment stem 1599 is used with marks 1592 formed on second member 1504 to combine as indicia 1590 to provide a visual representation of the angular orientation between the distal stem 818 and the proximal body 814.

Referring again to FIG. 73, to provide the axial motion of the second member 1504 in the direction of arrow 1513, a lever mechanism 1515 is attached to the first member 1502 and to the second member 1504. For example and is shown in FIG. 73, the lever mechanism 1515 includes a first pivoting position 1517 pivotally positioning the lever mechanism 1515 with respect to first member 1502. The lever mechanism 1515 further includes a second pivoting position 1519 to connect the level mechanism 1515 to a link 1521. The link 1521 is pivotally connected to the second member 1504 at a third pivoting position 1523.

Continuing to refer to FIG. 73, as lever arm 1525 of leveling mechanism 1515 is rotated in the direction of arrow 1527, the link 1521 urges second member 1504 in the direction of arrow 1513 to engage the distal stem 818 to the proximal body 814.

Referring now to FIG. 74, another embodiment of the present invention is shown as assembly tool 1600. Assembly tool 1600 is used to assemble first component for example, proximal body 814 of prosthesis 816 to second component 818 for example, distal stem 818 of the prosthesis 816 for use in joint arthoplasty. The assembly tool 1600 includes a first member 1602. The first member 1602 is operably associated with the proximal body or first component 816.

For example and is shown in FIG. 74, the first member 1602 is in the form of a cylindrical sleeve. An angular orientation feature 1606 includes as shown in FIG. 74, a first orientor 1628. The first orientor 1628 is similar to the orientor 928 of FIGS. 31-50. The first orientor 1628 physically angularly locks the proximal body 814 to the first member 1602.

The assembly tool 1600 further includes a second member 1604, that is operably associated with the second component 816. For example and is shown in FIG. 74, the second member 1604 is in the form of a tube, which is slidably fitted within the first member or sleeve 1602. The second member 1604 includes internal threads 1626, which engage with external threads 858 located on the distal stem 818. The first member 1602 and the second member 1604 are adapted to provide for the assembly of the proximal body 814 to the distal stem 818. The second member 1604 is operably associated with the first member 1602 for relative motion within the first member 1602 and the second member 1604. For example and is shown in FIG. 74, the second member 1604 is slidably fitted within the first member 1602.

As earlier discussed, the assembly tool 1600 further includes the angular orientation feature 1606. The first member 1602 defines a first member longitudinal axis 1608 and the second member 1604 defines a second member longitudinal axis 1610. The second member 1604 is adapted to provide relative motion of the second member 1604 with respect to the first member 1602 when the second member 1604 is rotated relative to the first member 1602 about the second longitudinal axis 1610. The relative motion of the second member 1604 with respect to the first member 1602 is utilized to affect the relative motion of the proximal body 814 with respect to the distal stem 818 to urge distal stem 818 into the engagement of the proximal body 814.

Figure 74A:
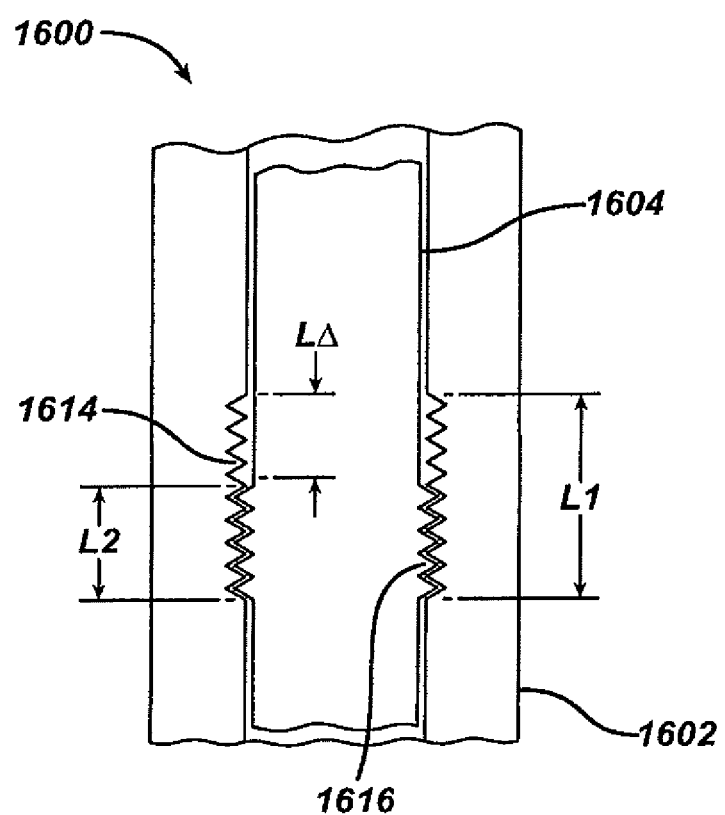
FIG. 74A is a partial plan view partially in cross section of FIG. 74 showing the cooperation of the actuation members in greater detail.

For example and is shown in FIGS. 74 and 74A, the first member 1602 includes a first member relative motion feature in the form of, for example, internal threads 1614. The second member 1604 includes a second member relative motion feature in the form of, for example, external threads 1616. The internal threads 1614 and the external threads 1616 cooperate with each other to provide the relative motion of the second member 1604 with respect to the first member 1602.

For example and is shown in FIG. 74, as nut 1670 located on the end of second member 1604 is rotated, the second member 1604 is rotated relative to the first member 1602. Because of the internal threads 1614 and external threads 1614, the second member 1614 advances in the direction of arrow 1613.

As shown in FIGS. 74 and 74A, the internal threads 1614 on the first member 1602 extend a length L1, which is greater than the distance L2 that external threads 1616 of the second member 1604 extend. The difference between the length L2 and L1 represents L Δ or amount of motion along longitudinal axis 1608 that the second member 1604 may move relative to the first member 1602.

Continuing to refer to FIG. 74, the angular orientation feature 1606 includes first orientor 1628 as well as second orientor 1612. The first member 1602 defines a first member longitudinal axis 1608 while the second member 1604 defines second longitudinal axis 1610. The first member 1602 is rotatively secured to the proximal body or the first component 814 by the first orientor 1628. The second angular orientor or tang 1612 is rotatively keyed the second component or distal stem 818 by slot 864 in the distal stem 818. The relative angular position of the proximal body 814 with respect to the distal stem 818 about longitudinal axis 1608 corresponds to the angular orientation of the first angular orientor 1628 with respect to the second angular orientor or tang 1612.

Figure 75:
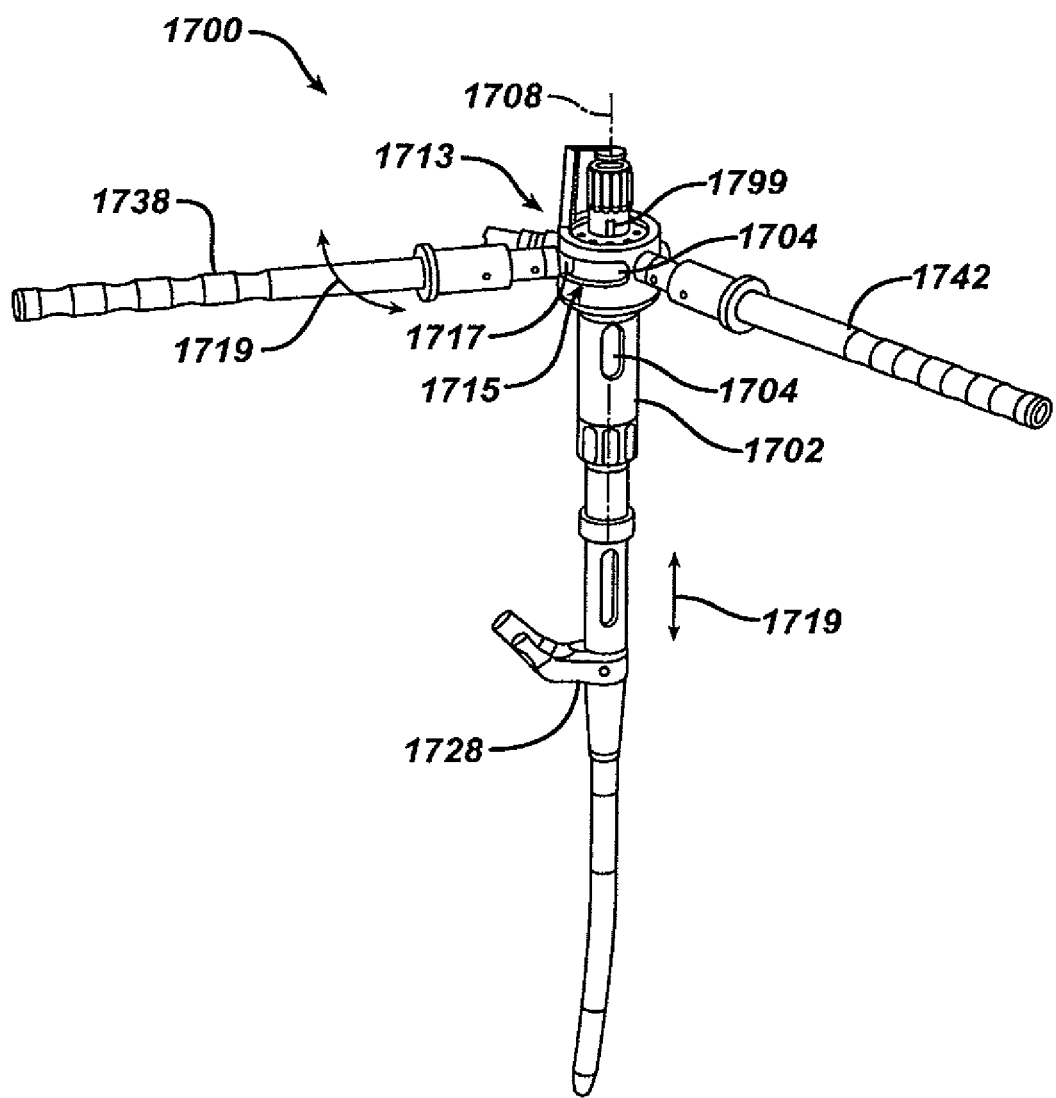
FIG. 75 is a plan view of a proximal body implant/arcuate distal stem implant assembly in cooperation with an assembly tool according to yet another embodiment of the present invention showing an assembly tool with a spiral engagement mechanism.

Referring now to FIG. 75, another embodiment of the present invention is shown as assembly tool 1700. The assembly tool includes a first member 1702 in the form of a hollow cylindrical body. The assembly tool 1700 further includes a second member 1704 in the form of a hollow tube. The tube 1704 is rotatively fitted within the first member or body 1702. An orientation stem 1799 is slidably fitted within the second member or tube 1704.

A spiral cam mechanism 1713 is utilized to move the second member 1704 along longitudinal axis 1708 of assembly tool 1700. Spiral cam mechanism 1713 includes a spiral cam shaped opening 1715 formed in first member or body 1702. The opening 1715 exposes second member or tube 1704. A follower 1717 extends outwardly from the second member 1704 through cam shaped opening 1715 in first member 1702. The follower 1717 is attached to the actuator 1738 and is positioned in the opening 1715 for matingly engagement with the body 1702. As the actuator 1738 is rotated in the direction of arrows 1719 the second member 1704 is caused to rotate to advance the second member 1704 in the direction of arrows 1719 along the longitudinal axis 1708 of the assembly tool 1700.

Figure 75A:
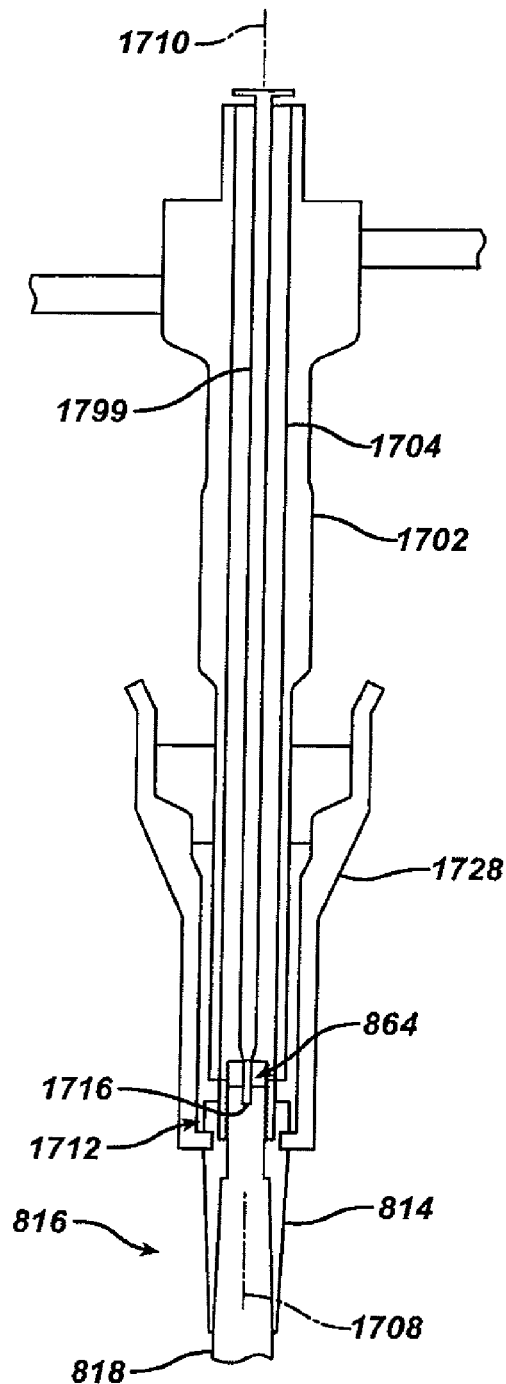
FIG. 75A is a partial plan view partially in cross section of FIG. 75 showing the actuation members in greater detail.
Figure 75B:
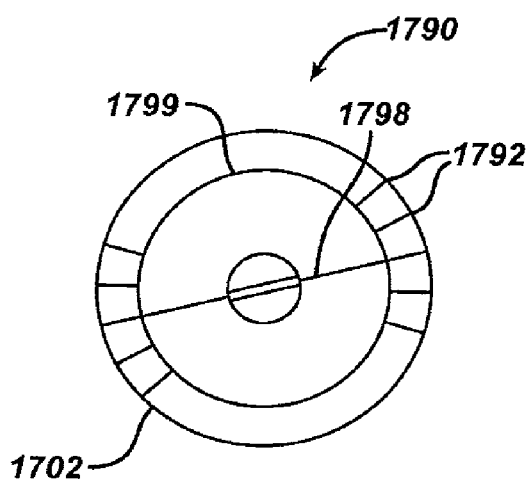
FIG. 75B is a top view of FIG. 75 showing an alignment feature in greater detail.

Referring now to FIG. 75A, a first orientor actuator 1728 similar to the first orientor 928 of FIGS. 31-51 is secured to the first member 1702. A stem 1799 slideably fits within the second member or tube 1704 and includes a second orientor or tang 1716, which mates with slot 864 in the proximal body 814 of the prosthesis 816.

Referring now to FIG. 75, indicia 1790 utilized to orient the proximal body 814 to the distal stem of the prosthesis 816. The stem 1799 includes a radial mark 1798, which is aligned with body indicia 1792 located on first member or body 1702 of the assembly tool 1700. The body indicia 1792 and the radial mark 1798 are utilized to determine and establish the angular orientation of the proximal body 812 to the distal stem 818.

Referring again to FIG. 31, another embodiment of the present invention is shown as kit 1000. The kit 1000 includes an implant 816 as well as the assembly tool 900

Although the present invention and its advantages have been described in detail, it should be understood that various changes, substitutions, and alterations can be made therein without departing from the spirit and scope of the present invention as defined by the appended claims.

We claim:

1. An assembly tool and prosthesis for use in joint arthroplasty, comprising:
a first member defining a first member longitudinal axis and configured to be operably engaged with a first component of the prosthesis;

a second member operably associated with a second component of the prosthesis, at least one of said first member and said second member being adapted to provide for the assembly of the first component to the second component, said second member operably associated with said first member for relative motion therebetween along the first member longitudinal axis; and an angular orientation feature cooperating with at least one of said first member and said second member for at least one of replicating and measuring the relative angular orientation of the first component with respect to the second component, wherein the first component and the second component are configured such that movement of the first member in a first direction along the first member longitudinal axis without rotation of any portion of the prosthesis about the first member longitudinal axis forces the first component to move in the first direction while the second member and the second component remain fixed with respect to the first member longitudinal axis thereby directly locking the first component with the second component.

2. The assembly tool and prosthesis of claim 1:
wherein said first member is adapted to provide relative motion with respect to said second member along the first member longitudinal axis when said first member is rotated relative to said second member about the first member longitudinal axis.

3. The assembly tool and prosthesis of claim 2:
wherein said first member comprises a first member relative motion feature; and
wherein said second member comprises a second member relative motion feature, the first member relative motion feature and the second member relative motion feature cooperating with each other to provide the relative motion of said first member with respect to said second member.

4. The assembly tool and prosthesis of claim 3, wherein at least one of said first member relative motion feature and said second member relative motion feature comprises threads.

5. The assembly tool and prosthesis of claim 3, wherein at least one of said first member relative motion feature and said second member relative motion feature is adapted to provide for a predetermined limited-amount of relative motion of said first member with respect to said second member along the first member longitudinal axis.

6. The assembly tool and prosthesis of claim 2:
wherein said second member defines a central cavity therein; and
further comprising a translating member cooperable with said second member and fitted at least partially in the central cavity, said translating member defining a longitudinal axis thereof and adapted to translate along the translating member longitudinal axis when said first member is rotated.

7. The assembly tool and prosthesis of claim 6, further comprising a third member defining a longitudinal axis thereof and cooperable with said translating member, said third member adapted to translate along the third member longitudinal axis when said translating member translates along the translating member longitudinal axis and adapted to be manually rotated about the third member longitudinal axis.

8. The assembly tool and prosthesis of claim 2, wherein said second member is axially adjustable along the first member longitudinal axis.

9. The assembly tool and prosthesis of claim 1:
wherein said angular orientation feature comprises indicia on one of said first member and said second member.

10. The assembly tool and prosthesis of claim 1, wherein at least one of said first member and said second member comprise a handle extending outwardly from one of said first member and said second member.

11. The assembly tool and prosthesis of claim 1:
wherein said second member comprises a body defining a generally cylindrical longitudinal bore therein; and
wherein said first member comprises a portion thereof threadedly engaged with and matingly fitted to traverse within the cylindrical longitudinal bore of said second member.

12. The assembly tool and prosthesis of claim 1, further comprising a cooperating member for cooperation with the second component, said cooperating member cooperating with said angular orientation feature to at least one of replicate and measure the relative angular orientation of the first component with respect to the second component.

13. The assembly tool and prosthesis of claim 1, wherein at least one of said first member and said second member has a two-piece construction.

14. The assembly tool and prosthesis of claim 1:
wherein the second component defines an internal taper therein;
wherein the first component includes an external taper thereon and an external thread extending from the external taper; and
wherein said first member defines an internal thread for mating engagement with the external thread of the first component.

15. The assembly tool and prosthesis of claim 1, further comprising one of a displacement measuring device and force measuring device for measuring the corresponding one of the displacement and force related to the relative motion of said second member with respect to said first member.

16. The assembly tool and prosthesis of claim 1, wherein said angular orientation feature comprises;
a first orientor connected to said first member for cooperation with the first component, said first component including a first timing feature, said first orientor operably associated with the first timing feature; and
a second orientor operably associated with said second member for cooperation with the second component, said second component including a second timing feature, said second orientor operably associated with the second timing feature.

17. The assembly tool and prosthesis of claim 16, wherein said first orientor is at least one of slidably and pivotably connected to said first member.

* * * * *